US009303255B2

(12) United States Patent
Shigemori et al.

(10) Patent No.: US 9,303,255 B2
(45) Date of Patent: Apr. 5, 2016

(54) ELECTRODE HAVING ENZYME CRYSTALS IMMOBILIZED THEREON, METHOD FOR PRODUCING ELECTRODE HAVING ENZYME CRYSTALS IMMOBILIZED THEREON, AND BIOLOGICAL FUEL CELL AND BIOSENSOR PROVIDED WITH ELECTRODE HAVING ENZYME CRYSTALS IMMOBILIZED THEREON

(75) Inventors: Yasushi Shigemori, Kisarazu (JP); Yuichiro Nakaoki, Kisarazu (JP); Tsutomu Mikawa, Ota-ku (JP)

(73) Assignees: AISIN SEIKI KABUSHIKI KAISHA, Kariya-shi (JP); RIKEN, Wako-shi (JP)

( * ) Notice: Subject to any disclaimer, the term of this patent is extended or adjusted under 35 U.S.C. 154(b) by 317 days.

(21) Appl. No.: 13/818,459

(22) PCT Filed: Aug. 24, 2011

(86) PCT No.: PCT/JP2011/069060
§ 371 (c)(1),
(2), (4) Date: Feb. 22, 2013

(87) PCT Pub. No.: WO2012/026493
PCT Pub. Date: Mar. 1, 2012

(65) Prior Publication Data
US 2013/0224824 A1    Aug. 29, 2013

(30) Foreign Application Priority Data

Aug. 26, 2010  (JP) .................................. 2010-189788

(51) Int. Cl.
| C12N 11/06 | (2006.01) |
| C12N 9/04 | (2006.01) |
| C12N 9/02 | (2006.01) |
| C12Q 1/00 | (2006.01) |
| H01M 4/90 | (2006.01) |
| H01M 8/16 | (2006.01) |
| C12N 11/14 | (2006.01) |
| C25B 11/04 | (2006.01) |
| H01M 8/00 | (2006.01) |

(52) U.S. Cl.
CPC ............. *C12N 11/06* (2013.01); *C12N 9/0006* (2013.01); *C12N 9/0061* (2013.01); *C12N 11/14* (2013.01); *C12Q 1/001* (2013.01); *C12Y 101/05002* (2013.01); *C25B 11/0442* (2013.01); *H01M 4/90* (2013.01); *H01M 4/9008* (2013.01); *H01M 8/00* (2013.01); *H01M 8/16* (2013.01); *Y02E 60/527* (2013.01); *Y02P 70/56* (2015.11)

(58) Field of Classification Search
None
See application file for complete search history.

(56) References Cited

U.S. PATENT DOCUMENTS

| 4,556,635 A | 12/1985 | Hitzman et al. |
| 5,932,212 A | 8/1999 | Khalaf |
| 6,042,824 A | 3/2000 | Khalaf |
| 2009/0035828 A1 | 2/2009 | Abraham et al. |
| 2009/0305113 A1 | 12/2009 | Minteer et al. |
| 2011/0014549 A9 | 1/2011 | Minteer et al. |
| 2011/0059374 A1 | 3/2011 | Kumita et al. |
| 2011/0200889 A1 | 8/2011 | Kumita et al. |

FOREIGN PATENT DOCUMENTS

| JP | 55 78241 | 6/1980 |
| JP | 56 36048 | 4/1981 |
| JP | 2007 225444 | 9/2007 |
| JP | 2007 280944 | 10/2007 |
| JP | 2008 96352 | 4/2008 |
| JP | 2009 515303 | 4/2009 |
| JP | 2009 245920 | 10/2009 |
| JP | 2010 43978 | 2/2010 |
| WO | 92 02617 | 2/1992 |
| WO | 97 44445 | 11/1997 |
| WO | 2005 066341 | 7/2005 |

OTHER PUBLICATIONS

Drenth, Jan "Crystallizing a Protein", Principles of Protein Crystallography (Springer) 2007, Chapter 1.8, pp. 17-20 (e-ISBN-13: 978-0-387-33746-3).*

Roy, J.J.; Abraham, T.E.; Abhijith, K.S.; Kumar, P.V.S.; Thakur, M.S., "Biosensor for the determination of phenols based on Cross-Linked Enzyme Crystals (CLEC) of laccase" Biosensors and Bioelectronics, Jul. 2005, 21(1), pp. 206-211.*

Zelinski, T. and Waldmann, H. "Cross-Linked Enzyme Crystals (CLECs): Efficient and Stable Biocatalysts for Preparative Organic Chemistry" Angew Chem Int Ed, 1997, 36(7) 722-724.*

(Continued)

*Primary Examiner* — Laura Schuberg
*Assistant Examiner* — Aaron J Kosar
(74) *Attorney, Agent, or Firm* — Oblon, McClelland, Maier & Neustadt, L.L.P.

(57) ABSTRACT

An objective of the present invention is to establish a technique for making it possible to immobilize an enzyme on an electrically conductive base material in a uniformly, high density, and constantly aligned orientation, for the purpose of constructing an enzyme electrode having improved electrode performance. An electrode having enzyme crystals immobilized thereon, the electrode being provided with an electrically conductive base material that can be connected to an external circuit and enzyme crystals that serve as an electrode catalyst, wherein the enzyme crystals are immobilized on the electrically conducive base material; a method for producing an electrode having enzyme crystals immobilized thereon; and a biological fuel cell and a biosensor which are provided with an electrode having enzyme crystals immobilized thereon.

10 Claims, 13 Drawing Sheets

(56) References Cited

OTHER PUBLICATIONS

Tan, Yueming; Xie, Qingji; Huang, Jinhua; Duan, Weisheng; Ma, Ming; Yao, Shouzhuo "Study on glucose biofuel cells using an electrochemical noise device" Electroanalysis (2008), 20(14), 1599-1606.*

Hernandez-Perez, T., et al., "Immobilization of Catalase Monocrystals on Highly Oriented Pyrolytic Graphite by the Growth of Polypyrrole Films for AFM Investigations," Electrochemical and Solid-State Letters, vol. 5, No. 8, pp. E37-E39, (May 23, 2002).

Oubrie, A., et al., "The 1.7 A Crystal Structure of the Apo Form of the Soluble Quinoprotein Glucose Dehydrogenase from Acinetobacter calcoaceticus Reveals a Novel Internal Conserved Sequence Repeat," J. Mol. Biol., vol. 289, pp. 219-333, (1999).

Enguita, F.J., et al., "Spore-coat laccase CotA from *Bacillus subtilis*: crystallization by the MAD method," Acta Crystallographica Section D Biological Crystallography, vol. D58, No. 9, pp. 1490-1493, (2002).

Tsujimura, S., et al., "Recent Development of Enzyme-based Biofuel Cells," GS Yuasa Tech. Rep., vol. 5, No. 2, pp. 1-6, (2008) (with English abstract).

Martins, L.O., et al., "Molecular and Biochemical Characterization of a Highly Stable Bacterial Laccase That Occurs as a Structural Component of the *Bacillus subtilis* Endospore Coat," The Journal of Biological Chemistry, vol. 277, No. 21, pp. 18849-18859, (May 24, 2002).

International Preliminary Report on Patentability Issued Mar. 19, 2013 in PCT/JP11/069060 Filed Aug. 24, 2011, 7 page.

International Search Report Issued Sep. 20, 2011 in PCT/JP11/69060 Filed Aug. 24, 2011, 2 pages.

* cited by examiner

ELECTRODE HAVING ENZYME CRYSTALS IMMOBILIZED THEREON, METHOD FOR PRODUCING ELECTRODE HAVING ENZYME CRYSTALS IMMOBILIZED THEREON, AND BIOLOGICAL FUEL CELL AND BIOSENSOR PROVIDED WITH ELECTRODE HAVING ENZYME CRYSTALS IMMOBILIZED THEREON

TECHNICAL FIELD

The present invention relates to an electrode having enzyme crystals immobilized thereon, a method for producing an electrode having enzyme crystals immobilized thereon, and a biological fuel cell and biosensor provided with an electrode having enzyme crystals immobilized thereon. More specifically, the present invention relates to an electrode having enzyme crystals immobilized thereon, where enzyme crystals are immobilized on the surface of an electroconductive base material, as well as to a method for producing an electrode having enzyme crystals immobilized thereon and a biological fuel cell and biosensor provided with the electrode having enzyme crystals immobilized thereon.

BACKGROUND ART

Biological fuel cells, which use a biomass resource, have recently been proposed as being the next generation of energy, due to the high energy efficiency and low environmental impact thereof. Organisms, including microorganisms, generate ATP and other chemical energy substances (bonding energy) in in vivo metabolic processes involving the oxidative decomposition of carbohydrates, proteins, lipids, and the like by enzymes and other biological catalysts, thus acquiring the energy needed for life activity. A biological fuel cell is a power generation device that removes energy generated in such in vivo metabolic processes to an electrode as electrical energy. In particular, enzyme fuel cells, which conjugate the electrode reaction and a substrate-specific catalytic reaction of an enzyme, have been attracting attention as clean power sources that are especially safe and have an especially low environmental impact, because enzyme fuel cells are able to use, as fuel, compounds present in the environment, such as sugars and amines.

The selection of an enzyme that will serve as an electrode catalyst is a very important element in the construction of an enzyme fuel cell. For the anode (negative electrode) side, an enzyme that oxidatively decomposes the fuel will be selected, while an enzyme that reduces oxygen will be selected for the cathode (positive electrode) side. For example, glucose dehydrogenase is used as the anode-side catalyst in a case where, for example, glucose is to serve as the fuel. By contrast, a laccase or the like could be used as the cathode-side catalyst (Patent Document 1). Laccases are enzymes that are known to be widely present in microorganisms, fungi, plants, and so forth. For example, CotA laccase from *Bacillus subtilis* and other laccases have been reported, the sequences thereof determined and the crystal structures thereof analyzed (Non-patent Document 1, Non-patent Document 2).

Successfully putting an enzyme fuel cell to practical use hinges on the successful construction of an electrode having an enzyme immobilized thereon, and thus enzyme electrodes whereby the catalytic functions of enzymes can be maximized are being constructed. A variety of electrodes where the electrode surface has, immobilized thereon, either an enzyme or an electron-transfer mediator that mediates the electron transfer between the electrode and the enzyme have been reported to date. Reported examples include an enzyme electrode where direct bonding between a hydrophobic group of a membrane-bound enzyme and a hydrophobic group of a carbon base material has immobilized the membrane-bound enzyme onto the carbon base material (Patent Document 2), as well as an enzyme electrode where an enzyme configured to be a protein that includes a cytochrome complex (cytochrome C) site has been immobilized onto an electroconductive base material made of carbon having a hydrophobic surface (Patent Document 3). It has also been reported that in the process of immobilizing an enzyme or an electron-transfer mediator onto an electroconductive base material, an electrode having enzymes immobilized thereon exhibiting excellent electrode performance can be manufactured by bonding the mediator to an organic polymer chain to form a polymer-mediator composite, dispersing same in a solvent having an electric permittivity of 24 or less to improve dispersibility, and coating the surface of the electroconductive base material with the resulting dispersion (Patent Document 4), and further that adding an organic solvent to the solution used in the process of immobilizing the enzyme onto the electroconductive base material makes it possible to readily promote osmosis of the enzyme into the interior of the electrode and construct an electrode where the enzyme has been immobilized on the surface of the interior of the electrode in a three-dimensional and high density fashion, without adversely affecting the activity of the enzyme, even though the electrode may have a very complex structure (Patent Document 5). In another report, electrodes having a structure where a positive electrode and a negative electrode face each other with an electrolyte interposed therebetween were constructed, among which, as one example of the electrode, an electroconductive base material made of carbon felt was used, the enzyme being immobilized on the electrode by soaking the electroconductive base material with the enzyme (Patent Document 6).

However, in the prior art described above, all instances involved using an enzyme solution in a solution state where the enzyme has been dispersed into water or a buffer solution to immobilize the enzyme onto the carbon base material or other electroconductive base material. For this reason, a problem has emerged in that the enzyme on the electrode has become unstable and an electric current value that is consistent with the amount of enzyme binding cannot be obtained. Another problem has emerged in that the types of enzyme that can be applied have been limited, the applications of the electrode disclosed in Patent Document 2 being limited to membrane-bound enzymes and the electrode disclosed in Patent Document 3 not being applicable to enzymes having a hydrophilic surface, and so forth.

In order to obtain an adequate electric current value in an enzyme electrode, there must be smooth electron transfer between the enzyme and the electrode via the electron-transfer mediator. For this reason, it has been necessary to have a greater amount of enzyme present at a location in close proximity to the surface of the electrode. This signifies that the electrode performance of the enzyme electrode is significantly affected by the relative positional relationship between the enzyme, the electron-transfer mediator, and the electrode. For this reason, raising the concentration in the process of immobilizing the enzyme onto the surface of the electrode has been regarded as very important in order to obtain an enzyme electrode that exhibits excellent electrode performance.

There are limitations, however, to the use of a highly concentrated solution in a case where the enzyme is to be immobilized onto the electroconductive base material in a solution state. An enzyme is constituted of amino acids that are either hydrophilic or hydrophobic, and, when in a solution, adopts such a structure that the hydrophilic amino acids are present on the surface. For this reason, precipitation will generally not take place at concentrations of about several milligrams/milliliters. However, when the enzyme is highly concentrated, there are incidental interactions between the hydrophobic portions when the enzyme molecules come into close proximity to each other; aggregation and precipitation take place as a result, leading to denaturing of the enzyme and exposure of the enzyme in an unstable state. In addition, once precipitation takes place, the precipitation will continue to increase at an accelerated pace. Therefore, when the enzyme concentration in an enzyme solution is increased (generally, when the concentration is in excess of 50 mg/cm$^3$), the dispersibility of the enzyme in the solution is worsened, and the enzyme will be immobilized onto the surface of the electroconductive base material in an aggregated, i.e., denatured state. This causes electron transfer on the electrode to no longer proceed in a smooth manner, and a problem emerges in that the resulting enzyme electrode will have poor electrode performance.

As an example, according to a specific disclosure made in Patent Document 2, the enzyme concentration in a solution used in the process of constructing an electrode is 0.57 mg/mL, i.e., the maximum amount of membrane-bound enzyme immobilized onto the carbon base material is 1.11 µg/cm$^2$. According to a specific disclosure made in Patent Document 3, it is stated that a glassy carbon electrode is constructed by adding 5 µL of a 1 mg/mL enzyme solution in a dropwise manner thereon. Thus, since the enzyme concentration in the solution used is 1 mg/mL, the maximum amount of membrane-bound enzyme immobilized onto the carbon base material is 71.4 µg/cm$^2$. Further, according to a specific disclosure made in Patent Document 4, it is stated that an electrode is constructed by adding 8 µL of a phosphate buffer solution having an enzyme concentration of 5 mg/mL in a dropwise manner onto a carbon paper surface. Thus, the enzyme concentration in the solution used is 5 mg/mL; calculated on the basis thereof, the maximum amount of enzyme immobilized onto the carbon sheet is 51.0 µg/cm$^2$. According to a specific disclosure made in Patent Document 5, 13.8 mg of an enzyme is dissolved in 200 µL of a buffer solution and the enzyme solution is added in a dropwise manner onto a glassy carbon disc electrode surface; therefore, the enzyme concentration in the solution used is 69 mg/mL. According to a specific disclosure made in Patent Document 6, the enzyme concentration in the solution used is 50 mg/mL. In the prior art, thus, it has been presumed that the enzyme concentration used in immobilization is as described above.

Factors whereby an amount of electric current that is consistent with the amount of enzyme binding might not be obtained also include the fact that there is inadequate optimization of the directionality (orientation) of the enzyme binding on the electrode. When in a solution, the enzyme is present in a disordered state, without a unified orientation. When immobilization is carried out in a solution state, therefore, the enzyme binds to the electroconductive base material with a random directionality, and this leads to a decrease in output and the like. For this reason, the ability to control the orientation of the enzyme on the electrode has been a technical problem requiring improvement, from the point of view of electrode performance. Furthermore, in immobilization in a solution state, immobilizing the enzyme onto the electrode while a constant dispersibility is upheld is difficult, and for this reason a problem has emerged in that the enzyme readily dissociates from the electrode within the electrolyte solution, and there is a decline in the electric current value when the oxidation current is measured.

PRIOR ART DOCUMENTS

Patent Documents

[Patent Document 1] Japanese Translation of PCT International Application No. 2009-515303
[Patent Document 2] Japanese Laid-open Patent Application No. 2010-43978
[Patent Document 3] Japanese Laid-open Patent Application No. 2007-225444
[Patent Document 4] Japanese Laid-open Patent Application No. 2008-96352
[Patent Document 5] Japanese Laid-open Patent Application No. 2007-280944
[Patent Document 6] Japanese Laid-open Patent Application No. 2009-245920

Non-Patent Documents

[Non-patent Document 1] Martins L O, Soares C M, Pereira M M, Teixeira M, Costa T, Jones G H, Henriques A O, "Molecular and biochemical characterization of a highly stable bacterial laccase that occurs as a structural component of the *Bacillus subtilis* endospore coat," J. Biol. Chem., 2002, vol. 277, no. 21, pp. 18849-18859
[Non-patent Document 2] Enguita F J, Matias P M, Martins L O, Plácido D, Henriques A O, Carrondo M A, "Spore-coat laccase CotA from *Bacillus subtilis*: crystallization and preliminary X-ray characterization by the MAD method," Acta Crystallogr. D. Biol. Crystallogr., 2002, 58 (Pt 9), pp. 1490-1493

DISCLOSURE OF THE INVENTION

Problems that the Invention is Intended to Solve

In view whereof, in order to resolve the foregoing problems, a purpose of the present invention is to establish a technique for making it possible to immobilize an enzyme on an electrically conductive base material in a uniformly, high density, and constantly aligned orientation, for the purpose of constructing an enzyme electrode having improved electrode performance. A purpose of the present invention is also to provide an electrode having enzyme crystals immobilized thereon constructed by immobilizing an enzyme onto an electrically conductive base material in a uniformly, high density, and constantly aligned orientation; another purpose is to improve electrode performance through smooth electron transfer in an electrode. A further purpose is to provide a biological fuel cell and biosensor using the electrode having enzyme crystals immobilized thereon.

Means for Solving the Problems

As the result of extensive research aimed at resolving the foregoing problems, the present inventors have discovered that immobilizing an enzyme crystal onto the surface of an electroconductive base material makes it possible to immobilize an enzyme onto the surface of an electroconductive base material with a uniformly, high density, and constantly aligned orientation, thereby making it possible to construct an electrode having enzyme crystals immobilized thereon capable of smooth catalytic function. The present inventors have also discovered that the electrode having enzyme crystals immobilized thereon of such description can achieve the smooth progression of electron transfer on the electrode, and exhibits excellent electrode performance. The present inventors have perfected the present invention on the basis of these findings.

More specifically, in order to achieve the foregoing objective, provided is the invention illustrated by [1] to [28] below.

[1] An electrode having enzyme crystals immobilized thereon, provided with an electroconductive base material that can be connected to an external circuit and enzyme crystals serving as an electrode catalyst, the enzyme crystals being immobilized on the electroconductive base material.

[2] The electrode having enzyme crystals immobilized thereon, configured to be a microelectrode in which the enzyme crystals have been immobilized on a microfabricated electroconductive base material.

[3] The electrode having enzyme crystals immobilized thereon, wherein the enzyme crystals are crystals of an enzyme for catalyzing an oxidation reaction.

[4] The electrode having enzyme crystals immobilized thereon, wherein the enzyme crystals are crystals of pyrroloquinoline quinone-dependent glucose dehydrogenase from *Acinetobacter calcoaceticus*.

[5] The electrode having enzyme crystals immobilized thereon, wherein the pyrroloquinoline quinone-dependent glucose dehydrogenase from *Acinetobacter calcoaceticus* has the amino acid sequence of any of (A) to (C) below.
   (A) The amino acid sequence illustrated by SEQ ID NO: 2
   (B) The amino acid sequence illustrated by SEQ ID NO: 4
   (C) An amino acid sequence having at least 80% homology with the amino acid sequence in (A) or (B)

[6] The electrode having enzyme crystals immobilized thereon, wherein the enzyme crystals are crystals of an enzyme for catalyzing a reduction reaction.

[7] The electrode having enzyme crystals immobilized thereon, wherein the enzyme crystals are crystals of CotA laccase from *Bacillus subtilis*.

[8] The electrode having enzyme crystals immobilized thereon as set forth in the fifth aspect, wherein the CotA laccase from *Bacillus subtilis* has the amino acid sequence of any of (A) to (C) below.
   (A) The amino acid sequence illustrated by SEQ ID NO: 6
   (B) The amino acid sequence illustrated by SEQ ID NO: 8
   (C) An amino acid sequence having at least 80% homology with the amino acid sequence in (A) or (B)

According to the first aspect described above, an electrode having enzyme crystals immobilized thereon where enzyme crystals have been immobilized on an electroconductive base material can be provided. In the enzyme crystal, enzyme molecules have been aligned in a state where regularity on the molecular level has been maintained, and thus the electrode having enzyme crystals immobilized thereon is such that the enzyme, which is the electrode catalyst, has been immobilized onto the surface of the electroconductive base material with a uniformly, high density, and constantly aligned orientation. The enzyme crystals have been immobilized in a state where the catalytic activity of the functional molecules is maintained. For this reason, the electrode having enzyme crystals immobilized thereon makes it possible to facilitate smooth electron transfer and produce excellent electrode performance. In immobilization in a solution state in which the enzyme has been dispersed in a solvent, as in the prior art, the dispersibility is worsened when the enzyme concentration is heightened, and the result is that the enzyme is immobilized in an aggregated state on the surface of the electroconductive base material; a problem then emerges in that smooth progress of electron transfer in the electrode is impeded, giving rise to a decline in electrode performance. However, the electrode having enzyme crystals immobilized thereon in which the enzyme has been immobilized in a uniformly, high density, and constantly aligned orientation is intended to solve such problems. Therefore, the electrode having enzyme crystals immobilized thereon, which has vastly superior electrode performance to that of a conventional enzyme electrode, is an electrode of high industrial utility value that can be utilized in a variety of industrial fields, including biological fuel cells and biosensors.

Further, according to the second aspect described above, a microelectrode on which a superconcentrated enzyme has been immobilized in a uniformly, high density, and constantly aligned orientation in a micro-sized region can be provided, and the utility value of the microelectrode can be further increased.

According to the third through fifth aspects described above, immobilizing an enzyme for catalyzing an oxidation reaction as an enzyme crystal makes it possible to provide an electrode that can be utilized in a biological fuel cell, biosensor, and the like. In the case of an electrode in a biological fuel cell, the electrode having enzyme crystals immobilized thereon can be utilized as the anode. Because pyrroloquinoline quinone-dependent glucose dehydrogenase has a very fast reaction rate, is less susceptible to the effects of dissolved oxygen, and can be directly immobilized on an electrode, an advantage emerges in that the electrode reaction and, by extension, the electrode structure can be simplified, and thus an electrode of even higher industrial utility value can be provided. Since glucose is the substrate for pyrroloquinoline quinone-dependent glucose dehydrogenase, the electrode having enzyme crystals immobilized thereon can be utilized in the applications of a glucose sensor, a biological fuel cell in which the fuel is glucose, and a variety of other fields, such as electronics, medicine, food products, and the environment.

Moreover, according to the sixth through eighth aspects described above, immobilizing an enzyme for catalyzing a reduction reaction as the enzyme crystals makes it possible to provide an electrode that can be utilized in a biological fuel cell, biosensor, and the like. In the case of an electrode in a biological fuel cell, [the electrode having enzyme crystals immobilized thereon] can be utilized as the cathode. CotA laccase from *Bacillus subtilis* is a multi-copper oxidase, and is a protein molecule that includes four copper atoms needed for enzyme activity. The enzyme carries out the electron reduction of molecular oxygen using electrons pulled from the substrate, thus catalyzing a reaction that generates water molecules, and can therefore be utilized as an electrode catalyst. In particular, because oxygen can be reduced, the value of utility as a cathode of a biological fuel cell is very high. The utility value as a biosensor for detecting phenolic compounds is also very high. The electrode having enzyme crystals immobilized thereon can therefore be utilized in a variety of fields, such as electronics, medicine, food products, and the environment.

[9] A method for producing an electrode having enzyme crystals immobilized thereon, in which enzyme crystals have been immobilized as an electrode catalyst on an electroconductive base material that can be connected to an external circuit, wherein the electrode having enzyme crystals immobilized thereon is produced by immobilizing the enzyme crystals on the electroconductive base material.

[10] The method for producing an electrode having enzyme crystals immobilized thereon, wherein the enzyme is crystallized from an enzyme solution before the enzyme crystals are immobilized.

[11] The method for producing an electrode having enzyme crystals immobilized thereon, wherein the enzyme is crystallized in an environment of a vapor diffusion method.

According to the ninth aspect described above, a method for producing an electrode having enzyme crystals immobilized thereon where enzyme crystals have been immobilized on an electroconductive base material can be provided. In the enzyme crystals, enzyme molecules have been aligned in a state where regularity on the molecular level has been maintained, and thus the enzyme, which is the electrode catalyst, can be immobilized onto the surface of the electroconductive base material with a uniformly, high density, and constantly aligned orientation. The enzyme crystals are immobilized in a state where the catalytic activity of the functional molecules is maintained. This makes it possible to produce an electrode having enzyme crystals immobilized thereon whereby electron transfer can proceed smoothly and which can exhibit excellent electrode performance. In the method of immobilization in a solution state in which the enzyme has been dispersed in a solvent, as in the prior art, the dispersibility is worsened when the enzyme concentration is heightened, and the result is that the enzyme is immobilized in an aggregated state on the surface of the electroconductive base material; a problem then emerges in that smooth progress of electron transfer in the electrode is impeded, giving rise to a decline in electrode performance. However, the method for producing an electrode having enzyme crystals immobilized thereon for making it possible to immobilize an enzyme with a uniformly, high density, and constantly aligned orientation is intended to resolve such problems. Therefore, an electrode having enzyme crystals immobilized thereon which has vastly superior electrode performance to that of a conventional enzyme electrode can be produced, and the technique is thus of high industrial utility value that can be utilized in a variety of industrial fields, including biological fuel cells and biosensors.

According to the tenth and eleventh aspects described above, it is possible to adjust the enzyme crystals being immobilized on the electrode having enzyme crystals immobilized thereon to a desired size, shape, and quality whereby functionality as an electrode catalyst can be maximized; this makes it possible to produce an electrode having enzyme crystals immobilized thereon whereby electron transfer can proceed smooth and which can exhibit excellent electrode performance.

[12] A method for producing an electrode having enzyme crystals immobilized thereon, in which enzyme crystals have been immobilized on (*1) an electroconductive base material that can be connected to an external circuit, wherein the electrode having enzyme crystals is immobilized thereon is produced by crystallizing an enzyme from an enzyme solution on the electroconductive base material and immobilizing the enzyme crystals on the electroconductive base material.

[13] The method for producing an electrode having enzyme crystals immobilized thereon, wherein the enzyme is crystallized in an environment of a vapor diffusion method.

[14] An electrode having enzyme crystals immobilized thereon produced by the method for producing an electrode having enzyme crystals immobilized thereon of the present invention.

[15] The electrode having enzyme crystals immobilized thereon, configured to be a microelectrode in which the enzyme crystals have been immobilized on a microfabricated electroconductive base material.

[16] The electrode having enzyme crystals immobilized thereon, wherein the enzyme crystals are crystals of an enzyme for catalyzing an oxidation reaction.

[17] The electrode having enzyme crystals immobilized thereon, wherein the enzyme crystals are crystals of pyrroloquinoline quinone-dependent glucose dehydrogenase from *Acinetobacter calcoaceticus*.

[18] The electrode having enzyme crystals immobilized thereon, wherein the pyrroloquinoline quinone-dependent glucose dehydrogenase from *Acinetobacter calcoaceticus* has the amino acid sequence of any of (A) to (C) below.
(A) The amino acid sequence illustrated by SEQ ID NO: 2
(B) The amino acid sequence illustrated by SEQ ID NO: 4
(C) An amino acid sequence having at least 80% homology with the amino acid sequence in (A) or (B)

[19] The electrode having enzyme crystals immobilized thereon, wherein the enzyme crystals are crystals of an enzyme for catalyzing a reduction reaction.

[20] The electrode having enzyme crystals immobilized thereon, wherein the enzyme crystals are crystals of CotA laccase from *Bacillus subtilis*.

[21] The electrode having enzyme crystals immobilized thereon as set forth in the fifth aspect, wherein the CotA laccase from *Bacillus subtilis* has the amino acid sequence of any of (A) to (C) below.
(A) The amino acid sequence illustrated by SEQ ID NO: 6
(B) The amino acid sequence illustrated by SEQ ID NO: 8
(C) An amino acid sequence having at least 80% homology with the amino acid sequence in (A) or (B)

According to the twelfth aspect described above, a method for producing an electrode having enzyme crystals immobilized thereon where enzyme crystals have been immobilized on an electroconductive base material can be provided. In the enzyme crystals, enzyme molecules have been aligned in a state where regularity on the molecular level has been maintained, and thus the enzyme, which is the electrode catalyst, can be immobilized on the surface of the electroconductive base material with a uniformly, high density, and constantly aligned orientation. The enzyme crystals are immobilized in a state where the catalytic activity of the functional molecules is maintained. In particular, carrying out the crystallization of the enzyme on the surface of the electroconductive base material makes it possible to further align the orientation together, and also possible to immobilize the enzyme crystals on the electrode in such a fashion that the crystalline state will never be broken. This makes it possible to produce an electrode having enzyme crystals immobilized thereon whereby electron transfer can proceed smoothly and which can exhibit excellent electrode performance. There can also be expected to be an increase in the electric current density of the electrode, especially in the initial electric current. In immobilization in a solution state in which the enzyme has been dispersed in a solvent, as in the prior art, the dispersibility is worsened when the enzyme concentration is heightened, and the result is that the enzyme is immobilized in an aggregated state on the surface of the electroconductive base material; a problem then emerges in that smooth progress of electron transfer in the electrode is impeded, giving rise to a decline in electrode performance. However, the method for producing an electrode having enzyme crystals immobilized thereon for making it possible to immobilize an enzyme with a uniformly, high density, and constantly aligned orientation is intended to resolve such problems. Therefore, an electrode having enzyme crystals immobilized thereon which has vastly superior electrode performance to that of a conventional enzyme electrode can be produced, and the technique is thus of high industrial utility value that can be utilized in a variety of industrial fields, including biological fuel cells and biosensors.

According to the thirteenth aspect described above, it is possible to adjust the enzyme crystals being immobilized on the electrode having enzyme crystals immobilized thereon to a desired size, shape, and quality whereby functionality as an electrode catalyst can be maximized; this makes it possible to produce an electrode having enzyme crystals immobilized thereon whereby electron transfer can proceed smoothly and which can exhibit excellent electrode performance.

According to the fourteenth aspect described above, an electrode having enzyme crystals immobilized thereon where enzyme crystals have been immobilized on an electroconductive base material can be provided. Since the crystallization of the enzyme is carried out on the electroconductive base material, the enzyme crystals are immobilized on the electroconductive base material in a state where the enzyme molecules have been aligned in a state where regularity on the molecular level has been maintained. The electrode having enzyme crystals immobilized thereon therefore has the enzyme, which is the electrode catalyst, immobilized on the surface of the electroconductive base material with a uniformly, high density, and constantly aligned orientation, and in particular achieves unified orientation. Also, the enzyme crystals are immobilized on the electroconductive base material in a state where the catalytic activity of the functional molecules is maintained, and in such a fashion that the crystalline state will never be broken. For this reason, the electrode having enzyme crystals immobilized thereon makes it possible to facilitate smooth electron transfer and produce excellent electrode performance. In immobilization in a solution state in which the enzyme has been dispersed in a solvent, as in the prior art, the dispersibility is worsened when the enzyme concentration is heightened, and the result is that the enzyme is immobilized in an aggregated state on the surface of the electroconductive base material; a problem then emerges in that smooth progress of electron transfer in the electrode is impeded, giving rise to a decline in electrode performance. However, the electrode having enzyme crystals immobilized thereon in which the enzyme has been immobilized in a uniformly, high density, and constantly aligned orientation is intended to solve such problems. Therefore, the electrode having enzyme crystals immobilized thereon, which has vastly superior electrode performance to that of a conventional enzyme electrode, is an electrode of high industrial utility value that can be utilized in a variety of industrial fields, including biological fuel cells and biosensors.

Further, according to the fifteenth aspect described above, a microelectrode on which a superconcentrated enzyme has been immobilized with a uniformly, high density, and constantly aligned orientation in a micro-sized region can be provided, and the utility value of the microelectrode can be further increased.

According to the sixteenth to eighteenth aspects described above, immobilizing an enzyme for catalyzing an oxidation reaction as an enzyme crystal makes it possible to provide an electrode that can be utilized in a biological fuel cell, biosensor, and the like. In the case of an electrode in a biological fuel cell, the electrode having enzyme crystals immobilized thereon can be utilized as the anode. Because pyrroloquinoline quinone-dependent glucose dehydrogenase has a very fast reaction rate, is less susceptible to the effects of dissolved oxygen, and can be directly immobilized on an electrode, an advantage emerges in that the electrode reaction and, by extension, the electrode structure can be simplified, and thus an electrode of even higher industrial utility value can be provided. Since glucose is the substrate for pyrroloquinoline quinone-dependent glucose dehydrogenase, the electrode having enzyme crystals immobilized thereon can be utilized in the applications of a glucose sensor, a biological fuel cell in which the fuel is glucose, and a variety of other fields, such as electronics, medicine, food products, and the environment.

Moreover, according to the nineteenth through twenty-first aspects described above, immobilizing an enzyme for catalyzing a reduction reaction as the enzyme crystals makes it possible to provide an electrode that can be utilized in a biological fuel cell, biosensor, and the like. In the case of an electrode in a biological fuel cell, the electrode having enzyme crystals immobilized thereon can be utilized as the cathode. CotA laccase from *Bacillus subtilis* is a multi-copper oxidase, and is a protein molecule that includes four copper atoms needed for enzyme activity. The enzyme carries out the electron reduction of molecular oxygen using electrons pulled from the substrate, thus catalyzing a reaction that generates water molecules, and can therefore be utilized as an electrode catalyst. In particular, because oxygen can be reduced, the value of utility as a cathode of a biological fuel cell is very high. The utility value as a biosensor for detecting phenolic compounds is also very high. The electrode having enzyme crystals immobilized thereon can therefore be utilized in a variety of fields, such as electronics, medicine, food products, and the environment.

[22] A biological fuel cell provided with the electrode having enzyme crystals immobilized thereon of the present invention.

[23] The biological fuel cell, wherein the enzyme crystals are an enzyme for catalyzing an oxidation reaction. Alternatively, the biological fuel cell, wherein the enzyme crystals are crystals of pyrroloquinoline quinone-dependent glucose dehydrogenase from *Acinetobacter calcoaceticus*. Alternatively, the biological fuel cell, wherein the enzyme crystals are crystals of pyrroloquinoline quinone-dependent glucose dehydrogenase from *Acinetobacter calcoaceticus* having an amino acid sequence of any of (A) to (C) below.
  (A) The amino acid sequence illustrated by SEQ ID NO: 2
  (B) The amino acid sequence illustrated by SEQ ID NO: 4
  (C) An amino acid sequence having at least 80% homology with the amino acid sequence in (A) or (B)

[24] The biological fuel cell, wherein the enzyme crystals are an enzyme for catalyzing a reduction reaction. Alternatively, the biological fuel cell, wherein the enzyme crystals are crystals of CotA laccase from *Bacillus subtilis*. Alternatively, the biological fuel cell, wherein the enzyme crystals are crystals of CotA laccase from *Bacillus subtilis* having the amino acid sequence of any of (A) to (C) below.
  (A) The amino acid sequence illustrated by SEQ ID NO: 6
  (B) The amino acid sequence illustrated by SEQ ID NO: 8
  (C) An amino acid sequence having at least 80% homology with the amino acid sequence in (A) or (B)

[25] A method for producing a biological fuel cell provided with an electrode having an enzyme immobilized thereon, the electrode being formed so that an anode and a cathode face each other, and an ion-conductive material being arranged so as to isolate the anode and cathode from each other, wherein the electrode is the electrode having enzyme crystals immobilized thereon of the present invention.

[26] The method for producing a biological fuel cell, wherein the anode is an electrode having enzyme crystals immobilized thereon on which crystals of an enzyme for catalyzing an oxidation reaction have been immobilized. Alternatively, the anode is an electrode having enzyme crystals immobilized thereon on which crystals of pyrroloquinoline quinone-dependent glucose dehydrogenase from *Acinetobacter calcoaceticus* have been immobilized. Alternatively, the anode is an electrode having enzyme crystals immobilized thereon on which crystals of pyrroloquinoline quinone-dependent glucose dehydrogenase from *Acinetobacter calcoaceticus* having the amino acid sequence of any of (A) to (C) below have been immobilized.

(A) The amino acid sequence illustrated by SEQ ID NO: 2
(B) The amino acid sequence illustrated by SEQ ID NO: 4
(C) An amino acid sequence having at least 80% homology with the amino acid sequence in (A) or (B)

[27] The method for producing a biological fuel cell, wherein the cathode is an electrode having enzyme crystals immobilized thereon on which crystals of an enzyme for catalyzing a reduction reaction have been immobilized. Alternatively, the cathode is an electrode having enzyme crystals immobilized thereon on which crystals of CotA laccase from *Bacillus subtilis* have been immobilized. Alternatively, the cathode is an electrode having enzyme crystals immobilized thereon on which crystals of CotA laccase from *Bacillus subtilis* having the amino acid sequence of any of (A) to (C) below have been immobilized.

(A) The amino acid sequence illustrated by SEQ ID NO: 6
(B) The amino acid sequence illustrated by SEQ ID NO: 8
(C) An amino acid sequence having at least 80% homology with the amino acid sequence in (A) or (B)

According to the twenty-second through twenty-fourth aspects described above, there can be provided a biological fuel cell provided with an electrode having enzyme crystals immobilized thereon whereby electron transfer can proceed in an even smoother manner, and which can exhibit excellent electrode performance. Because the electrode having enzyme crystals immobilized thereon can exhibit excellent electrode performance, the utilization thereof makes high-capacity and high-output power generation possible, and makes it possible to provide a high-performance biological fuel cell having very high power generation efficiency and excellent durability.

Also, according to the twenty-fifth through twenty-seventh aspects described above, there can be provided a method for producing a biological fuel cell provided with an electrode having enzyme crystals immobilized thereon whereby electron transfer can proceed in an even smoother manner, and which can exhibit excellent electrode performance. Because the electrode having enzyme crystals immobilized thereon can exhibit excellent electrode performance, the utilization thereof makes high-capacity and high-output power generation possible, and makes it possible to produce a high-performance biological fuel cell having very high power generation efficiency and excellent durability.

[28] A biosensor provided with the electrode having enzyme crystals immobilized thereon of the present invention.

According to the twenty-eighth aspect described above, there can be provided a biosensor provided with an electrode having enzyme crystals immobilized thereon whereby electron transfer can proceed in an even smoother manner, and excellent electrode performance can be exhibited. Because the electrode having enzyme crystals immobilized thereon can exhibit excellent electrode performance, the utilization thereof makes high-capacity and high-output power generation possible, and makes it possible to produce a highly accurate biosensor having excellent durability.

BEST MODE FOR CARRYING OUT THE INVENTION

Figure 1A:
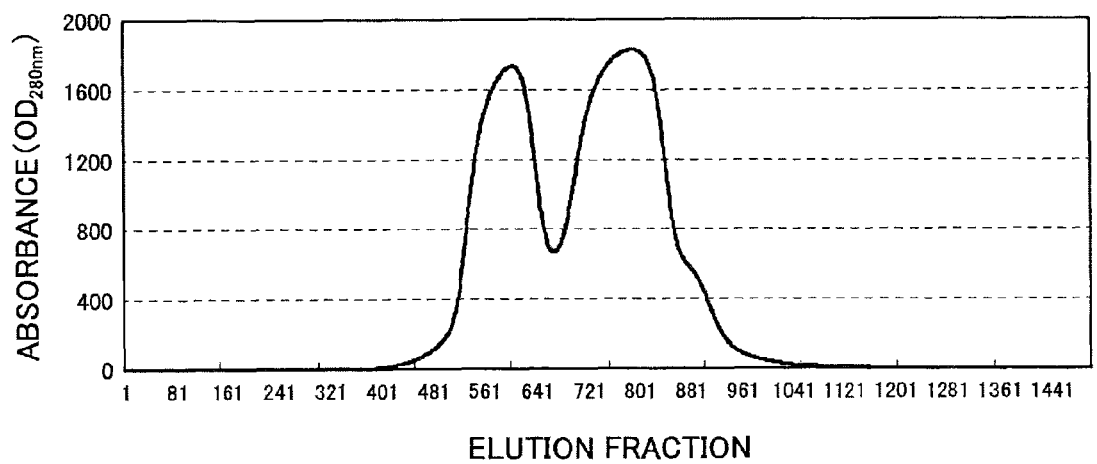
FIG. 1A is a graph illustrating the results from a first embodiment, illustrating the results from when the elution behavior of a protein resulting from ion exchange chromatography purification was analyzed with a absorbance at 280 nm, which is a measure of the protein concentration.

A more detailed description of the present invention shall be provided below.

The electrode having enzyme crystals immobilized thereon of the present invention is configured to include an electroconductive base material that can be connected to an external circuit, as well as an enzyme crystal that has been immobilized onto the electroconductive base material. In the enzyme crystal, enzyme molecules have been aligned in a state where regularity on the molecular level has been maintained, and thus the electrode having enzyme crystals immobilized thereon is such that the enzyme, which is the electrode catalyst, has been immobilized onto the surface of the electroconductive base material with a uniformly, high density, and constantly aligned orientation. More specifically, the enzyme can be immobilized at a density of 4,000 mg/cm$^2$ or higher; the amount of immobilization can be considerably increased in comparison to the maximum amount of immobilization in the prior art.

There is no particular limitation to the enzymes that can be used in the electrode having enzyme crystals immobilized thereon of the present invention, provided that the enzyme catalyst reaction and the electrode reaction can be successfully conjugated, and any enzyme whatsoever can be used. For example, it would be possible to use an oxidoreductase, a hydrolase, a transferase, or the like. Although there is no limitation thereto, it is preferable to use an oxidoreductase. An enzyme that is classified under the enzyme number (Enzyme Commission number) EC.1. according to the International Union of Biochemistry and Molecular Biology is one type of oxidoreductase that can be used. Examples include a dehydrogenase, oxidase, peroxidase, hydroxylase, oxygenase, reductase, or the like. More specific examples could include glucose oxidase, alcohol oxidase, aldehyde oxidase, lactic acid oxidase, cholesterol oxidase, sarcosine oxidase, fructosyl amine oxidase, pyruvic acid oxidase, glucose dehydrogenase, fructose dehydrogenase, alcohol dehydrogenase, aldehyde dehydrogenase, lactic acid dehydrogenase, pyruvic acid dehydrogenase, malic acid dehydrogenase, hydroxybutyric acid dehydrogenase, aldehyde reductase, glucose fructose oxidoreductase, fatty acid peroxidase, ascorbic peroxidase, catalase, and laccase and other multi-copper enzymes. There is also no particular limitation to whether or not a coenzyme is required; examples of coenzymes include nicotinic acid, riboflavin, and other coenzyme vitamins, or pyrroloquinoline quinone and other coenzyme quinones. Also, those enzymes that do require a coenzyme may be in the form of an apoenzyme or in the form of a holoenzyme. These enzymes can be used independently or in a combination of a plurality of enzymes. It would therefore be possible to construct a conjugated system by using the combination of, for example, any desired enzyme and any other desired enzyme conjugated to that enzyme.

Preferable examples include glucose dehydrogenases, such as pyrroloquinoline quinone (hereinafter abbreviated as "PQQ")-dependent glucose dehydrogenase, which requires PQQ as a coenzyme in terms of the expression of catalytic activity, as well as an NAD$^+$-dependent formaldehyde dehydrogenase, which requires nicotinamide adenine dinucleotide (NAD$^+$) in terms of the expression of catalytic activity. Particularly favorably, a glucose dehydrogenase from *Acinetobacter calcoaceticus* (GENBANK ACCESSION No.: 15871, Cleton-Jansen, A. M., Goosen, N., Vink, K. and van de Putte, P., et al. "Cloning, characterization and DNA sequencing of the gene encoding the Mr 50,000 quinoprotein glucose dehydrogenase from *Acinetobacter calcoaceticus*", Journal Mol. Gen. Genet., vol. 217, issue 2-3, pp. 430 to 436, 1989) could be used. This enzyme is present in the periplasmic fraction of the *Acinetobacter* bacterium and participates in energy production by transporting electrons obtained by oxidation over to the respiratory chain. The expression of this activity necessitates PQQ and calcium ions; in addition to participating in catalytic reactions, calcium ions are known to be related to homo-dimer formation. In comparison to other glucose oxidases, this enzyme is characterized by very fast reaction rates and by being less susceptible to the influence of dissolved oxygen, and thus the enzyme has a very high value of utility as an enzyme electrode. For this reason, the enzyme is widely used in self-monitored blood glucose meters, and is also expected to have applications as an enzyme catalyst for enzymatic fuel cells in which glucose is the fuel. In a case where a glucose dehydrogenase serves as an enzyme catalyst in a biological fuel cell, the glucose dehydrogenase preferably serves as the negative electrode-side catalyst, i.e., as the anode-side catalyst.

Preferably a laccase is used. "Laccase" is a generic name of phenol oxidases. These enzymes oxidize phenolic compounds as a substrate in the presence of oxygen. The enzymes are multi-copper oxidases, and are proteins that include in the molecule four copper atoms needed for enzyme activity. The enzymes use electrons removed from the substrate to catalyze reactions in which the electron reduction of molecular oxygen takes place and water molecules are generated. Examples of a substrate could include 2,2'-azinobis (3-ethylbenzothiazoline-6-sulfonic acid ammonium salt (hereinafter abbreviated as "ABTS"), N-ethyl-N-(2-hydroxy-3-sulfopropyl)-3-methylaniline (TOOS), dimethyl aniline, diethyl aniline, N,N-dimethyl-p-phenylenediamine, catechol, resorcinol, hydroquinone, phenol, guaiacol, pyrogallol, p-hydroxybenzoic acid, caffeic acid, hydrocaffeic acid, o-cresol, p-toluidine, o-chlorophenol, m-chlorophenol, p-chlorophenol, 2,4-dichlorophenol, 2,6-dichlorophenol, 2,4,6-trichlorophenol, 2,6-dimethoxyphenol, p-phenylenediamine, or propyl gallate. It is therefore possible to construct a biosensor for detecting phenolic compounds, by using a laccase as the electrode catalyst. Because electrons can be utilized to reduce oxygen, the value of utility as a positive electrode, i.e., cathode, of a biological fuel cell is very high. Laccases therefore are expected to have applications as enzyme catalysts for enzymatic fuel cells. Particularly favorably, a CotA laccase from *Bacillus subtilis* (Martins L O, et al., J Biol. Chem., 2002, vol. 277, no. 21, pp. 18849 to 18859 (Non-patent Document 1 of the Prior Art Documents), and Enguita F J, et al., Acta. Crystallogr. D. Biol. Crystallogr., 2002, 58 (Pt. 9), pp. 1490-1493 (Non-patent Document 2 of the Prior Art Documents)) can be used.

The origin of the enzyme is also not particularly limited. The enzyme therefore may be an enzyme from nature, prepared by a suitable protein isolation and purification technique from a naturally occurring bacterium, yeast, animal, plant, or any other organism, or may be an enzyme that has been produced by a genetic engineering technique as a recombinant protein or an enzyme that has been chemically synthesized.

In the present invention, preferably, a genetic recombination technique is used to acquire the enzyme as a recombinant protein. The amino acid sequences of many enzymes and the base sequences of the genes that encode the same are publicly known and can be acquired from GenBank, EMBL, DDBJ, and other gene sequence databases. A person skilled in the art would also be able to clone a desired enzyme gene on the basis of information on a base sequence. As one example, sequence information for the glucose dehydrogenase from *Acinetobacter calcoaceticus* described above (GENBANK ACCESSION No: 15871) is illustrated by SEQ ID NO: 1 (a base sequence) and SEQ ID NO: 2 (an amino acid sequence) in the sequence listing. It would also be possible to use SEQ ID NO: 3 (a base sequence) and SEQ ID NO: 4 (an amino acid sequence) presented therein. Sequence information on the CotA laccase from *Bacillus subtilis* is also illustrated by SEQ ID NO: 5 (a base sequence) and SEQ ID NO: 6 (an amino acid sequence) in the sequence listing. It would similarly also be possible to use SEQ ID NO: 7 (a base sequence) and SEQ ID NO: 8 (an amino acid sequence) presented therein.

More specifically, a nucleic acid molecule that encodes a desired enzyme from genomic DNA from an organism, cDNA synthesized by reverse transcription from total RNA, or the like can be prepared by hybridization using, as the probe, DNA prepared on the basis of the base sequence of a desired enzyme gene. The probe used herein is an oligonucleotide that includes a sequence complementary to the desired enzyme, and can be prepared on the basis of a conventional method. It would be possible to utilize, for example, a chemical synthesis technique based on a phosphoramidite method or the like, or, in a case where the nucleic acid being targeted has already been acquired, a restriction enzyme fragment thereof, or the like. One example of the probe of such description is an oligonucleotide that is a base sequence of a nucleic acid molecule that encodes a desired enzyme and is made of 10 or more consecutive bases, preferably 15 or more consecutive bases, even more preferably about 20 to 50 consecutive bases from the base sequence. The probe may also have an appropriate label attached thereto, as needed; examples of such a label include a radioisotope, a fluorescent dye, or the like.

PCR, which is used for a primer based on the base sequence of a desired enzyme gene, also similarly could be used to prepare a nucleic acid molecule that encodes the desired enzyme, using genomic DNA from an organism or cDNA as a template. The primer to be used in the case where PCR is utilized is an oligonucleotide that includes a sequence complementary to the nucleic acid sequence encoding the desired enzyme, and can be prepared on the basis of a conventional method. It would be possible to utilize, for example, a chemical synthesis technique based on a phosphoramidite technique or the like, or, in a case where the nucleic acid being targeted has already been acquired, a restriction enzyme fragment thereof, or the like. In a case where the primer is prepared on the basis of a chemical synthesis, the primer is designed on the basis of the sequence information of the target nucleic acid in advance of the synthesis. In the design of the primer, for example, support software for primer design or the like could be utilized so as to amplify a desired region. After synthesis, the primer is purified by HPLC or other means. In a case where chemical synthesis is carried out, it would also be possible to utilize a commercially available automated synthesis apparatus. The primer of such description is typified by an oligonucleotide made of 10 or more bases, preferably 15 or more, even more preferably about 20 to 50 bases and designed so that the desired amplification region is sandwiched therein.

The phrase "complementary" herein signifies that a probe or primer and a target nucleic acid molecular are able to specifically bind together according to the base-pairing rules to form a stable double-stranded structure. Not only is complete complementarity acceptable herein, but also partial complementarity, in which only some nucleic acid bases fit along the base-pairing rules, provided that the complementarity suffices for the probe or primer and the target nucleic acid molecule to be able to form a stable double-stranded structure. The number of bases must be of a length sufficient for specific recognition of the target nucleic acid molecule, but, conversely, excessive length is not preferable because a non-specific reaction is induced. The appropriate length is therefore determined depending on many factors, such as the guanine-cytosine (GC) content and other aspects of sequence information on the target nucleic acid, as well as the reaction temperature, salt concentration within the reaction solution, and other hybridization reaction conditions.

A conventional phosphoramidite method or other DNA synthesis could also be utilized to chemically synthesize a nucleic acid molecule that encodes the desired enzyme.

The resulting nucleic acid molecule can then be used to produce the desired enzyme through a genetic recombination technique, which would be known to a person skilled in the art.

More specifically, the nucleic acid molecule for encoding the desired enzyme is inserted into a suitable expression vector, which is then introduced into a host, whereby a transformant is prepared. There is no particular limitation to the vector that can be utilized herein, provided that foreign DNA can be integrated in and that autonomous replication in the host cell is possible. The vector therefore is one that includes at least one restriction enzyme site sequence that can be inserted into a foreign gene. For example, a plasmid vector (pEX series, pUC series, pBR series, and the like), a phage vector (λgt10, λgt11, λZAP, and the like) a cosmid vector, a viral vector (Vaccinia virus, Baculovirus, and the like), or the like is included therein. The vector may be integrated in so that the foreign gene is able to express a function thereof, and may include another known base sequence needed for functional expression. Examples include a promoter sequence, a leader sequence, a signal sequence, and a ribosome binding sequence. A promoter sequence is favorably typified by, for example, a lac promoter, trp promoter, or the like in a case where the host is *Escherichia coli* (*E. coli*). However, there is no limitation thereto, and a known promoter sequence can be utilized. It would also be possible to further include a marking sequence or the like whereby phenotypic selection can be imparted within the host. Such a marking sequence is typified by, inter alia, sequences that encode genes for drug-resistance, auxotrophy, and the like. More specifically, typical examples include a kanamycin resistance gene, chloramphenicol resistance gene, ampicillin resistance gene, and the like.

Although not limited hereto, the insertion of the foreign gene into the vector can be performed using, for example, a method for cutting a nucleic acid molecule that encodes a desired enzyme, with an appropriate restriction enzyme, and then inserting and ligating the nucleic acid molecule to a multi-cloning site or a restriction enzyme site of a suitable vector. A method for using a DNA ligase or another known method can be utilized in the ligation process. A commercially available ligation kit, such as the DNA Ligation Kit (Takara Bio), can also be utilized.

There is no particular limitation to the cell serving as the host in the process of preparing the transformant, provided that the host cell be capable of efficient expression of the foreign gene. A prokaryotic cell can be favorably utilized; in particular, *E. coli* can be utilized. Otherwise, it would also be possible to utilize *Bacillus subtilis*, bacteria of the genus *Bacillus*, bacteria of the genus *Pseudomonas*, or the like. Examples of *E. coli* that can be utilized include *E. coli* DH5α, *E. coli* BL21, *E. coli* JM109, and the like. Furthermore, there is no restriction to prokaryotes, but rather eukaryotic cells could also be utilized. Examples can include yeasts such as *Saccharomyces cerevisiae*, or Sf9 cells or other insect cells, or Chinese hamster ovary (CHO) cells, COS-7 cells, or other animal cells, and the like. A calcium chloride method, electroporation, liposome transfection, microinjection, or another known method can be utilized as the method for transformation.

The resulting transformant is subsequently cultured in a suitable nutritive culture medium under conditions permitting expression of the introduced nucleic acid molecule, to produce the desired enzyme. The culturing can be carried out according to a conventional method, and the culture conditions may be selected in consideration of the nutritive and physiological properties of the host cells. There is no particular limitation to the culture medium used, provided that the culture medium includes nutrients that can be assimilated and allows for efficient expression of the protein in the transformant. Therefore, preferably, the culture medium includes a carbon source, a nitrogen source, and other essential nutrients needed for growth of the host cells; no distinction in preference is made between a natural culture medium and a synthetic culture medium. Examples of a carbon source include glucose, dextrose, starch, or the like, and examples of a nitrogen source include an ammonium salt, a nitrate salt, an amino acid, a peptone, casein, or the like. As desired, an inorganic salt, a vitamin, an antibiotic, or the like could also be included as another nutrient. In a case where the host cells are *E. coli*, an LB culture medium, M9 culture medium, or the like can be favorably utilized. There is also no particular limitation to the form of culturing, but a liquid culture medium can be favorably utilized from the standpoint of large-scale culture.

The host cells for retaining the desired recombinant vector can be selected depending on, for example, whether or not there is expression of the marking sequence. In a case where, for example, a drug resistance gene is utilized as the marking sequence, it can be carried out by culturing in a culture medium containing the drug corresponding to the drug resistance gene.

To isolate and purify the desired enzyme from the culture of the transformant, an ordinary protein isolation and purification method can be used. For purification, a technique following a general method for isolating and purifying protein may be applied, in accordance with the fraction of the desired enzyme existing from the culture of the transformant. More specifically, in a case where the desired enzyme is produced outside the host cells, either the culture solution is used without modification, or the host cells are removed by centrifuge separation, filtration, or other means to obtain the culture supernatant. By then selecting as appropriate a known method for purifying protein for the culture supernatant, isolation and purification are possible. For example, ammonium sulfate precipitation, dialysis, SDS-PAGE electrophoresis, gel filtration, a variety of different methods of chromatography such as hydrophobic, anionic, cationic, or affinity chromatography, or another known technique of isolation and purification can be applied either independently or in combination as appropriate. Especially in a case where affinity chromatography is utilized, preferably, the desired enzyme is expressed as a fusion protein fused with a histidine tag (His-tag) or other tag peptide, to make use of the affinity thereof for the tag peptide. In a case where the desired enzyme is produced within the host cells, the host cells are recovered by subjecting the culture to centrifugal separation, filtration, or other means. The host cells are then disrupted by lysozyme treatment or another method of enzymatic cell disruption, by ultrasonic treatment, freeze-thawing, osmotic shock or another method of physical cell disruption, or the like. After cell disruption, the soluble fraction is collected by centrifugal separation, filtration, or other means. The resulting soluble fraction can then be treated in a manner similar with respect to the above-described case where production is possible outside the cell, to thereby carry out isolation and purification.

Enzymes for which the amino acid sequence is known can also be produced by a chemical synthesis technique. For example, preparation can also be performed by synthesizing all or part of the amino acid sequence of a desired enzyme and then reconstructing the resulting polypeptide under suitable conditions.

An enzyme used in the present invention may also be a variant obtained by artificially inducing a variation in an enzyme from nature. The enzyme may also be in a form where the enzyme has been modified by a variety of labeling compounds such as a fluorescent material or a radioisotope, or has been fused to another protein such as an antibody or a tag peptide.

The term "variant" herein signifies the inclusion of an amino acid sequence having a variant site where a specific amino acid of an enzyme from nature has undergone a variation. The term "variation" signifies the occurrence of a variation where one or a plurality of amino acids is/are deleted, substituted, inserted, and/or added, with respect to the amino acid sequence of the protein serving as the basis for variation. The phrase "a variation where one or a plurality of amino acids is/are deleted, substituted, inserted, and/or added" signifies the deletion, substitution, insertion, or addition of a number of amino acids that is within the scope of what can be deleted, substituted, inserted, or added by a known DNA recombination technique, method for introducing point mutations, or the like in a gene that encodes the protein serving as the basis for variation; the phrase also includes a combination thereof. For example, the variant of such description can share 70% homology or greater, preferably 80% or greater, even more preferably 90% or greater on the amino acid level with the amino acid sequences illustrated by SEQ ID NO: 2 or SEQ ID NO: 4.

The variant of such description can be prepared by utilizing a known technique for introducing a mutation. For example, it would be possible to utilize site-directed mutagenesis, PCR mutagenesis for utilizing PCR or the like to introduce a point mutation, or transposon insertion mutagenesis or another known technique of mutagenesis. A commercially available mutagenesis kit (for example, the QuikChange® Site-directed Mutagenesis Kit (Stratagene)) or the like may be utilized. The process can also be conducted by constructing a nucleic acid molecule for encoding an enzyme that has undergone a desired variation using a conventional phosphoramidite method or other DNA synthesis method, and the desired enzyme can be produced by the above-mentioned gene recombination techniques known to a person skilled in the art.

Preferably, an enzyme that has been purified to a high degree of purity is used in the process of enzyme crystallization. The enzyme is therefore purified according to need in advance of the crystallization. An ordinary protein separation and purification technique can be used to purify the enzyme; known techniques for separation and purification, e.g., liquid chromatography (gel filtration chromatography, ion exchange chromatography, isoelectric point chromatography, hydrophobic chromatography, or affinity chromatography) or, in a case where the protein intended to be purified is heat-resistant, a heat treatment, or the like can be applied, either independently or in combination as appropriate.

Preferably, in the process of crystallization, the enzyme is in a concentrated state; a concentration treatment is carried out as needed after purification. Although there is no restriction hereto, typical examples can include vacuum concentration, membrane concentration using an ultrafiltration membrane or the like, or a salt precipitation treatment with ammonium sulfate, sodium sulfate, or the like.

The enzyme is crystallized by altering the salt concentration, evaporation, temperature, pH, or precipitant concentration within a solution that has been supersaturated with the enzyme, to thereby cause the enzyme dissolved in the solution to be precipitated by the gradual decline in the degree of solubility thereof. Generally, the enzyme is crystallized by adding a precipitant for lowering the enzyme solubility to the enzyme solution; examples of precipitants that can be used include sodium chloride, ammonium sulfate, sodium phosphate, and other inorganic salts, or polyethylene glycol and other polymers, as well as 2-methyl-2,4-pentanediol, ethanol, isopropanol, and other organic compounds. As more specific means, any known technique can be used; examples that can be utilized include vapor diffusion, dialysis, a batch method, an interfacial diffusion method, or a temperature gradient method, and for vapor diffusion, it would be possible to utilize a hanging drop method, sitting drop method, sandwich drop method, or the like. In particular, the sitting drop method and hanging drop method are recognized among those skilled in the art as widely used techniques. Both are methods for sealing in a droplet of enzyme solution that includes a precipitant and a more highly concentrated precipitant solution and allowing same to stand within a single enclosed space in such a manner that the two are not in direct contact. Vapor equilibrium causes the water vapor generated thereby from the droplet of enzyme solution having a lower concentration of the precipitant to be gradually taken in by the highly concentrated precipitant solution; this causes a simultaneous elevation in the protein concentration and precipitant concentration within the droplet of enzyme solution, forming a supersaturated state and leading to crystallization. The distinction between the sitting drop method and the hanging drop method is made depending on the manner in which the droplets are allowed to stand, whereas the sitting drop method refers to a method for installing a droplet stand in the interior of an enclosed space and allowing a small droplet of enzyme solution to stand on the droplet stand and sealing in the enclosed space, while the hanging drop method refers to a method for suspending a droplet of enzyme solution from a glass plate at an upper part inside an enclosed space and sealing in the enclosed space.

The ideal conditions for crystallizing the enzyme are entirely different depending on the type of enzyme, and thus favorable conditions are selected and determined as appropriate in accordance with the type of enzyme intended to be immobilized. For example, in the case of PQQ-dependent glucose dehydrogenase from the *Acinetobacter calcoaceticus* strain, Oubrie A, Rozeboom H J, Kalk K H, Olsthoorn A J, Duine J A, Dijkstra B W. et al., "Structure and mechanism of soluble quinoprotein glucose dehydrogenase," EMBO J., 1999, vol. 18, no. 19, pp. 5187-5194, or Oubrie A, Rozeboom H J, Kalk K H, Duine J A, Dijkstra B W., et al., "The 1.7A crystal structure of the apo form of the soluble quinoprotein glucose dehydrogenase from *Acinetobacter calcoaceticus* reveals a novel internal conserved sequence repeat," J. Mol. Biol., 1999, vol. 289, no. 2, pp. 319-333 can be referenced. More specifically, a typical example could be conditions conforming to the conditions stated in Example 3. Furthermore, in the case of CotA laccase from *Bacillus Subtilis*, Enguita F J, et al., Acta. Crystallogr. D. Biol. Crystallogr., 2002, 58 (Pt 9), pp. 1490-1493 can be referenced. More specifically, a typical example could be conditions conforming to the conditions stated in Example 15. However, in the case of an enzyme for which favorable crystallization conditions have not been established, it is necessary to perform screening to search for the crystallization conditions. Examples of crystallization conditions for which optimization must be performed include the purity and concentration of the enzyme intended to be crystallized, the ionic strength, concentration, and temperature of the enzyme solution, the type of precipitant, and the like. The question of whether or not the conditions that have been investigated are favorable in terms of crystallizing the enzyme can be decided by investigating the outcome of the crystals, the size of the generated crystals, X-ray crystal structure analysis data, and the like. The size of enzyme crystal suitable for the electrode having enzyme crystals immobilized thereon of the present invention is preferably as large as possible, but ordinarily is 0.1 to 1 mm, particularly preferably about 0.5 to 1 mm. To screen for the crystallization conditions, it would also be possible to use a commercially available screening kit, such as Hampton's Crystal Screen Kit or Crystal Screen II Kit or the like. In the present invention, preferably, the enzyme crystal is prepared as an enzyme crystal that includes 40 to 70% water or another solvent; no distinction in preference is made between a monocrystal and a polycrystal. In the case of an enzyme that requires a coenzyme, it would also be possible to carry out crystallization in the form not only of an apoenzyme but also a holoenzyme.

As an electroconductive base material that can be used in the electrode having enzyme crystals immobilized thereon of the present invention, it is possible to use an electroconductive base material of graphite, glassy carbon, or other carbon materials; aluminum, copper, gold, platinum, silver, nickel, palladium, and other metals or alloys; $SnO_2$, $In_2O_3$, $WO_3$, $TiO_2$, and other electroconductive oxides; or similar conventionally known materials. The material may be configured to be a structure of one layer or of two or more layers. Also, to improve electroconductivity, the base material may be coated with the commercially available KETJENBLACK™ or another carbon black, or an activated carbon powder or other electroconductive carbon microparticles. The size, shape, and the like of the electroconductive base material are not particularly restricted, and can be adjusted as appropriate in accordance with the intended use. In particular, the electrode having enzyme crystals immobilized thereon of the present invention can be configured to be a microelectrode endowed with a smaller electrode surface area, on the micrometer order. Since microfabrication of the electrode provides high-speed response properties and enhanced sensitivity and otherwise makes it possible to go beyond the limitations of measurement thus far, electrochemical measurement using a microelectrode is garnering attention. In a microelectrode, unlike the surface diffusion in a conventional plate electrode, the profile of diffusion is (semi) cylindrical diffusion or (semi) spherical diffusion, and therefore the quantity of redox species being diffused per unit area is increased. For this reason, the mass transfer in the conventional diffusion-limited state fails to keep up with the electrode reaction, and the diffusion layer grows farther away over time. Therefore, the reaction fails to reach a steady state. By contrast, when a microelectrode is used, sufficient supply of the material becomes possible, and, depending on the shape thereof, a steady reaction will be exhibited. The electrode having enzyme crystals immobilized thereon of the present invention might be the only technique whereby a superconcentrated enzyme can be immobilized on a micro-sized region.

The immobilization of the enzyme onto the electroconductive base material can be carried out by a known method. A typical example is to coat the electroconductive base material with the enzyme crystal and thereafter cover the enzyme crystal with a polymer to immobilize the same. It would also be possible to utilize, inter alia, a packaging method for sealing the same with alginic acid, carrageenan, or another polysaccharide; an electroconductive polymer, a redox polymer, a photo-crosslinkable polymer, or another polymer having a meshwork structure; or a semi-permeable membrane such as a dialysis membrane, to immobilize the enzyme crystal. It is further possible to utilize a carrier binding method for immobilizing the enzyme crystal via physical adsorption, ionic bonding, or covalent bonding. Preferably, the enzyme crystal is covered with a hydrophilic polymer. These methods may be used in combination, and it is desirable to select as appropriate an enzyme immobilization method that is optimal for each of the respective enzyme crystals.

The enzyme can also be immobilized by being crystallized on the electroconductive base material. In, for example, the sitting drop method described above, using the droplet stand formed in the interior of the enclosed space as the electroconductive base material and allowing a small droplet of enzyme solution to stand on the electroconductive base material and sealing the same makes it possible to immobilize the enzyme on the surface of the electroconductive base material at the same time as the crystallization of the enzyme. This makes it possible to immobilize the enzyme crystal onto the electrode in such a fashion that the crystalline state will never be broken, and also possible to achieve uniformity in the orientation of the enzyme. Also, in the case of an enzyme that requires a coenzyme, immobilization would also be possible at the same time as crystallization in not only an apoenzyme state but also a holoenzyme state.

The enzyme is preferably immobilized in a holoenzyme state comprising a coenzyme in a case where an enzyme that requires a coenzyme or cofactor, such as pyrroloquinoline quinone (PQQ) or niacin (NAD, NADP), e.g., glucose dehydrogenase, alcohol dehydrogenase, or the like is used as the enzyme. However, the enzyme may also be immobilized in an apoenzyme state, the coenzyme then being supplied as a separate layer or, alternatively, in a dissolved state within a suitable buffer solution. Any other material required for expression of the catalytic activity of the enzyme may also be supplied as a separate layer or, alternatively, in a dissolved state within a suitable buffer solution.

By being configured as per the foregoing, the electrode having enzyme crystals immobilized thereon of the present invention makes it possible to immobilize an enzyme, which is an electrode catalyst, on the surface of an electroconductive base material with a uniformly, high density, and constantly aligned orientation. For this reason, the electrode having enzyme crystals immobilized thereon makes it possible to facilitate smooth electron transfer and possible to produce excellent electrode performance. In immobilization in a solution state in which the enzyme has been dispersed in a solvent, as in the prior art, the dispersibility is worsened when the enzyme concentration is heightened, and the result is that the enzyme is immobilized in an aggregated state on the surface of the electroconductive base material; a problem then emerges in that smooth progress of electron transfer in the electrode is impeded, giving rise to a decline in electrode performance. However, the electrode having enzyme crystals immobilized thereon in which the enzyme has been immobilized in a uniformly, high density, and constantly aligned orientation is intended to solve such problems. The electrode having enzyme crystals immobilized thereon of the present invention is the first technique whereby an enzyme can be high density immobilized in the form of functional molecule that has retained catalytic function. When enzyme molecules are cross-linked to each other by a multifunctional reagent, a higher degree of cross-linking correlates to strengthening of the bonds between enzyme molecules and an increase in stability, but at the same time, there is also known to be a decline in enzyme activity (Japanese Laid-open Patent Application No. 2007-236317). That is, the present invention makes it possible to immobilize an enzyme crystal while still in the form of a functional molecule, without the use of a cross-linking agent or the like that would be a cause of a decline in catalytic activity, and thereby makes it possible to produce excellent electrode performance. In particular, growing the crystal on the electrode makes it possible to immobilize the enzyme crystal on the electrode in such a fashion that the crystalline state will never be broken. The electrode having enzyme crystals immobilized thereon of the present invention therefore makes it possible to maintain high catalytic activity as an electrode catalyst, and thus can be favorably utilized in a biological fuel cell, a biosensor, or the like.

(Biological Fuel Cell of the Present Invention)

The electrode having enzyme crystals immobilized thereon of the present invention can be utilized in a biological fuel cell. The electrode having enzyme crystals immobilized thereon of the present invention has excellent electrode performance whereby electron transfer in the electrode can proceed smoothly. The utilization thereof makes it possible to generate electricity at high capacity and high output, and possible to construct a high-performance biological fuel cell that possesses very high power generation efficiency and has excellent durability. That is, proteins, which include enzymes, are more stable when in a crystalline state than when in a solution state, and thus a biological fuel cell that utilizes an electrode having enzyme crystals immobilized thereon possesses excellent durability. The biological fuel cell of the present invention is constituted of, for example, an anode pole (negative electrode) for carrying out an oxidation reaction and a cathode pole (positive electrode) for carrying out a reduction reaction, and is configured, as needed, to comprise an ion conductive material, which is an electrolyte layer for isolating the anode and the cathode from each other. In the present invention, therefore, the anode-side electrode is preferably configured to be an electrode that has immobilized thereon a crystal of an enzyme for catalyzing the oxidation reaction. The enzyme for catalyzing the oxidation reaction is preferably one that is capable of oxidizing a material that can serve as the fuel for the biological fuel cell, such as a sugar, alcohol, organic acid, amine, hydrogen, or inorganic compound; PQQ-dependent glucose dehydrogenase, which possesses very high catalytic activity, is particularly preferable. The configuration is such that a catalyst whereby oxygen, hydrogen peroxide, or another oxidizing agent can be reduced and electrons can be transferred is immobilized on the cathode-side electrode. In a case where an electrode having enzyme crystals immobilized thereon is utilized as the cathode-side electrode, preferable examples include pyruvate oxidase, laccase, and other multi-copper enzymes. CotA laccase from *Bacillus subtilis* is particularly preferable. Any material could be utilized as the electrolyte layer, provided that the material lacks electron transport capability and possesses ion conductivity.

As needed, an electron-transfer mediator for mediating the enzyme reaction and the electron transfer between the electrodes is used. The mediator may be a material selected as being ideal in accordance with the type of enzyme crystal being immobilized, and is not particularly limited. Typical examples include quinones, cytochromes, viologens, phenazines, phenoxazines, phenothiazines, ferricyanides, ferredoxins, ferrocenes, and derivatives thereof.

The enzyme is preferably immobilized on the electrode in a holoenzyme state comprising a coenzyme in a case where an enzyme that requires a coenzyme or cofactor, such as pyrroloquinoline quinone (PQQ) or niacin (NAD, NADP), is used as the enzyme. However, the enzyme may also be immobilized in an apoenzyme state, the coenzyme then being supplied as a separate layer or, alternatively, in a dissolved state within a suitable buffer solution. Any other material required for expression of the catalytic activity of the enzyme may also be supplied as a separate layer or, alternatively, in a dissolved state within a suitable buffer solution.

The biological fuel cell of the present invention has at least one from among the anode- and cathode-side electrodes configured to be an electrode having enzyme crystals immobilized thereon. The biological fuel cell is constituted of the anode pole (plus electrode) and the cathode pole (minus electrode), where the mechanism of the minus electrode is that electron movement takes place from the fuel to the electrode and the electrons therein are accepted at the plus electrode, whereby an electric current first begins to flow. For this reason, in a case where an electrode having enzyme crystals immobilized thereon is not used for one of the poles, the catalytic electric current value at that pole becomes the limit, and the efficacy in enhancing the performance of the biological fuel cell as the electrode having enzyme crystals immobilized thereon is lower in comparison to a case where both poles are an electrode having enzyme crystals immobilized thereon. It is therefore preferable from the standpoint of the performance of the biological fuel cell to have both poles be configured as an electrode having enzyme crystals immobilized thereon.

Adopting the configuration of such description allows for the enzyme crystal of the anode electrode side to oxidize the substrate, which is the fuel, and accept electrons. Methanol, ethanol, propanol, glycerol, and other alcohols; formaldehyde, acetaldehyde, and other aldehydes; glucose, fructose, and other saccharides; ketones; amines; fats; proteins; and the metabolic intermediate products thereof can be utilized as the fuel, which is selected in accordance with the substrate of the enzyme crystal being immobilized on the electrode. The electrons are delivered to the anode electrode either directly or by passing through the mediator adapted to be an intermediate for the enzyme reaction and the electron transfer between the electrodes. Delivery of the electrons to the cathode electrode by passing through an external circuit from the anode electrode generates an electric current. Meanwhile, ions generated on the anode electrode side pass through the electrolyte layer and move to the cathode electrode side, and react with the electrons that have passed through the external circuit and moved from the anode side, thus generating water.

In a case where an enzyme crystal of glucose dehydrogenase is immobilized and utilized as the electrode, the electric current response illustrated below can take place and generate an electric current.

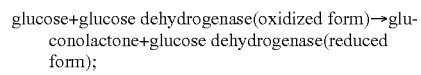

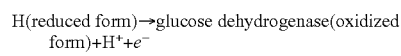

In a case where an enzyme crystal of laccase is immobilized and utilized as the electrode, the electric current response illustrated below can take place and generate an electric current. The reaction uses 2,2'-azino-bis(3-ethylbenzothiazoline-6-sulfonic acid) (ABTS) as a mediator.

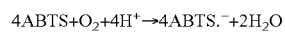

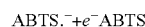

(Biosensor of the Present Invention)

The electrode having enzyme crystals immobilized thereon of the present invention can be utilized in a biosensor. The electrode having enzyme crystals immobilized thereon of the present invention has excellent electrode performance whereby electron transfer in the electrode can proceed smoothly, and the utilization thereof makes it possible to construct a biosensor that has high precision and excellent durability. The electrode having enzyme crystals immobilized thereon of the present invention can be utilized, for example, as an electrode of the biosensor, preferably as a working electrode thereof. The biosensor of the present invention may be configured in a two-electrode format, with the electrode having enzyme crystals immobilized thereon serving as the working electrode and with a counter electrode thereof provided as well; alternatively, from the standpoint of heightening the reliability of the measurement accuracy, the biosensor of the present invention may be configured to be a three-electrode format, to which a reference electrode of silver-silver chloride or the like is provided.

Measurement using the biosensor can be carried out by bringing a measurement sample into contact with the biosensor and detecting an electric current generated by the redox reaction between the substrate and the enzyme crystal immobilized on the electrode; this makes it possible to measure either the presence/absence of or concentration of the substrate within the sample. A known method can be utilized as the measurement method using the biosensor of the present invention, such as chrono amperometry, reduction current, or coulometry or cyclic voltammetry for measuring oxidation current.

In a case where glucose dehydrogenase is used as the electrode catalyst, the biosensor can be utilized to detect blood sugar levels and other forms of glucose detection, and in a case where laccase is used as the electrode catalyst, the biosensor can be utilized to detect phenolic compounds. It is possible to construct a biosensor having very high utility value, especially in fields such as medicine, food products, and the environment.

EXAMPLES

The present invention shall now be described in greater detail below by way of the examples, but the present invention is in no way limited to these examples. In particular, in the present examples, glucose dehydrogenase from *Acinetobacter* (examples 1 to 9) and CotA laccase from *Bacillus subtilis* (examples 10 to 20) are described by way of example as the electrode having enzyme crystals immobilized thereon, but the present invention is not limited thereto, and can be applied to enzymes derived from any species and having any physiochemical properties, provided that the catalytic activity thereof can be used conjugated to an electrode reaction.

Firstly, examples in which glucose dehydrogenase from *Acinetobacter* served as the catalyst of the electrode having enzyme crystals immobilized thereon shall now be described in examples 1 to 9.

Example 1

Construction of an Enzyme Expression System, Enzyme Synthesis Through an *E. coli* Protein Synthesis System, and Protein Purification In order to acquire a high-purity enzyme in the process of crystallization, a genetic engineering technique was used to produce an enzyme as a recombinant protein, which was then purified through a combination of a variety of different forms of chromatography. In particular for the process of crystallization, large quantities of purified enzyme are needed for screening to optimize the crystallization conditions.

Step 1: Construction of an Expression Vector for Glucose Dehydrogenase from *Acinetobacter*

A glucose dehydrogenase gene was acquired by amplification from *Acinetobacter calcoaceticus* purchased from the National Institute of Technology and Evaluation (NITE), and the sequence thereof served as the basis for rewriting of the sequence so that the amino acids would be the same as the amino acid sequence of *Acinetobacter calcoaceticus* gdhB gene for glucose dehydrogenase-B (GDH-B) (ACCESSION No.: 15871) registered in GenBank. The rewritten sequence was integrated into the restriction enzyme sites NdeI/BamHI in a pET-22b(+) vector, to serve as an expression plasmid. The plasmid was named pET-22b(+)-sGdh. The base sequence thereof is illustrated by SEQ ID NO: 3 in the sequence listing, and the amino acid sequence as estimated from the base sequence is illustrated by SEQ ID NO: 4 in the sequence listing.

Step 2: Expression of the Recombinant Protein by *E. coli*

The pET-22b(+)-sGdh was used to transform the *E. coli* strain BL21 (DE3), and the resulting colony was inoculated in 300 mL of the LB culture medium, Luria-Bertani culture medium which included 50 µg/mL ampicillin (hereinafter abbreviated as "LB/Amp culture medium"), and the colony was cultured overnight at 37° C. 20 L of LB/Amp culture medium was then placed in a jar fermenter, and 200 mL of the culture solution of *E. coli* prepared as described above was added thereto and cultured for about one hour until the absorbance of the culture solution was $OD_{600}=0.1$ at 37° C. Then, isopropyl-β-D-thiogalactopyranoside (IPTG) at a final concentration of 0.01 mM was added to induce synthesis of the recombinant protein, and the system was cultured overnight with shaking at 28° C. The culture solution was subjected to centrifuge separation and the supernatant was removed, whereafter the sediment (bacterial cells) was stored frozen at −80° C. until use in the following experimentation. The sediment was subjected to the following protein purification. The purification that was carried out was a combination of two types of enzyme purifications, namely, affinity chromatography (step 3), and an ion exchange chromatography (steps 3 and 4) that followed the charge characteristics of the protein.

Step 3: His-Tag Protein Purification by Affinity Chromatography

The protein expressed in step 2 was a His-tag fusion protein, and the protein was purified via the His-tag. The protein expression bacterial cells that had been stored frozen were suspended in a 25 mM potassium phosphate buffer solution, and a surfactant (0.4% BRIJ® 58) was added; the solution was allowed to stand for 30 minutes on ice. Next, an ultrasonic disruption treatment was carried out, and the bacterial cell suspension, once confirmed to no longer be viscous, was subjected to centrifuge separation (4° C., 40000×g, 30 minutes) and the supernatant was fractionated. Next, an open column was packed as appropriate with a metal affinity carrier (TALON®) for purifying His-tag fusion proteins, and pre-rinsed with 20 mM sodium phosphate, 5 mM imidazole, and 0.5 M NaCl solution, thus bringing the column into equilibrium. 0.5 M NaCl was then added to the supernatant after centrifuge separation, and the solution was applied to the column. Then, after rinsing with 20 mM sodium phosphate, 5 mM imidazole, and 0.5 M NaCl solution, the protein was eluted with 20 mM sodium phosphate, 500 mM imidazole, and 0.5 M NaCl solution. After elution, in order to remove the salts used in the elution (imidazole, NaCl, and the like), a buffer solution of 25 mM Tris-HCl (pH 7.4) served as an external solution for overnight dialysis.

Step 4: Protein Purification by Ion Exchange Chromatography

The protein solution acquired in step 3 described above was further purified using ion exchange chromatography that followed the charge properties of the protein.

Chromatographic Carrier Specification
Carrier: RESOURCE S (GE-Healthcare)
Column size: 0.46×10 cm
Bed volume: 1.7 ml
Charged group: Negative electrification (—O—$CH_2$—CHOH—$CH_2$—O—$CH_2$—CHOH—$CH_2$—$SO_3$—)
Binding capacity: 25 mg/column
Recommended flow rate: 6 mL/minute In the purification by RESOURCE S, 25 mM monopotassium phosphate (pH 7.4) and 1 mM EDTA served as a base buffer solution for rinsing the carrier and bringing the same to equilibrium. Next, the enzyme solution acquired in step 3 was applied to the column, and the protein was adsorbed onto the carrier, following which the carrier was rinsed with the above-described base buffer solution and impurities were removed. Next, the base buffer solution served as an initiating buffer solution for eluting the protein using a salt concentration gradient of 0 to 500 mM KCl. More specifically, elution was carried out under the following conditions.

Elution Buffer Composition
Buffer solution A: 25 mM monopotassium phosphate ($K_1H_2PO_4$), 1 mM EDTA
Buffer solution B: 25 mM monopotassium phosphate ($K_1H_2PO_4$), 1 mM EDTA, 1M KCl The absorbance at 280 nm, which a measure of the enzyme concentration, was measured with a spectrophotometer for each of the elution fragments, and the elution fraction was subjected to SDS-polyacrylamide (SDS-PAGE) electrophoresis and the elution behavior of the protein was analyzed.

Figure 1B:
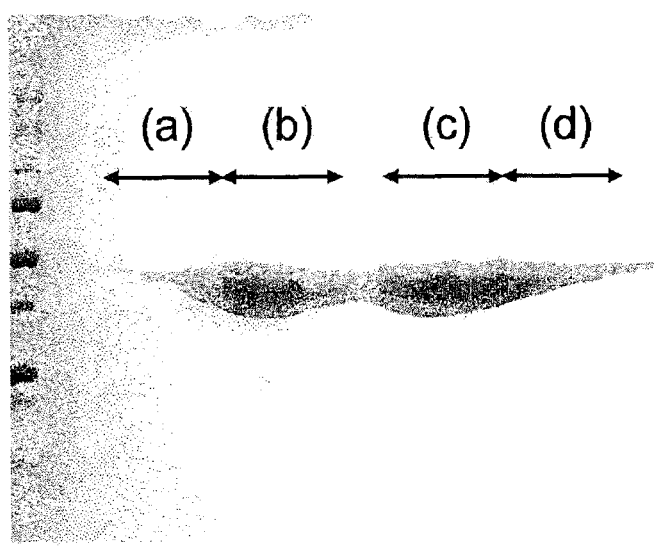
FIG. 1B is an electrophoresis diagram illustrating the results of the first embodiment, illustrating the results from when the elution behavior of the protein resulting from ion exchange chromatography purification was analyzed with SDS-PAGE electrophoresis.

The results are shown in FIG. 1. FIG. 1A is a diagram plotting the absorbance at 280 nm in each of the elution fractions, and FIG. 1B illustrates the results of electrophoresis of each of the elution fractions. In FIG. 1, the segments (a), (b), (c), and (d) are the collected fractions of the enzyme solutions eluted at a KCl concentration of 100 to 105 mM, 105 to 110 mM, 115 to 130 mM, and 130 to 150 mM, respectively. As a result, a signal indicative of the elution of the protein was detected at an early stage of elution (a KCl concentration of approximately 100 mM), and a broad signal of contaminants was detected in the latter half of elution. The protein signals were primarily divided into two peaks, which can be inferred to be triggered by some factor relating to the three-dimensional structure of the enzyme.

Next, in order to remove the KCl used in the elution of the protein, the protein purified herein underwent overnight dialysis using 25 mM Tris-HCl (pH 7.4) as a buffer solution and 1 mM EDTA as an external solution.

Example 2

Purity Assay of the Purified Enzyme

In the present example, the question of whether the purified enzyme acquired in example 1 was the high-purity enzyme needed for crystallization was checked. More specifically, this check was carried out by quantifying the enzyme present in the protein solution that was purified by affinity chromatography in example 1, as well as the enzyme present in the protein solution that was purified through the combination of affinity chromatography and ion exchange chromatography. A fraction equivalent to the region in segment (c) in FIG. 1B was used as the sample purified by the combination of affinity chromatography and ion exchange chromatography.

First, the eluted protein was confirmed in advance of the quantification. The protein solutions following the purifications described above underwent SDS-PAGE electrophoresis, which was followed by staining with the protein staining agent Flamingo Fluorescent Gel Stain (Bio-Rad), and band visualization using a fluoro-imaging analyzer FLA-3000 (Fuji Film).

Figure 2:
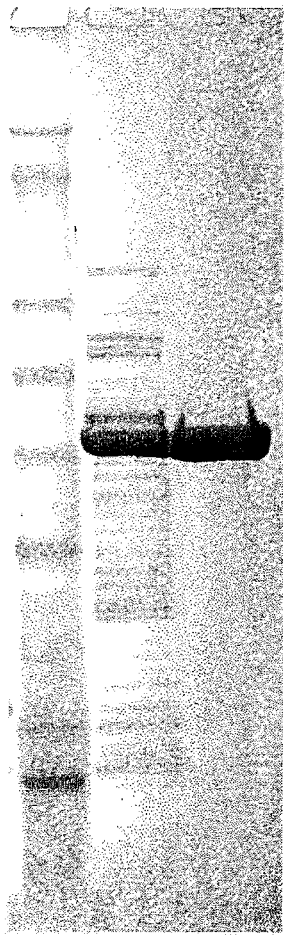
FIG. 2 is an electrophoresis diagram illustrating the results from a second embodiment, in which the enzyme purity was compared using SDS-PAGE electrophoresis between a case where purification was performed with affinity chromatography alone and a case where purification was performed with a combination of affinity chromatography and ion exchange chromatography.

The results are shown in FIG. 2.

In FIG. 2, lane 1 shows results from the enzyme purified with only affinity chromatography, and lane 2 shows the results from the enzyme purified with the combination of affinity chromatography and ion exchange chromatography. These results provided confirmation that substantially all contaminants had been removed by the purification by the combination of affinity chromatography and ion exchange chromatography.

Next, in order to quantify the purity, the concentration in the full-signal region of each of the lanes and in only the enzyme signal region was measured. More specifically, in regard to the signal strength of the protein band on the gel as visualized with the FLA-3000, the full signal (the strip-shaped region spanning from the position where sample migration started until the distal end of migration) and the enzyme signal (only the enzyme signal portion) were converted to a numerical value using the dedicated included software. The results are shown in Table 1.

TABLE 1

|  | Lane 1<br>Affinity chromatography<br>purification only | Lane 2<br>Affinity chromatography<br>purification + ion exchange<br>chromatography purification |
| --- | --- | --- |
| Full signal | 1356 | 2064 |
| Enzyme signal | 2427 | 2081 |
| Purity | 1356/2427 × 100 = 55.9% | 2064/2081 × 100 = 99.2% |

These results provide confirmation that a high-purity enzyme solution from which substantially all contaminants had been removed was obtained by purifying through the combination of affinity chromatography and ion exchange chromatography. The specific activity of the enzyme in segment (c) of FIG. 1B was 4,200 unit/mg.

Example 3

Screening for Enzyme Crystallization Conditions, and Crystallization of the Enzyme In the present example, an investigation for the purpose of crystallizing the enzyme purified in example 1 was conducted. A fraction, equivalent to the region in segment (c) in FIG. 1B, of the enzyme acquired in example 1 was used as the target of crystallization, and the crystallization was carried out by the vapor diffusion method. The reason for which segment (c) in FIG. 1B was selected is that when the stability of the enzyme precipitant solution in the buffer solution composition (50 mM Tris-HCl (pH 9.3), 120 mM NaCl, 3 mM $CaCl_2$) was compared on the basis of fractions equivalent to the regions in segments (b) and (c) in FIG. 1B, it was demonstrated that segment (b) had slightly lower stability in storage of several days or longer. For this reason, segment (c), which was preferable also on the basis of the quality and quantity of the enzyme, was selected as being intended for crystallization.

First, in order to ascertain the conditions whereby the crystals would precipitate, screening for crystallization conditions was conducted by referring to the crystallization conditions set forth in the documents (Oubrie A, Rozeboom H J, Kalk K H, Olsthoorn A J, Duine J A, Dijkstra B W. et al., "Structure and mechanism of soluble quinoprotein glucose dehydrogenase", EMBO J., 1999, vol. 18, no. 19, pp. 5187-5194, and Oubrie A, Rozeboom H J, Kalk K H, Duine J A, Dijkstra B W., et al., "The 1.7A crystal structure of the apo form of the soluble quinoprotein glucose dehydrogenase from *Acinetobacter calcoaceticus* reveals a novel internal conserved sequence repeat", J Mol. Biol., 1999, vol. 289, no. 2, pp. 319-333) disclosed with respect to methods for producing an enzyme crystal in order to analyze the three-dimensional structure of soluble PQQ-dependent glucose dehydrogenase from *Acinetobacter calcoaceticus*, toward which the present examples are directed.

More specifically, enzyme solution and precipitant solution were mixed on a 4 µL reaction scale. At this time, the enzyme concentration was set to 7.5, 10, 12.5, and 15 µg/µL, and 19, 20, 21, 22, 23, and 24% polyethylene glycol was used as the precipitant component. The precipitant solution was prepared by admixing polyethylene glycol, which is the above-mentioned precipitant component, into a buffer solution composition of 50 mM Tris-HCl (pH 9.3), 120 mM NaCl, and 3 mM $CaCl_2$. Next, droplets of the mixed solution of the enzyme solution and the precipitant solution were prepared on a silicone-coated cover glass. The cover glass piece was subsequently turned over, the droplet pit was covered with the glass piece, and crystallization was carried out by the vapor diffusion method. After the system was allowed to stand for seven days in an incubator at 30° C., the presence or absence of crystal deposition was observed under microscope (400× magnification).

The result was that transparent, membranous solid matter was observed, as were identically transparent microcrystals (about 0.02 mm); the membranous solid matter was inferred to be an enzyme that had aggregated into a film form. One enzyme crystal (about 0.1 mm) was also confirmed under conditions of low enzyme concentration (enzyme concentration 7.5 µg/µL, polyethylene glycol 21%), but three-dimensional crystal growth could not be confirmed. The enzyme concentration was therefore too high in the reaction conditions of the present experiment, and thus three-dimensional crystal growth could not take place; the enzyme was believed to have either taken a membranous form or to have ceased growth at being microcrystalline.

In view of the foregoing experimental results, the enzyme concentration was lowered to 0.5, 1, 2, and 3 µg/µL, and the polyethylene glycol concentration was set to 20, 21, and 22% for re-screening. Similarly with respect to the description above, after the system was allowed to stand for seven days at 30° C., the present or absence of crystal deposition was observed under microscope (400× magnification).

The result was that a plurality of enzyme crystals (about 1.0 mm) were confirmed. In greater detail, crystal about 0.1 mm large was confirmed to have formed at an enzyme concentration of 0.1 to 0.5 µg/µL, crystal about 0.5 mm large was confirmed to have formed at an enzyme concentration of 1 to 2 µg/µL, and crystal about 1 to 5 mm large was confirmed to have formed at an enzyme concentration of 3 to 4 µg/µL.

Figure 3A:
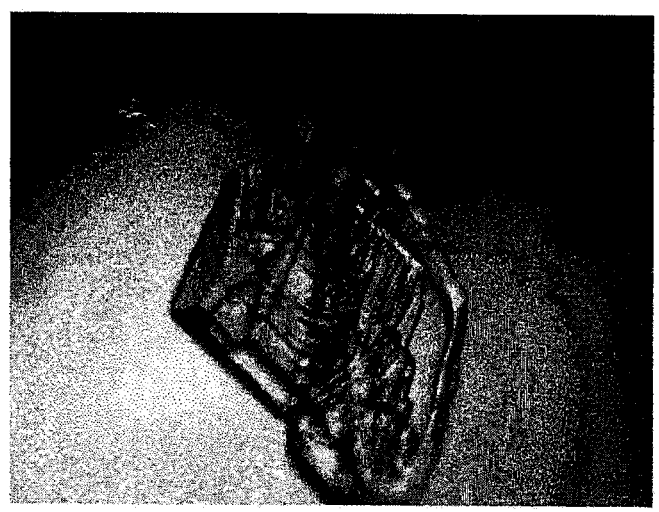
FIG. 3A is a photograph illustrating an enzyme crystal (a crystal aggregate) prepared in a third embodiment.
Figure 3B:
FIG. 3B is a photograph illustrating an enzyme crystal (a single crystal) prepared in a third embodiment.

These observed results demonstrated that an aggregate of large crystals as illustrated in FIG. 3A could form at heightened enzyme concentrations (3 to 4 µg/µL), and that at low enzyme concentrations (1 to 2 µg/µL), high quality single crystals suitable for a structural analysis such as X-ray analysis as illustrated in FIG. 3B could form. In view of the foregoing results, the crystallization conditions were determined as per Table 2 to serve as the conditions whereby enzyme crystals of about 0.5 mm, optimal for utilization in the present invention, could be formed.

TABLE 2

| Precipitant concentration (%) (Polyethylene glycol 6000) | 20 |
|---|---|
| Enzyme concentration (µg/µL) | 1-2 |
| Buffer solution pH | 9.3 |

Figure 4A:
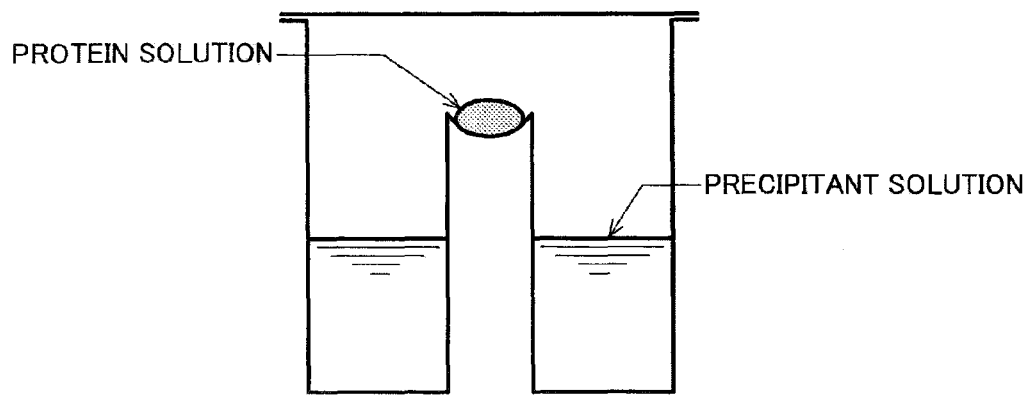
FIG. 4A is a drawing schematically illustrating a device for carrying out a crystallization reaction by a sitting drop technique in the third embodiment.
Figure 4B:
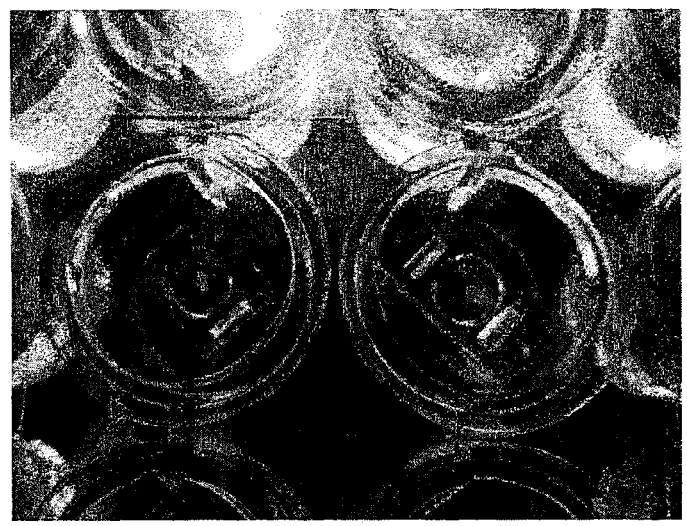
FIG. 4B is a photograph illustrating the manner in which the crystallization reaction by the sitting drop technique implemented in the third embodiment proceeded.

Next, in order to scale-up the reaction, a crystallization reaction was carried out with the "sitting drop method" which is one method of vapor diffusion. This made it possible to scale-up the reaction five-fold from 4 µL to 20 µL. FIG. 4A illustrates a schematic view of the sitting drop method as implemented herein; FIG. 4B illustrates a photograph illustrating the manner in which the crystallization reaction was actually carried out. For further description, the mechanism was one in which a chair, which is a container designed for the enzyme solution to be able to sit atop the liquid layer of the precipitant solution, was placed within a sealed container, and the crystals were grown thereon. In order to scale-up the reaction, the reaction time for crystallization was extended to be 20 days within the incubator at 30° C. Similarly with respect to the description above, the present or absence of crystal deposition was observed under microscope (400× magnification).

Figure 4C:
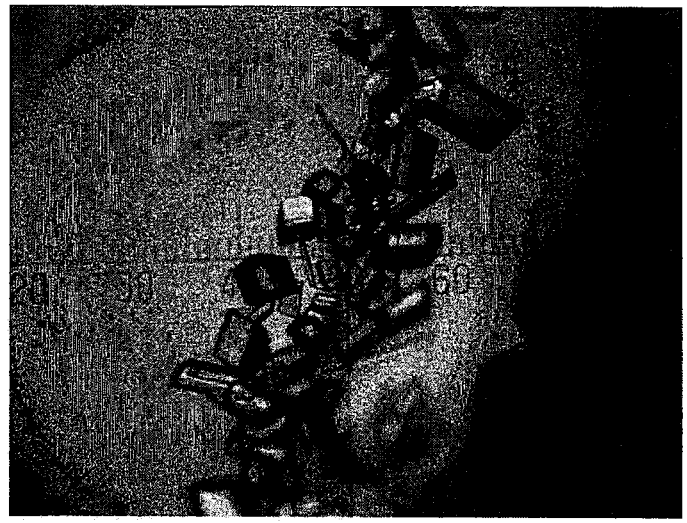
FIG. 4C is a photograph illustrating an enzyme crystal formed by the crystallization reaction by the sitting drop technique implemented in the third embodiment.

The results are shown in FIG. 4C. The results confirmed the formation of a monocrystal about 0.5 to 1.0 mm in size under the present conditions. This demonstrated that enzyme crystals suitable for utilization in order to construct the electrode having enzyme crystals immobilized thereon of the present invention could be acquired.

Example 4

Comparison of the Protein Concentrations in the Enzyme Crystals

In the present example, the protein concentration included in the enzyme crystals obtained by the sitting drop method in example 3 was compared against the amount of enzyme that can be present as a solution state.

Figure 5A:
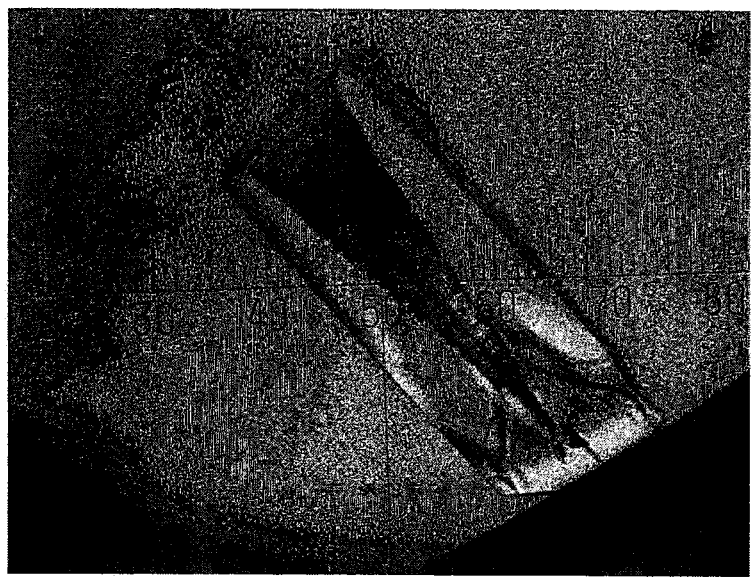
FIG. 5A is a microscopy image of one enzyme crystal used in order to measure the amount of enzyme in an enzyme crystal in a fourth embodiment.

One enzyme crystal obtained in example 3 was separated from the crystallization reaction solution. The separation of the crystal involved using a special paper string (Hampton Research) to suck the liquid portion out from the crystallization reaction solution, and thereafter employing a special crystal picker (Hampton Research) to pick out the crystal under a microscope. FIG. 5A illustrates the microscope observation image of the one enzyme crystal. The enzyme crystal that was separated out from the crystallization reaction solution was dissolved into 20 µL of a 50 mM Tris-HCl buffer solution (pH 7.4), thus forming an enzyme crystal solution.

The amount of enzyme included in the enzyme crystal solution was then measured and the amount of enzyme included within the enzyme crystal was calculated. The absorbance at 280 nm, which is a measure of the protein concentration, was measured by spectrophotometer, and the amount of enzyme was calculated at a molar extinction coefficient of $\epsilon=67,420$, and with a molecular weight MW=53,665. It was demonstrated through calculation that the enzyme crystal included the enzyme at a concentration of 4,000 $mg/cm^3$. Also, on the basis of the gauge present in the field of view of the microscope, the length, width, and height of the crystal were measured for an approximate estimate of the volume. The amount of enzyme when included in a solution of enzyme equivalent to the volume of the crystal and the amount of enzyme in the enzyme crystal were compared. The amount of enzyme included in the enzyme solution was compared as a concentration of 40 mg/mL. As to the reason for selecting the value of 40 mg/mL: the fact that precipitation takes place when the concentration is greater than 50 mg/mL in cases where the PQQ-dependent glucose dehydrogenase from *Acinetobacter calcoaceticus* used herein is in a solution state leads to 40 mg/mL being the maximum concentration that can be present as a solution state. This result demonstrated that about 100 times as high a concentration of enzyme can be included by using an enzyme crystal in comparison to the case of a solution state.

Next, the amount of enzyme included in the enzyme crystal and the amount of enzyme included in the enzyme solution in a solution state were compared by electrophoresis. More specifically, a part of the enzyme crystal solution prepared as described above was subjected to 12.5% acrylamide gel electrophoresis, and the protein bands were visualized by staining with Coomassie Brilliant Blue (CBB). For the purposes of comparing and contrasting, a solution of enzyme equivalent to the volume of the crystal was also similarly subjected to electrophoresis. At this time, the concentration of the solution of enzyme was 40 mg/mL, as stated above.

Figure 5B:
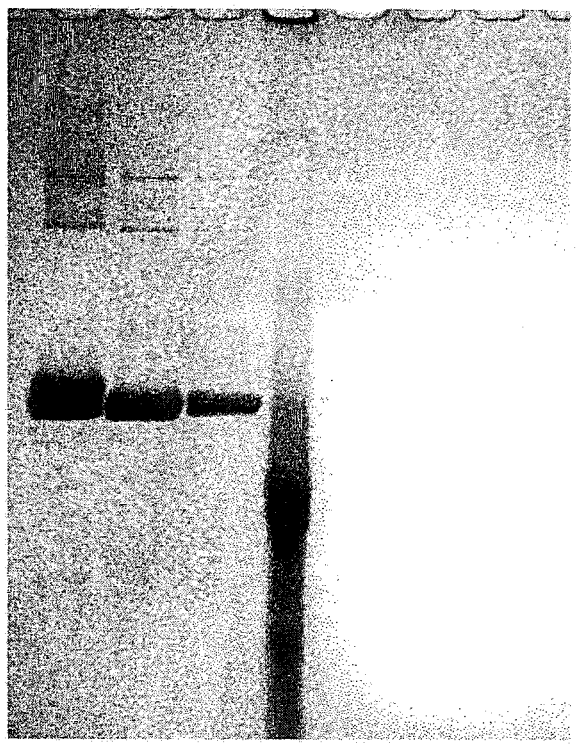
FIG. 5B is an electrophoresis diagram illustrating the results from the fourth embodiment, from when the amount of enzyme in the enzyme crystal and the amount of enzyme in a maximally concentrated enzyme solution were compared in acrylamide gel electrophoresis.

The results are shown in FIG. 5B.

In FIG. 5B, lane 1 illustrates the results of migration of the stock solution of the solution of enzyme crystal prepared as described above, lane 2 illustrates the results of migration of one-half the amount of stock solution in lane 1, and lane 3 illustrates the results of migration of one-fourth the amount of stock solution in lane 1. Lane 4 illustrates the results of migration of enzyme solution concentrated at 40 mg/mL, by way of comparison; lane 5 illustrates the results of migration of one-half the amount of enzyme solution in lane 4, and lane 6 illustrates the results of migration of one-fourth the amount of enzyme solution in lane 4. Similarly with respect to the comparison by calculation described above, these results, too, demonstrate that the enzyme crystal includes the enzyme at vastly higher concentration in comparison to the enzyme solution.

Example 5

Preparation of the Electrode Having Enzyme Crystals Immobilized Thereon

In the present example, utilization as an electrode catalyst of a biological fuel cell was assumed, and in order to prepare the electrode having enzyme crystals immobilized thereon, a method for immobilizing the enzyme crystal onto an electroconductive base material was investigated.

To immobilize the enzyme crystal onto the electroconductive base material, a method for using a photo-crosslinkable polymer was selected. More specifically, an enzyme immobilization kit (Toyo Gosei) was used to implement the method in accordance with the standard protocol included with the kit (in which is disclosed a procedure for preparing an electrode having soluble PQQ-dependent glucose dehydrogenase immobilized thereon). The enzyme immobilization kit is an experimental kit that is ideal for the early stages of investigating biosensors for electrochemical detection. The enzyme-immobilizing polymer BIOSURFINE® included with the kit was used as an immobilization material to prepare an electrode having enzyme crystals immobilized thereon obtained by immobilizing enzyme crystal onto an electroconductive base material.

A more detailed illustration of the specific procedure is provided below. Firstly, the enzyme crystal was treated so as to be converted to the holoenzyme form, in order to bind PQQ, the coenzyme needed for expression of enzyme activity. The enzyme crystal acquired in the present example is an apoenzyme and, in order to be converted into the active-form enzyme, must be subjected to treatment so as to be converted to a holoenzyme, in which the PQQ is incorporated thereinto; thus, PQQ solution was added to the solution in which the enzyme crystal obtained in example 3 was formed, so that the final concentration would be 0.1 mM, and the solution was allowed to stand for 30 minutes at room temperature, whereby the enzyme was converted to the holoenzyme form. It would, however, also be possible to carry out the crystallization in the form of a holoenzyme to which PQQ is bound, after the PQQ has been added to the enzyme solution and holoenzyme conversion treatment has been carried out. Then, after the holoenzyme conversion treatment, a special paper string was used to suck the liquid portion out from the crystallization reaction solution, leaving about 10 µL, to concentrate the crystal. The entire concentrated crystal solution was added in a dropwise fashion to the surface of the electroconductive base material (2.5 mm$^2$ of an electrode surface, in the form of a flat plate), and a paper-string filter was used to completely suck up the liquid portion. A carbon electrode (a three-electrode print electrode) was used as the electroconductive base material on which the enzyme was to be immobilized. Next, 5 µL of a polymer solution that had been diluted to 2% was added in a dropwise fashion to the electroconductive base material, which was then dried and thereafter exposed to UV light for five minutes to immobilize the enzyme crystals.

Although the polyethylene glycol used in the process of crystallization is included in the enzyme crystal, this will not hinder the immobilization, because polyethylene glycol has the property of neither mixing nor reacting with BIOSURF-INE®, the enzyme-immobilizing polymer.

The enzyme immobilization polymer and carbon electrode used herein are a disposable printed electrode (a disposable electrochemical printed chip (DEP-Chip), made by a venture company of the Japan Advanced Institute of Science and Technology; performance comparable to that of a glassy carbon electrode) intended for research and development, such as for enzyme activity measurement and other forms of electrochemical measurement and biosensing.

Example 6

Catalytic Function Assessment of the Enzyme Crystal Immobilized on the Electroconductive Base Material-1

The present example is a catalytic function assessment of the electrode having enzyme crystals immobilized thereon prepared with the procedure of example 5 by immobilizing the earlier-crystallized enzyme crystal on the electroconductive base material.

Figure 6A:
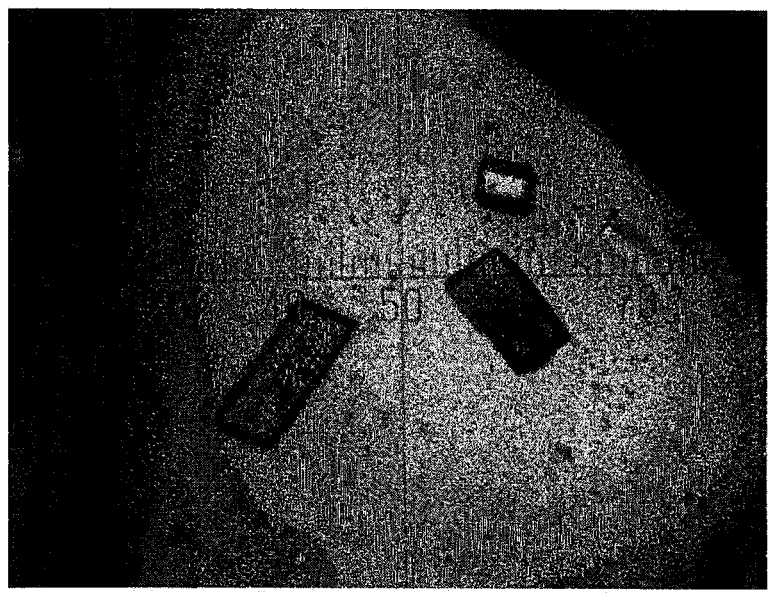
FIG. 6A is a microscopy image of an enzyme crystal used in order to prepare an electrode having enzyme crystals immobilized thereon in a sixth embodiment.

An electrode on which the enzyme crystal was immobilized on the electroconductive base material was prepared following the procedure in example 5. FIG. 6A illustrates a microscope image of the enzyme crystal used for the actual immobilization in the present example. The enzyme crystal is the one that was formed in example 3. It will thus be appreciated that the crystal includes many crystals, not only of a three-dimensional orientation, but also of a film-like form grown in a two-dimensional orientation as well as microcrystals. Next, the crystal was used to measure the electric current response associated with the oxidation reaction of glucose, which is the substrate of the enzyme, with a three-electrode electrochemical measurement system using an external power source (a potentiostat).

More specifically, the electrode having enzyme crystals immobilized thereon prepared by following the procedure in example 5 was used as the working electrode, a carbon electrode was used as the counter electrode, and a silver-silver chloride electrode was used as the reference electrode. The three electrodes were immersed in a reaction mixture solution (25 mM phosphoric acid buffer solution (pH 7.4), 0 or 100 mM glucose, and 1 mM 1-methoxy-5-methylphenazinium methylsulfate (mPMS)), and the constant potential at a constant voltage of 0.1 V (vs the silver/silver chloride electrode) was measured (a measurement of the electric current in the oxidation-reduction potential of the mPMS). Because mPMS was being used as the electron-transfer mediator, the constant potential electrolysis potential was set to +0.1 V from the standard oxidation-reduction potential of mPMS (+0.063 V). The so-constructed electrode having enzyme crystals immobilized thereon was used to measure the electric current response under conditions of 0 mM and 100 mM glucose concentration, by a chrono amperometry method (a measurement of the change in electric current over time by voltage clamp; hereinafter in some cases abbreviated as "CA").

Figure 6B:
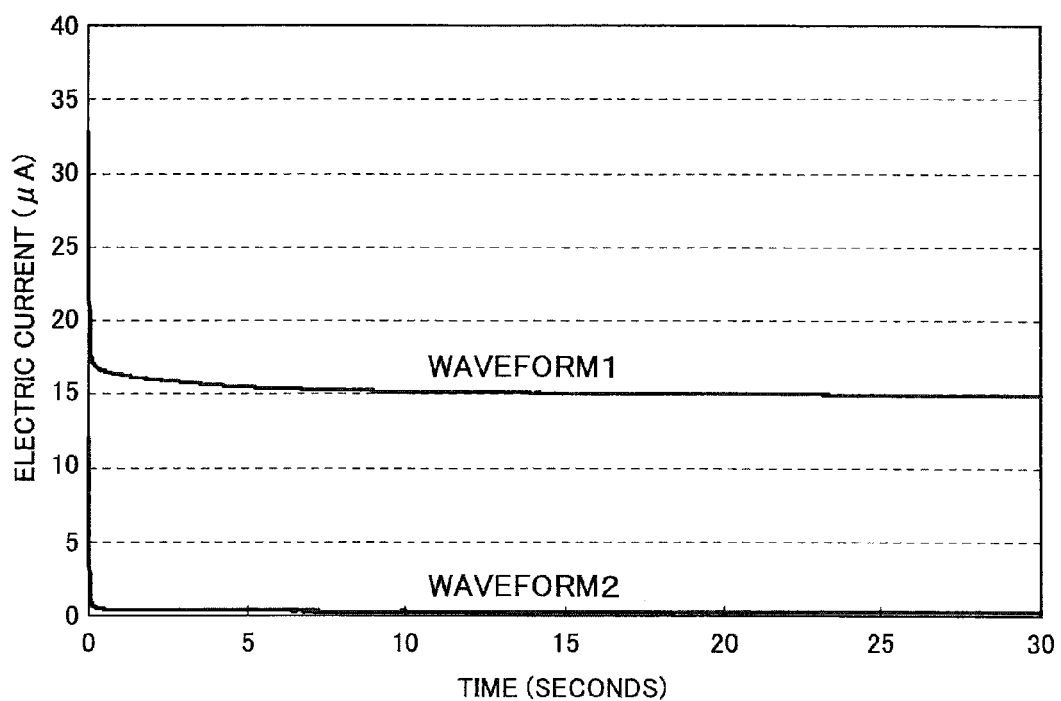
FIG. 6B is a graph illustrating the changes over time in a response value of a catalytic electric current with respect to glucose in the electrode having enzyme crystals immobilized thereon prepared in the sixth embodiment.

The results are shown in FIG. 6B. Waveform 1 illustrates the results under conditions of 100 mM glucose concentration, and waveform 2 illustrates the results under conditions of 0 mM glucose concentration, i.e., in a reaction mixture solution that contains no glucose. In view of these results, an electric current value (waveform 1) of 15 µA (after 30 seconds) was obtained under the conditions of 100 mM glucose concentration. By contrast, the electric current value was very close to 0 in the case where no glucose was included. This confirms, since an electric current value was obtained dependent on the glucose, that the electrode having enzyme crystals immobilized thereon prepared herein functions as an enzyme catalytic function electrode.

Potentiostat CA Measurement Conditions
Init. E (V)=0 (open circuit voltage),
High E (V)=+0.1,
Low E (V)=0,
Init. P/N=N,
Step=1,
Pulse Width (sec)=30
Sample Interval (s)=0.01,
Quiet Time (sec)=5

Example 7

Catalytic Function Assessment of the Enzyme Crystal Immobilized on the Electroconductive Base Material-2

The present example is a catalytic function assessment of an electrode having enzyme crystals immobilized thereon prepared by carrying out the crystallization reaction of the enzyme on the surface of the electroconductive base material.

An electrode having enzyme crystals immobilized thereon was prepared by carrying out the crystallization reaction of the enzyme atop the electroconductive base material. This electrode was compared against the electrode having enzyme crystals immobilized thereon prepared in example 6, in which the advance prepared enzyme crystal was immobilized on the electroconductive base material, to validate the possibility that running the crystallization reaction of the enzyme on the electroconductive base material makes it possible to prepare an electrode having excellent electrode function.

Instead of the chair on which the enzyme solution would be placed in the enzyme crystallization reaction by the sitting drop method implemented in example 3, the electroconductive base material was put in place, and the enzyme crystallization reaction was carried out on the surface thereof.

Figure 7A:
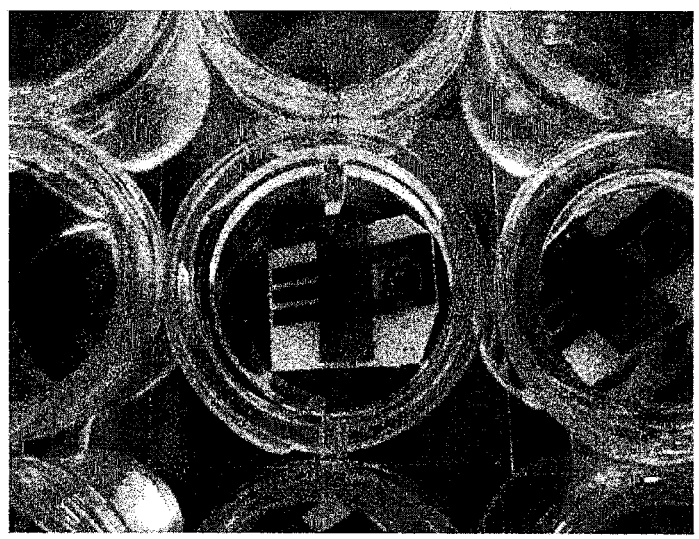
FIG. 7A is a photograph illustrating the manner in which the crystallization reaction by the sitting drop technique implemented in the seventh embodiment on the surface of an electroconductive base material proceeded.

FIG. 7A illustrates the manner in which the crystallization reaction of the enzyme was carried out on the electroconductive base material serving as the electrode. The electroconductive base material used herein is a carbon electrode that was printed onto a film, which can be finely processed. For this reason, an advantage emerges in that the crystallization conditions of the sitting drop method described in example 3 can be employed without alteration.

Figure 7B:
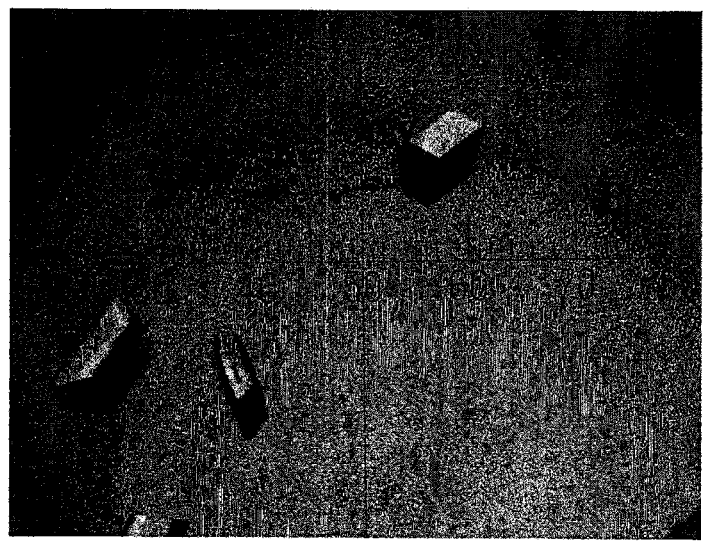
FIG. 7B is a microscopy image of an enzyme crystal that formed on the electroconductive base material prepared in the seventh embodiment.

FIG. 7B illustrates a microscope image of the enzyme crystal prepared on the surface of the electroconductive base material. The crystal includes many crystals, not only of a three-dimensional orientation, but also of a film-like form grown in a two-dimensional orientation as well as microcrystals.

The method for immobilizing the enzyme crystal on the electroconductive base material was carried out by a procedure that was identical beyond the step in which the crystal was dropped onto the surface of the electroconductive base material in the method in example 5. The electrode constructed herein having enzyme crystals immobilized thereon was used to measure the electric current response under glucose concentrations of 0 mM and 100 mM, with the chrono amperometry method (a measurement of the change in electric current over time by voltage clamp).

Figure 8:
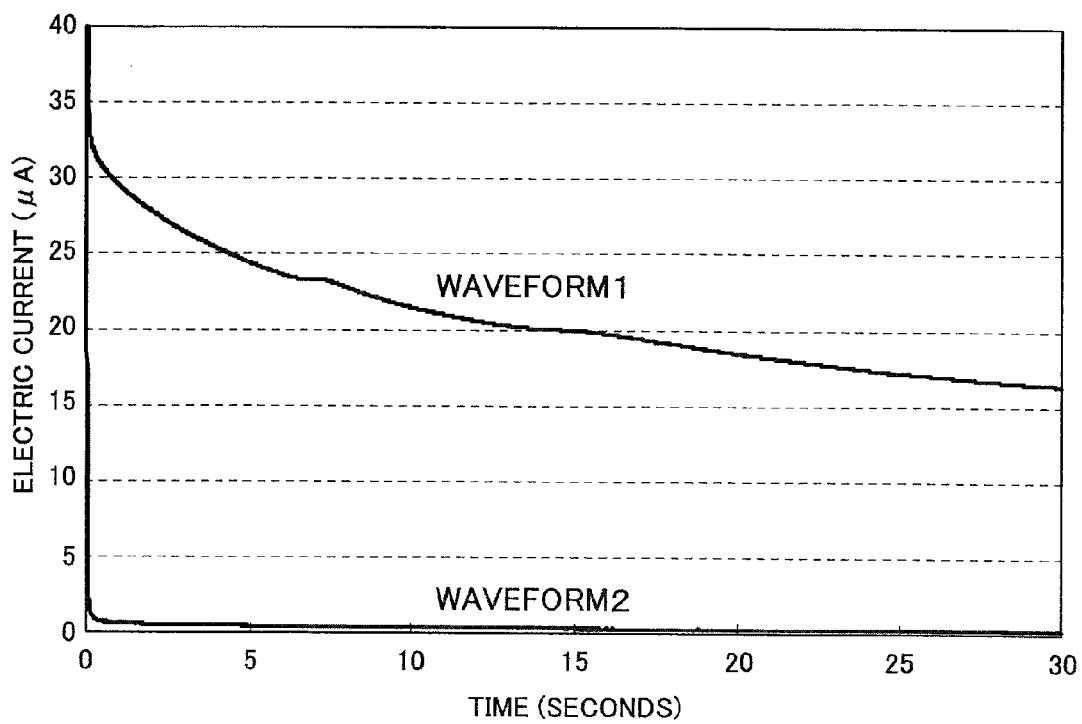
FIG. 8 is a graph illustrating the changes over time in a response value of a catalytic electric current with respect to glucose in an electrode having enzyme crystals immobilized thereon prepared in the seventh embodiment.

The results are shown in FIG. 8.

In FIG. 8, waveform 1 illustrates the results under 100 mM glucose concentration, and waveform 2 illustrates the results under 0 mM glucose concentration, i.e., in a reaction mixture solution that contains no glucose. In view of these results, an electric current value (waveform 1) of 15 µA (after 30 seconds) was obtained under 100 mM glucose concentration. By contrast, the electric current value was very close to 0 in the case where no glucose was included. This confirms, since an electric current value was obtained dependent on the glucose, that the electrode having enzyme crystals immobilized thereon prepared herein functions as an enzyme catalytic function electrode.

Potentiostat CA Measurement Conditions
Init. E (V)=0 (open circuit voltage),
High E (V)=+0.1,
Low E (V)=0,
Init. P/N=N,
Step=1,
Pulse Width (sec)=30,
Sample Interval (s)=0.01,
Quiet Time (sec)=5

Example 8

Catalytic Function Assessment of the Enzyme Crystal Immobilized on the Electroconductive Base Material-3

In the present example, the electrode having enzyme crystals immobilized thereon prepared by carrying out the crystallization reaction of the enzyme on the surface of an electroconductive base material in example 7 was compared, with respect to the electrode function thereof, against the electrode having enzyme crystals immobilized thereon prepared by immobilizing the advance prepared enzyme crystal on the electroconductive surface in example 6.

In order to compare the electrode having enzyme crystals immobilized thereon prepared by carrying out the crystallization reaction of the enzyme on the surface of an electroconductive base material in example 7, with respect to the electrode function thereof, against the electrode having enzyme crystals immobilized thereon prepared by immobilizing the advance prepared enzyme crystal on the electroconductive surface in example 6, the chrono amperometry measurement results obtained in example 6 and in example 7 were compared in terms of the electric current density.

Figure 9:
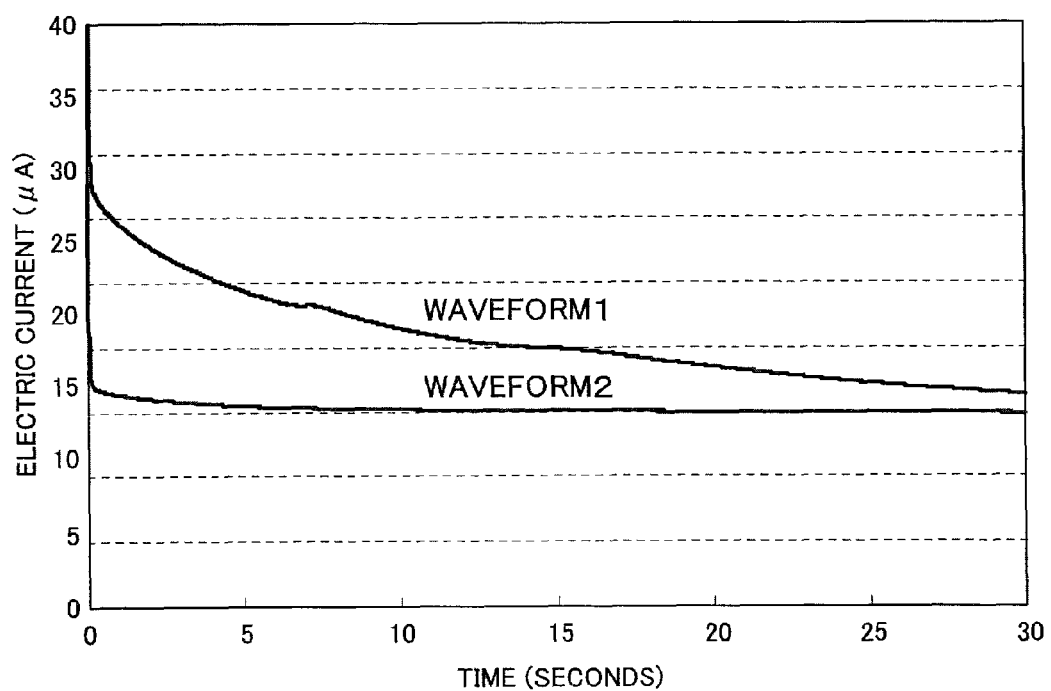
FIG. 9 is a graph illustrating the results from an eighth embodiment, from when the catalytic function of the electrode having enzyme crystals immobilized thereon prepared in the sixth embodiment and of the electrode having enzyme crystals immobilized thereon prepared in the seventh embodiment were compared in terms of the electric current density.

The results are shown in FIG. 9.

In FIG. 9, waveform 1 illustrates the results with the electrode having enzyme crystals immobilized thereon prepared by carrying out the crystallization reaction of the enzyme on the surface of the electroconductive base material in example 7, and waveform 2 illustrates the results with the electrode having enzyme crystals immobilized thereon prepared by immobilizing the advance prepared enzyme crystal on the electroconductive surface in example 6. Both of the electrodes having enzyme crystals immobilized thereon yielded electric current values with an electric current density greater than 0.6 mA/cm$^2$ (waveforms 1 and 2) as the electric current response imparted by the oxidation reaction of glucose. The both electrodes having enzyme crystals immobilized thereon were therefore demonstrated to be able to be fully functional as enzyme catalytic function electrodes. In particular, the electrode having enzyme crystals immobilized thereon obtained by carrying out the crystallization reaction on the electrode surface to immobilize the enzyme crystal yielded an excellent electric current value, with an electric current density greater than 1.0 mA/cm$^2$ within five seconds of the start of measurement, and was confirmed to have a marked improvement in initial output.

Example 9

Estimated Efficiency of the Enzyme Crystallization

In the present example, which concerns the crystallization of the enzyme, the efficiency of crystallizing the enzyme on the electroconductive base material and in the special container was compared.

The purpose of the present example is to confirm the usefulness of the present invention; the present example studied the crystallization efficiency in the case where the crystallization reaction of the enzyme was carried out on the surface of the electroconductive base material in the process of preparing the electrode having enzyme crystals immobilized thereon, as in example 7, and the crystallization efficiency in the case where the crystallization reaction was carried out in advance in the special container, by the method in example 3, as with the enzyme crystal immobilized on the electrode having enzyme crystals immobilized thereon in example 6. More specifically, crystallization reactions of the enzyme were carried out respectively following examples 3 and 7, in the special container and on the electroconductive base material, by the sitting drop method; the amount of enzyme was 50 μg. Next, the crystals thus generated were dissolved in 20 μL of water and the amount of enzyme was measured. The absorbance at 280 nm, which is a measure of the protein concentration, was measured by spectrophotometer, and the amount of enzyme was calculated at a molar extinction coefficient of ε=67,420, and with molecular weight MW=53,665. The results are shown in Table 3 below.

TABLE 3

| No. | Crystal growth on the electroconductive base material (mg/mL) | Crystal growth inside the special container |
|---|---|---|
| 1 | 1.5 | 1.1 |
| 2 | 0.9 | 1.0 |
| 3 | 1.3 | 1.0 |
| 4 | 1.4 | 1.7 |
| 5 | 1.5 | 0.9 |
| 6 | 0.2 (control) | 1.1 |

Measurement results for the protein concentration

These results demonstrated that the amount of enzyme crystallized was about 20 μg, for both crystal growth on the electrode and crystal growth inside the special container, and thus that crystallization occurred at an efficiency of about 50%. This provides confirmation that both techniques possess practical value. The item "No. 6" under "Crystal growth on the electroconductive base material" is a control in which the crystallization reaction was carried out without the addition of precipitant.

Next, the enzyme crystals formed by crystal growth on the electrode and by crystal growth inside the special container were confirmed by electrophoresis. More specifically, a part of the enzyme crystal solution prepared as described above was subjected to 12.5% acrylamide gel electrophoresis, and the protein bands were visualized by staining with CBB.

Figure 10A:
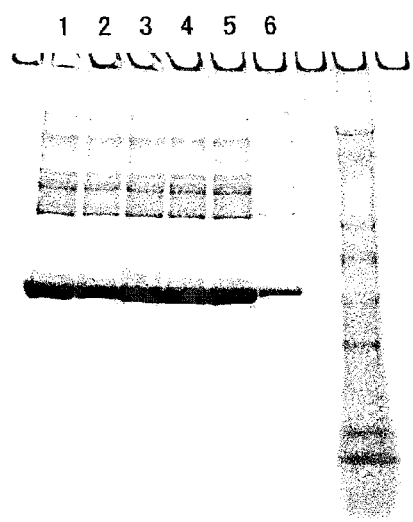
FIG. 10A is an electrophoresis diagram illustrating the results from a ninth embodiment, from when the enzyme crystallization efficiency in a case where crystals were grown on an electroconductive base material was estimated.
Figure 10B:
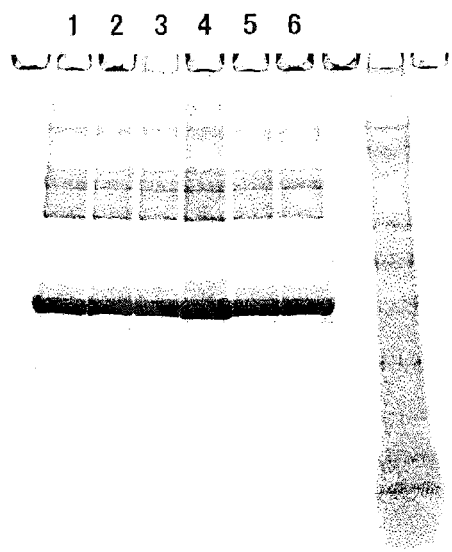
FIG. 10B is an electrophoresis diagram illustrating the results from the ninth embodiment, from when the enzyme crystallization efficiency in a case where crystals were grown in a dedicated container was estimated.

The results are shown in FIGS. 10A and 10B. FIG. 10A illustrates the results in the case where the crystal was grown on the electroconductive base material, and FIG. 10B illustrates the results in the case where the crystal was grown inside the special container.

In FIG. 10A, lane 1 illustrates the results from the enzyme crystal solution of a sample number 1 where the crystal was grown on the electroconductive base material, lane 2 illustrates the results from a sample number 2, lane 3 illustrates the results from a sample number 3, lane 4 illustrates the results from a sample number 4, lane 5 illustrates the results from a sample number 5, and lane 6 illustrates the results from the control.

In FIG. 10B, lane 1 illustrates the results from the enzyme crystal solution of a sample number 1 where the crystal was grown inside the special container, lane 2 illustrates the results from a sample number 2, lane 3 illustrates the results from a sample number 3, lane 4 illustrates the results from a sample number 4, lane 5 illustrates the results from a sample number 5, and lane 6 illustrates the results from a sample number 6. Similarly with respect to the comparison by calculation described above, these results, too, provide confirmation that both techniques implemented crystallization at substantially identical proportions, and that both possess practical value.

Next, examples in which CotA laccase from *Bacillus subtilis* served as the catalyst of the electrode having enzyme crystals immobilized thereon shall now be described in examples 10 to 20.

Example 10

Construction of an Enzyme Expression System, Enzyme Synthesis Through an *E. Coli* Protein Synthesis System, and Protein Purification In order to acquire a high-purity enzyme in the process of crystallization, a genetic engineering technique was used to produce an enzyme as a recombinant protein, which was then purified through a combination of a variety of different forms of chromatography. In particular for the process of crystallization, large quantities of purified enzyme are needed for screening to optimize the crystallization conditions.

Step 1: Construction of an Expression Vector for CotA Laccase from *Bacillus subtilis*

The construction of an enzyme expression vector was designed so that the DNA sequence that encodes the amino acid sequence of CotA laccase from *Bacillus subtilis* as stated in J. Biol. Chem., vol. 277, no. 21, pp. 18849-18859, presented herein as Non-patent Document 1 of the Prior Art Documents, was integrated in between NdeI and HidIII, restriction enzyme recognition sites of the pET-22b(+) vector, and the histidine sequence downstream of the HindIII restriction enzyme recognition site in pET-22b(+) was utilized to attach a histidine to the C-terminus of the enzyme. The base sequence of the protein expressed thereby is illustrated by SEQ ID NO: 7 in the sequence listing, and the amino acid sequence as estimated from the base sequence is illustrated by SEQ ID NO: 8 in the sequence listing.

Step 2: Expression of the Recombinant Protein by *E. Coli*

The enzyme vector obtained in step 1 was used to induce transformation in the *E. coli* strain BL21(DE3)pLysS, and the bacterial cells were inoculated onto an LB culture medium (includes 50 μg/mL ampicillin and chloramphenicol) and the colony was cultured for 18 hours at 37° C. This culturing involved adding the cultured bacterial cells to an LB culture medium (includes 50 μg/mL ampicillin) (one-twentieth the amount of culture solution), and culturing the colony for about one hour (until O.D.=0.2) at 37° C., adding 0.2 mM isopropyl β-D-1-thiogalactopyranoside (IPTG), and culturing the colony with shaking for 18 hours at 20° C. The enzyme expression bacterial cells were recovered by centrifuge separation and stored frozen at −80° C. The sediment was subjected to the following protein purification. The purification that was carried out was a combination of two types of enzyme purification, namely, affinity chromatography (step 3), and an ion exchange chromatography (steps 3 and 4) that followed the charge characteristics of the protein.

Step 3: His-Tag Protein Purification by Affinity Chromatography

The protein expressed in step 2 was a His-tag fusion protein, and the protein was purified via the His-tag. The cryopreserved enzyme expression bacterial cells were suspended in 10 mM Tris-HCl and 1 mM EDTA, pH 7.4, and a 0.4% surfactant (BRIJ® 58) was added, and the suspension was allowed to stand for 30 minutes on ice. Next, an ultrasonic disruption was carried out, following which the cell disruption solution was fractionated by centrifuge separation. Next, an open column was packed as appropriate with a purification carrier using a metal affinity carrier (TALON®) for purifying histidine-tagged fusion proteins, and pre-rinsed with 20 mM sodium phosphate, 5 mM imidazole, and 0.5 M NaCl solution, following which 0.5 M NaCl was added to the cell disruption solution and the solution was applied to the column. After rinsing with 20 mM sodium phosphate, 5 mM imidazole, and 0.5 M NaCl solution, the enzyme was eluted with a 20 mM sodium phosphate, 500 mM imidazole, and 0.5 M NaCl solution. In order to remove the salts used in the elution (imidazole and NaCl), a buffer solution of 25 mM Tris-HCl (pH 7.4) served as an external solution for overnight dialysis.

Step 4: Protein Purification by Ion Exchange Chromatography

The protein solution acquired in step 3 described above was further purified using ion exchange chromatography that followed the charge properties of the protein.

Purification by chromatography with MONO Q®, which is an anion exchanger, was carried out. CotA laccase (with a histidine-tagged C-terminus) is a protein with a molecular weight of 60.1 kDa and an isoelectric point (pI) of 6.1. When the buffer solution for solubilizing the CotA laccase is set to a pH of 7.5, the pH is higher than the pI, and therefore adsorption to the anion exchanger is believed to take place. The protein failed to adsorb to the carrier in purification with MONO S®, which is a cation exchanger known from the literature.

More specifically, MONO Q® 5/50 GL (GE Healthcare; column volume is about 1 mL) was used. MONO Q® is a strong anion exchanger that is based on MonoBeads, which are porous particles having very high separation ability and high binding capacity, and has Quaternary ammonium (Q) as an ion exchanger. According to the instruction text from the manufacturer, the binding capacity of MONO Q® is 65 mg/mL of gel. The buffer solution to be used in the MONO Q® column and the protein to be added thereto were first passed through a 0.22-μm filter.

The device, equipment, and reagents used herein are shown below.

Device: AKTA explorer 10S (GE Healthcare)
Carrier: MONO Q® 5/50 GL (GE Healthcare)
Reagents:
Buffer solution A [20 mM Tris-HCl (pH 7.5), 5 mM EDTA, 5 mM 2-mercaptoethanol]
Buffer solution B [20 mM Tris-HCl (pH 7.5), 5 mM EDTA, 5 mM 2-mercaptoethanol, 1M NaCl]

In the procedure for purification by MONO Q®, 25 mM potassium phosphate (pH 7.4) and 1 mM EDTA served as a base buffer solution for rinsing the carrier, thus bringing the column to equilibrium. Next, the protein solution acquired in step 3 was applied to the column, and the protein was adsorbed onto the carrier, following which the carrier was rinsed with the above-described base buffer solution and impurities were removed. The base buffer solution next served as an initiating buffer solution for eluting the protein using a salt concentration gradient of 0 to 500 mM KCl. Subsequently, in order to remove the KCl, 1 mM EDTA and a buffer solution of 25 mM Tris-HCl (pH 7.4) served as an external solution for overnight dialysis. More specifically, elution was carried out with the following procedure.

Purification Procedure

1) The MONO Q® column is brought to equilibrium with ten column volumes of buffer solution A.

The flow rate for MONO Q® recommended by the manufacturer is 0.5 to 3.0 mL/min, and the limiting pressure is 4 MPa.

2) Protein (previously dialyzed with the buffer solution A) is added to the MONO® column having been brought to equilibrium with ten column volumes of buffer solution A.

3) The column is rinsed with ten column volumes of buffer solution A, and non-adsorbed protein is removed.

4) The protein is eluted, while being fractionated with a fraction collector, in ten column volumes according to a linear gradient using the buffer solution A and the buffer solution B.

The protein is eluted with a method using a salt concentration gradient in which the KCl concentration is increased from 0 to 500 mM.

5) The elution fraction of the protein is subjected to SDS-PAGE and the protein is checked.

6) The column is replaced with ultrapure water. Thereafter, the column is rinsed with 2 M NaCl, then 2 M NaOH, then 75% acetic acid, in the stated order.

Figure 11A:
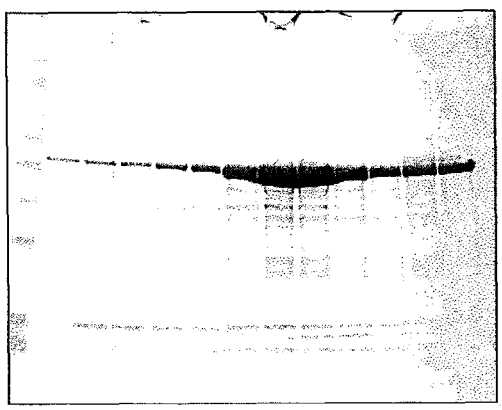
FIG. 11A is an electrophoresis diagram illustrating the results from a tenth embodiment, from when the eluted fraction in a MONO Q® column purification (at an early elution stage) was checked by SDS-PAGE.
Figure 11B:
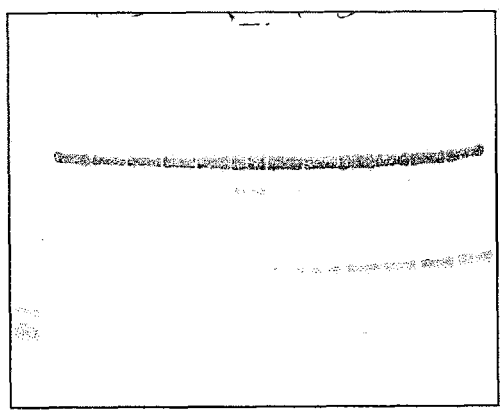
FIG. 11B is an electrophoresis diagram illustrating the results from the tenth embodiment, from when the eluted fraction in the MONO Q® column purification (at a later elution stage) was checked by SDS-PAGE.

FIGS. 11A and 11B show the results from when the elution fraction of the protein was subjected to SDS-PAGE. In greater detail, FIG. 11A illustrates the results from electrophoresing a fraction from an early stage of elution (a KCl concentration of approximately 100 mM) (this fraction is hereinafter called "enzyme solution fraction I"), and FIG. 11B illustrates the results from electrophoresing a fraction from a later stage of elution (a KCl concentration of approximately 100 mM) (this fraction is hereinafter called "enzyme solution fraction II"). A band having a molecular weight of about 60 kDa was successfully detected in both. Herein, although the protein was eluted with a method using a salt concentration gradient in which the KCl concentration is increased from 0 to 500 mM, it was found that there were two enzyme solution fractions, one that was eluted at the early stage of elution and another that was eluted at the later stage of elution. In a side-by-side viewing of the chromatography charts (not shown here) and the electrophoresis diagrams in FIGS. 11A and 11B, it did not appear that the two fractions could be sharply separated from each other; rather, it seemed that there had been admixing of both the enzyme that had been weakly bound to the MONO Q® and the enzyme that had been strongly bound thereto. It can be inferred that this was triggered by some physical property of the enzyme.

Example 11

Purity Assay of the Purified Enzyme

In the present example, the question of whether the purified enzyme acquired in example 10 was the high-purity enzyme needed for crystallization was checked.

More specifically, the protein solution immediately after synthesis by the *E. coli* protein synthesis system was carried out in example 10 (steps 1 to 2), the protein solution purified by affinity chromatography (steps 1 to 3), and the protein solution purified by a combination of affinity chromatography and ion exchange chromatography (steps 1 to 4) were subjected to SDS-PAGE electrophoresis.

Figure 12:
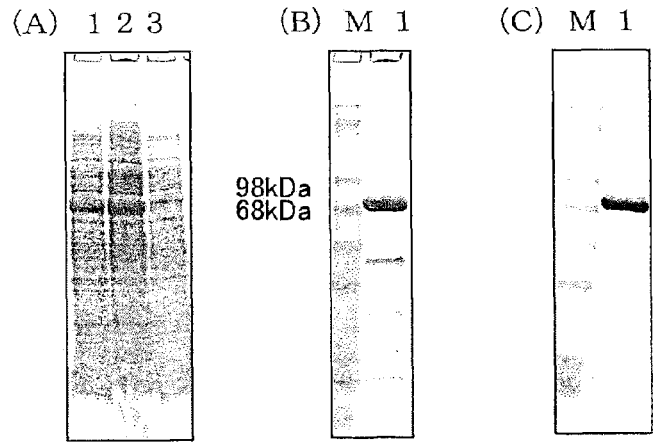
FIG. 12 is an electrophoresis diagram illustrating the results from an eleventh embodiment, from when the purity of the purified enzyme purified in the tenth embodiment was checked.

The results are shown in FIG. 12. In greater detail, panel A is the protein solution immediately after synthesis by the *E. coli* protein synthesis system was carried out, where lane 1 is the result of electrophoresing the entire disruption solution of the *E. coli* that were made to express the protein, lane 2 is the result of electrophoresing the soluble fraction thereof, and lane 3 is the result of electrophoresing the solution obtained by passing the soluble fraction of lane 2 through the affinity chromatography carrier in step 3. Panel B is the result of electrophoresing the protein solution obtained by purifying the entire disruption solution of *E. coli* by affinity chromatography, and panel C is the result of electrophoresing the protein solution purified by the combination of affinity chromatography and ion exchange chromatography. Lane M in panels B and C is a molecular weight marker.

The results in panel A show that a protein band having a molecular weight of about 60 kDa was visible in the *E. coli* disruption solution, and the protein had been expressed. In light of the results in panel B, it can be understood that the protein had efficiently PersonName (*2) bound to the affinity chromatography carrier. In panel C, substantially only one signal band of the target protein was observed. Combining affinity chromatography and ion exchange chromatography was therefore demonstrated to make it possible to purify high-purity CotA laccase.

Example 12

Measurement of the Activity of the Purified Enzyme

In the present example, the activity of the purified enzyme acquired in example 10 was measured.

The enzyme solutions of the enzyme solution fractions I and II acquired through steps 1 to 4 in example 10 were substituted with 25 mM Tris 7.5, 1 mM EDTA, 5 mM 2-mercaptoethanol, and 50% glycerol by dialysis after purification. In order to prepare the solution as an enzyme solution for crystallization, the enzyme solution fractions were dialyzed against a 100 mM sodium citrate buffer solution (pH 5.5). As a result, the proteins in the enzyme solution fraction I precipitated and denatured. Investigating the enzyme concentration at which precipitation occurred revealed that, with the CotA laccase, precipitation occurred and activity was compromised at an enzyme concentration of 0.5 mg/mL and higher. The denaturation also occurred with the purified enzyme subjected only to affinity chromatography purification after step 3 in example 1, and there was no instance of precipitation when 2-mercaptoethanol was added to the enzyme solution as a reducing agent and dialysis was carried out. There was no instance of precipitation with the enzyme solution fraction II, which was successfully substituted with the 100 mM sodium citrate buffer solution. Since 2-mercaptoethanol could not be added, the enzyme solution fraction II was selected to be the enzyme solution for crystallization.

Next, the catalytic activity (substrate ABTS oxidation activity) of the enzyme solution obtained by dialyzing the enzyme solution fraction II was compared against the pre-dialysis enzyme solution. Both enzyme solutions included the same amount of enzyme, and the sole difference was the composition of the solvents. The result was that the catalytic activity was nearly twice as high after dialysis. The details of the reasons therefor are not known, but a trigger was inferred to be the removal of the 2-mercaptoethanol by dialysis.

Laccase activity was measured by the following procedure. A 20 mM sodium acetate buffer solution (pH 5.0) including 0.1 mM copper sulfate and 1 mM ABTS as the substrate was used as the reaction solution to measure laccase activity by colorimetry. First, the enzyme solution was added to the reaction solution to start the reaction. The reaction was carried out at 50° C. Measurements were taken by the change in absorbance (the enzyme reaction rate) at 418 nm, which is associated with the oxidation of the substrate (ABTS).

The specific activity of the enzyme solution was measured using ABTS as the substrate. A 50 mM sodium acetate buffer solution (pH 5.5) including 0.4 mM ABTS served as the reaction solution; the enzyme solution was added to bring the total amount to 200 μL. The reaction was carried out at 25° C. 1U was defined as the amount of enzyme for oxidizing 1 μmol of ABTS per minute, and the specific activity was calculated. With the result of 8.3 U/mg protein (μmol/min mg$^{-1}$), the enzyme included in the enzyme solution had adequate catalytic activity as an enzyme for crystallization.

Example 13

Various Properties of the Enzyme (pH Properties)

In the present example, which relates to various properties of the enzyme, the pH properties were examined.

The pH properties of the purified enzyme acquired through steps 1 to 4 in example 10 were examined by measuring the catalytic activity in pH ranges from 3.5 to 10.0. The catalytic activity was measured by colorimetry using a 20 mM sodium acetate buffer solution (pH 5.0) including 1 mM ABTS and 0.1 mM copper sulfate as the reaction solution. First, the enzyme solution was added to the reaction solution to start the reaction. The reaction was carried out at 50° C. Measurements were taken by the change in absorbance (the enzyme reaction rate) at 418 nm, which is associated with the oxidation of the substrate (ABTS). To measure the activity, pH 3.5-5.5 citric acid, pH 6-7 phosphoric acid, pH 6.5-9 tris-HCl, and pH 8.5-10 glycerin-NaOH were used as buffer components of the buffer solution in each of the pH ranges.

Figure 13:
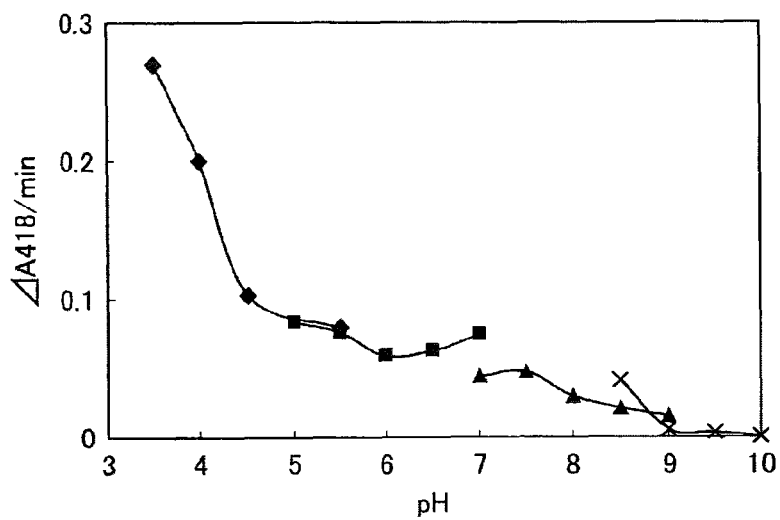
FIG. 13 is a graph illustrating the results from a thirteenth embodiment, from when a pH property in the catalytic activity of the purified enzyme purified in the tenth embodiment was checked.

The results are shown in FIG. 13. The result was that the optimal pH was the slightly acidic range. Such pH properties are analogous to multi-copper oxidase (CueO), which is also an oxidoreductase, and the like.

Example 14

Various Properties of the Enzyme (Temperature Dependence)

In the present example, which relates to various properties of the enzyme, the temperature dependence was examined.

The temperature dependence of the purified enzyme acquired through steps 1 to 4 in example 10 were examined by measuring the catalytic activity at 25 to 80° C. The catalytic activity was measured by colorimetry using a 20 mM sodium acetate buffer solution (pH 5.0) including 1 mM ABTS and 0.1 mM copper sulfate as the reaction solution. First, the enzyme solution was added to the reaction solution to start the reaction. The reaction was carried out at the above-mentioned predetermined temperatures, and activity was measured by the change in absorbance (the enzyme reaction rate) at 418 nm, which is associated with the oxidation of the substrate (ABTS). pH 3.5-5.5 citric acid was used as the buffer component of the buffer solution.

Figure 14:
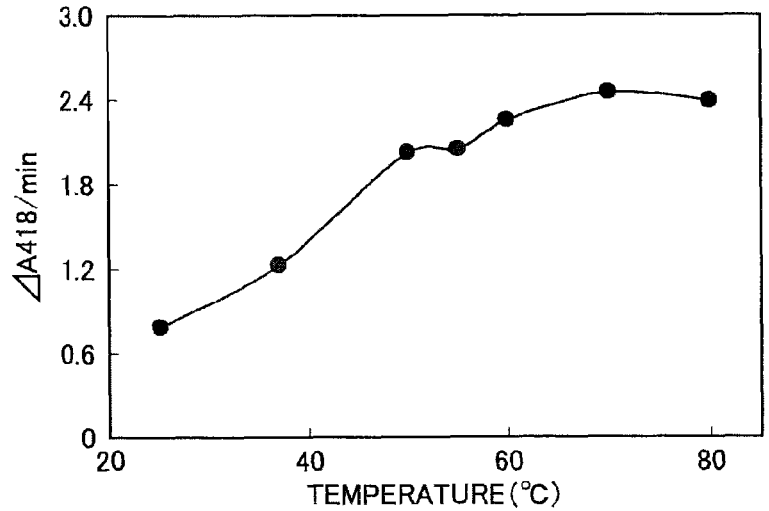
FIG. 14 is a graph illustrating the results from a fourteenth embodiment, from when the temperature dependency in the catalytic activity of the purified enzyme purified in a tenth embodiment was checked.

The results are shown in FIG. 14. The result was that the optimal temperature was around 70° C. This is analogous to CueO laccase from $E.\ coli$, which is also an oxidoreductase. Since activity can be maintained in high-temperature regions, utilization as a useful enzyme electrode catalyst able to withstand long-term usage and a variety of usage conditions, including high-temperature regions, is possible.

Example 15

Screening for Enzyme Crystallization Conditions, and Crystallization of the Enzyme In the present example, screening for the enzyme crystallization conditions was carried out, followed by preparation of the enzyme crystal.

The crystallization reaction was carried out by referring to Enguita F J et al., Acta. Crystallogr. D. Biol. Crystallogr., 2002, 58 (Pt. 9), pp. 1490-1493, which discloses a crystallization and structural determination pertaining to CotA laccase from $Bacillus\ subtilis$, which is the same as the purified enzyme that was acquired through steps 1 to 4 in example 10. This document is presented herein as Non-patent Document 2 of the Prior Art Documents.

Step 1: Dialysis and Concentration

The purified enzyme acquired through steps 1 to 4 in example 10 was dialyzed against a buffer solution of crystallization reaction mother liquor (100 mM sodium citrate buffer solution, pH 5.5). After the buffer solution exchange, concentration by an ultrafiltration spin column (15 mg/mL) was carried out. When the post-dialysis status of the enzyme solution was checked, precipitation of the enzyme had taken place in the enzyme solution fraction I, as was confirmed in example 12. This is believed to be because the buffer solution exchange had caused a decline in the solubility of the enzyme. An enzyme solution in which precipitation has taken place is of no use for a crystallization reaction, and therefore the crystallization reaction was carried out with the enzyme solution fraction II, in which precipitation of the enzyme had not taken place. After concentration, the enzyme concentration and purity were measured by scanning light of respective wavelengths using a spectrophotometer. The result was that the ratio between the two wavelengths 260 and 280, which are indicative of the extent of admixing of nucleic acid that would interfere with the enzyme crystallization, was 0.52, providing confirmation that no nucleic acid admixing had occurred. Combining purification by ion exchange chromatography made it possible to substantially entirely eliminate admixing of the nucleic acid, which is difficult to remove with affinity purification alone.

Step 2: Crystallization

In order to ascertain the conditions whereby the crystals would deposit, screening for crystallization conditions was conducted by referring to the crystallization conditions set forth in the above-mentioned Non-patent Document. First, the crystallization conditions set forth in Non-patent Document 2 presented in the section on Prior Art Documents above were allowed to vary by about 10%, and initial screening was carried out. At this time, two screening plates were used, and screening was implemented in a 15×2 format. More specifically, droplets obtained by mixing enzyme solution and precipitant solution with the formulated enzyme concentration and precipitant concentration shown below on a 4-μL reaction scale were prepared on cover glass; the cover glass was reversed and covered in a container in which precipitant solution had been placed, and the screening was carried out by vapor diffusion. The solution was allowed to stand for five days in an incubator at 20° C. to allow crystallization to proceed, following which the presence or absence of crystals was checked by microscopic observation.

Shown below are the precipitant concentration and the enzyme concentration of the enzyme solution.

Enzyme Concentration of the Enzyme Solution:
8 mg/mL (CotA laccase)

Figure 15A:
FIG. 15A is a photograph illustrating an image, observed by microscopy, of an enzyme crystal prepared in a fifteenth embodiment (the conditions that are circled in Table 4)
Figure 15B:
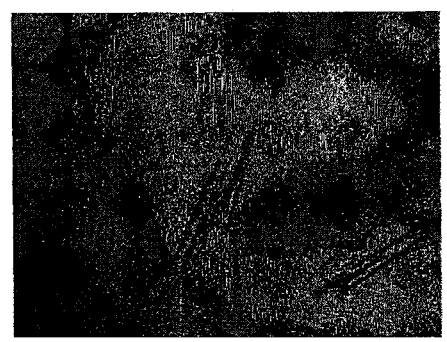
FIG. 15B is a photograph illustrating an image, observed by microscopy, of an enzyme crystal prepared in the fifteenth embodiment (the conditions that are circled in Table 4)

Composition and Precipitant Concentration of the Crystallization Reaction Mother Liquor:
100 mM sodium citrate buffer solution, pH 5.5
15% glycerol
10, 15, 20% isopropyl alcohol
10, 12, 14, 16, 18, 20% polyethylene glycol 4K The results are shown in Table 4. Needle-shaped crystals (about 1.0 mm), as are illustrated in FIGS. 15A and 15B, were confirmed by microscope observation to have formed under those conditions that have been marked with a circle in Table 4. It can be understood, in light of these results, that crystallization took place only under conditions where the precipitant concentration was high. At the same time, a considerable amount of contaminant precipitate, beyond the enzyme crystals, was also confirmed to have occurred. It is expected that this was triggered by overly high enzyme concentration.

TABLE 4

Content and results of screening for enzyme crystallization conditions (for one plate)

| | | Polyethylene glycol concentration (%) | | | | |
|---|---|---|---|---|---|---|
| | | 10 | 12 | 14 | 16 | 18 |
| Isopropyl alcohol concentration (%) | 10 | | | | | |
| | 15 | | | | ○ | ○ |
| | 20 | | | | | ○ |

In view of the foregoing experimental results, subsequent screening was carried out with the objective of reducing the formation of contaminant precipitate. In this experiment, the enzyme concentration was lowered and crystallization conditions were examined. Identically with respect to the first time, the solution was allowed to stand for five days in an incubator at 20° C. to allow crystallization to proceed, following which the presence or absence of crystals was confirmed by microscope observation.

Shown below are the precipitant concentration and the enzyme concentration of the enzyme solution.

Figure 16A:
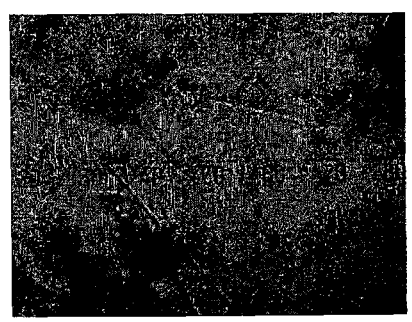
FIG. 16A is a photograph illustrating an image, observed by microscopy, of an enzyme crystal prepared in the fifteenth embodiment (the conditions that are double-circled in Table 5)
Figure 16B:
FIG. 16B is a photograph illustrating an image, observed by microscopy, of an enzyme crystal prepared in the fifteenth embodiment (the conditions that are double-circled in Table 5)

Enzyme Concentration of the Enzyme Solution:
4 or 8 mg/mL (CotA laccase)
Composition and precipitant concentration of the crystallization reaction mother liquor:
100 mM sodium citrate buffer solution, pH 5.5
15% glycerin
14, 16, 18, and 20% isopropyl alcohol
10, 12, 14, 16, 18, and 20% polyethylene glycol 4K The results are shown in Table 5. A plurality of enzyme crystals (about 0.5 to 1.0 mm), as illustrated in FIGS. 16A and 16B, were confirmed to have formed under the conditions marked with a double-lined circle in Table 5. In these results, too, it was not possible to reduce the amount of contaminant precipitate other than the enzyme crystal. It is believed that such contaminant precipitate is generated because there is a high concentration of precipitant, and is mixed with the enzyme in the crystallization cycle described here. A large aggregate (block) of crystal was observed to have formed at a heightened enzyme concentration (8 mg/mL) (FIG. 16A), and a trend in which a plurality of enzyme crystals that were smaller (about 0.5 mm) were formed at a lower enzyme concentration (4 mg/mL) (FIG. 16B) was also observed. This provides confirmation that crystals of different sizes can be made by adjusting the enzyme concentration of the enzyme solution.

The foregoing results demonstrated that the conditions whereby the enzyme crystal would precipitate were 20% precipitant, 4 to 8 mg/mL enzyme concentration, buffer solution pH 5.5, temperature 20° C., and a required number of days of about five days. It was confirmed that enzyme crystals could be reliably prepared with favorable reproducibility, on the basis of such crystallization conditions.

TABLE 5

Content and results of screening for enzyme crystallization conditions

|  | Polyethylene glycol concentration (%) | | | | | |
| --- | --- | --- | --- | --- | --- | --- |
|  | 10 | 12 | 14 | 16 | 18 | 20 |
| Isopropyl alcohol concentration (%) 14 |  |  |  |  |  |  |
| 16 |  |  |  |  |  |  |
| 18 |  |  |  |  |  | ◎ |
| 20 |  |  |  |  |  | ◎ |

Example 16

Preparation of the Electrode Having Enzyme Immobilized Thereon and Assessment of Catalytic Function In the present example, utilization as an electrode catalyst of a biological fuel cell was assumed, and an electrode having enzyme immobilized thereon was prepared. The catalytic function thereof was assessed.

The purified enzyme acquired through steps 1 to 4 in example 10 was used as an electrode catalyst of an electrode having an enzyme immobilized thereon. To immobilize the enzyme onto the electroconductive base material, a method for using a photo-crosslinkable polymer was selected. More specifically, an enzyme immobilization kit (Toyo Gosei) was used to implement the method in accordance with the standard protocol included with the kit. The enzyme immobilization kit is an experimental kit that is ideal for the early stages of investigating biosensors for electrochemical detection. The enzyme-immobilizing polymer BIOSURFINE® included with the kit was used as an immobilization material to prepare an electrode having an enzyme immobilized thereon obtained by immobilizing an enzyme onto an electroconductive base material.

A potentiostat was then used to assess the electrode having an enzyme immobilized thereon. The assessment was carried out by measuring the catalytic electric current through the chronoamperometry method (a measurement of the change in electric current over time by voltage clamp). More specifically, the electrode having the purified enzyme (50 μg) immobilized thereon as working electrode was immersed in a reaction mixture solution (50 mM sodium citrate, pH 5.2, 1 mM ABTS), as were a counter electrode (carbon) and a reference electrode (silver-silver chloride), and the electric current response associated with the reduction reaction of the ABTS (oxidation-reduction potential: 0.5 V) was measured.

The electrochemical reaction formulae are as follows.

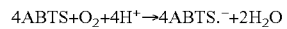

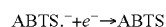

The CA measurement conditions of the potentiostat are shown below.
Init. E (V)=0 (open circuit voltage),
High E (V)=+0.1,
Low E (V)=0,
Init. P/N=N,
Step=1,
Pulse Width (sec)=30,
Sample Interval (s)=0.01,
Quiet Time (sec)=2

Figure 17:
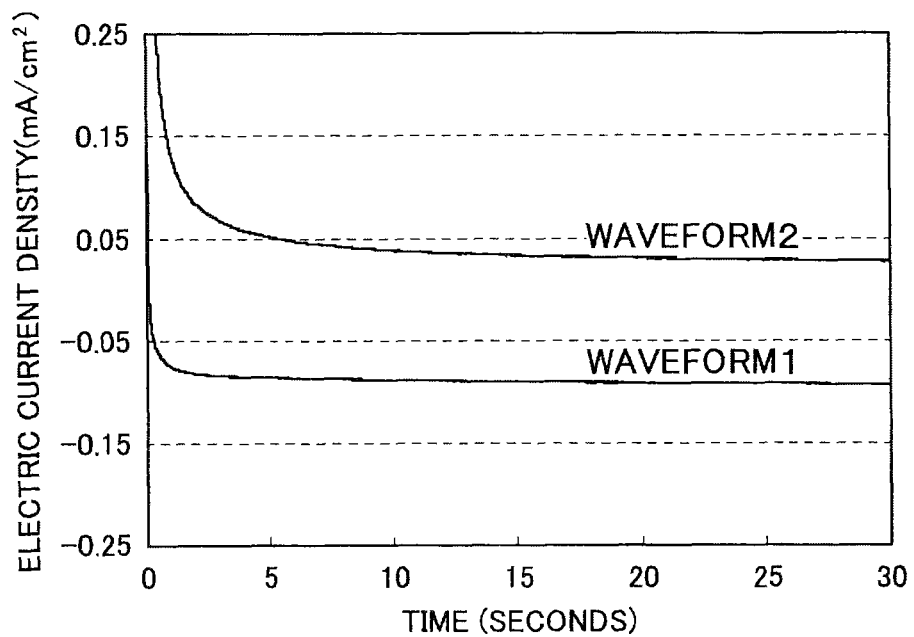
FIG. 17 is a graph illustrating the results from a sixteenth embodiment, from when the catalytic electric current of an electrode having an enzyme immobilized thereon, on which the purified enzyme purified in the tenth embodiment has been immobilized, was measured by chronoamperometry.

The results are shown in FIG. 17. Waveform 1 illustrates the catalytic electric current observed with an electrode that had undergone enzyme immobilization reaction treatment, and waveform 2 illustrates the catalytic electric current observed with an electrode that underwent the immobilization reaction treatment but without the addition of the enzyme. The result was that the electric current density of the catalytic electric current was −0.09 mA/cm² with the electrode having an enzyme immobilized thereon (waveform 1). An electric current can be observed on the negative side, because the repeat reduction wave of the ABTS cation radical was observed. By contrast, the electric current density of the catalytic electric current was 0.03 mA/cm² with the electrode on which no enzyme had been immobilized. These results provide confirmation that the purified enzyme (CotA laccase) caused a negative catalytic electric current to flow, and can be used as a cathode-side catalyst for a biological fuel cell.

Example 17

Preparation of the Electrode Having Enzyme Crystals Immobilized Thereon

In the present example, utilization as an electrode catalyst of a biological fuel cell was assumed, and an electrode having enzyme crystals immobilized thereon was prepared.

The enzyme crystal prepared in example 15 was used as an electrode catalyst for an electrode having enzyme crystals immobilized thereon. The immobilization of the enzyme crystal on the electroconductive base material was carried out by a method using a photo-crosslinkable polymer, similarly with respect to example 16. More specifically, an enzyme immobilization kit (Toyo Gosei) was used to implement the method in accordance with the standard protocol included with the kit. The enzyme immobilization kit is an experimental kit that is ideal for the early stages of investigating biosensors for electrochemical detection. The enzyme-immobilizing polymer BIOSURFINE® included with the kit was used as an immobilization material to immobilize the enzyme crystal on a carbon electrode and prepare an electrode having an enzyme immobilized thereon.

More specifically, the enzyme crystal acquired in example 15 underwent a holoenzyme conversion reaction for binding thereto the cofactor $CuSO_4$ needed for expression of enzyme activity. Then, a special paper string was used to suck the liquid portion out from the crystallization reaction solution, leaving about 10 μL, to concentrate the crystal. The entire concentrated crystal solution was added in a dropwise fashion to the surface of the electrode (2.5 mm² of an electrode surface, in the form of a flat plate), and a paper-string filter was used to completely suck up the liquid portion. Next, 5 μL of a polymer solution that had been diluted to 2% was added in a dropwise fashion to the electrode, which was then dried and thereafter exposed to UV light for five minutes to thereby immobilize the enzyme crystals.

Example 18

Catalytic Function Assessment of the Electrode Having Enzyme Crystals Immobilized Thereon-1

In the present example, the catalytic function of the electrode having enzyme crystals immobilized thereon prepared by immobilizing the enzyme crystal prepared by the enzyme crystallization reaction set forth in example 15 on the surface of an electroconductive base material by the method set forth in example 17 was assessed.

The enzyme crystal prepared by the enzyme crystallization reaction set forth in example 15 was immobilized onto an electrode by the method set forth in example 17, and the catalytic electric current was measured by cyclic voltammetry (hereinafter in some cases abbreviated as "CV").

The CA measurement conditions of the BAS potentiostat are shown below.

Figure 18:
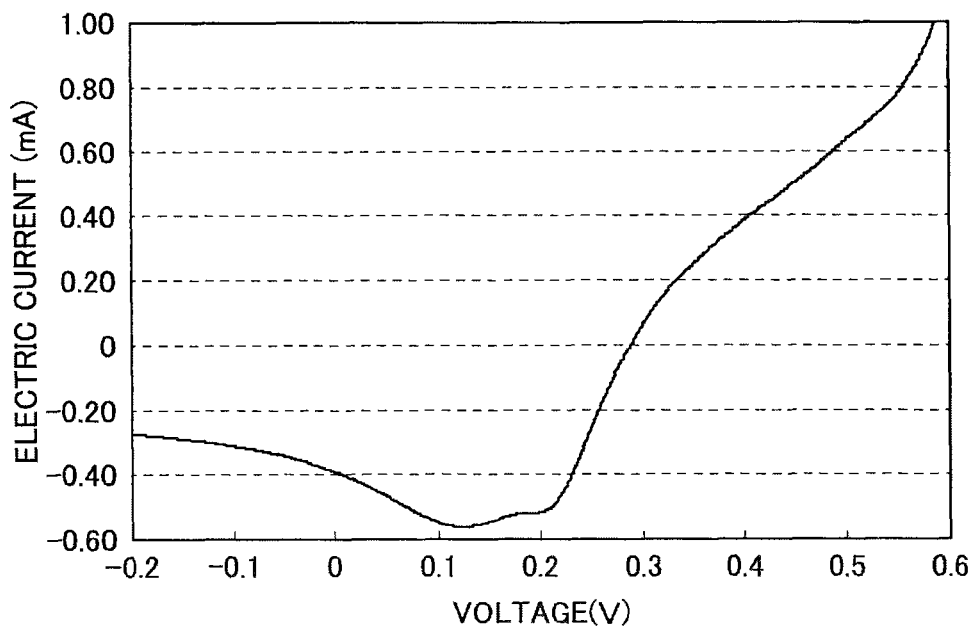
FIG. 18 is a graph illustrating the results from an eighteenth embodiment, from when the catalytic electric current of an electrode having enzyme crystals immobilized thereon, on which the enzyme crystal prepared in the fifteenth embodiment has been immobilized, was measured by cyclic voltammetry.

Init. E (V)=−0.2,
High E (V)=0.6,
Low E (V)=−0.2,
Init. P/N=P,
Scan Rate (V/s)=0.02,
Segment=2,
Sample Interval (V)=0.001,
Quiet Time (sec)=5,
Sensitivity (NV)=$1e^{-5}$ The results are shown in FIG. 18. A repeat reduction wave of the ABTS cation radical in the electrochemical reactions illustrated below was observed. This provides confirmation that the electrode having enzyme crystals immobilized thereon prepared in the present example functions as an electrode catalytic function electrode.

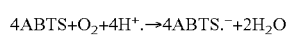

$$4ABTS + O_2 + 4H^+ \rightarrow 4ABTS.^- + 2H_2O$$

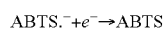

$$ABTS.^- + e^- \rightarrow ABTS$$

Example 19

Catalytic Function Assessment of the Electrode Having Enzyme Crystals Immobilized Thereon-2

In the present example, the catalytic function of the electrode having enzyme crystals immobilized thereon prepared by immobilizing the enzyme crystal prepared by the enzyme crystallization reaction set forth in example 15 on the surface of an electroconductive base material by the method set forth in example 17 was assessed.

The enzyme crystal prepared by the enzyme crystallization reaction set forth in example 15 was immobilized on an electrode by the method set forth in example 17, and the catalytic electric current was measured by chronoamperometry. More specifically, the change in electric current caused by an applied voltage after a time t was measured. The parameters for CA measurement were set with reference to the CV results in Example 18, the initial potential ($E_0$) being the open circuit potential, the impressed voltage being 0.5 V, and the time for the impressed voltage to start being applied being 5 s. Because the enzyme immobilized herein was laccase, the electric current to be observed would be the electric current consumed in the reduction of oxygen, and thus it was desirable to set to a more negative potential than the repeat reduction wave.

Figure 19:
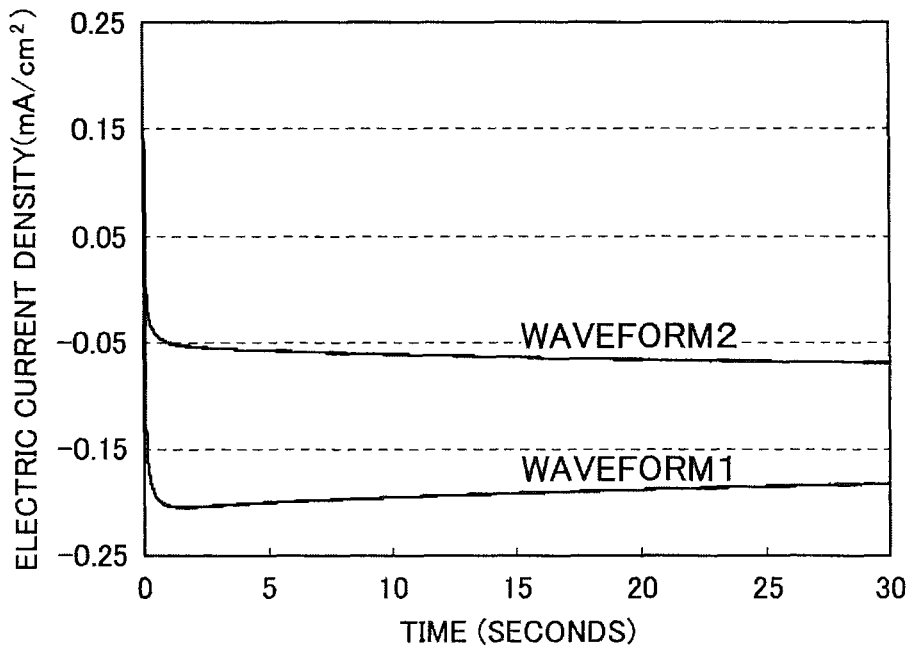
FIG. 19 is a graph illustrating the results from a nineteenth embodiment, from when the catalytic electric current of an electrode having enzyme crystals immobilized thereon, on which the enzyme crystal purified in the fifteenth embodiment has been immobilized, was measured by chronoamperometry.

The results are shown in FIG. 19. Waveform 1 illustrates the catalytic electric current observed with an electrode that had undergone an enzyme crystal immobilization reaction treatment, and waveform 2 illustrates the catalytic electric current observed with an electrode obtained by performing an immobilization reaction treatment on an enzyme crystal pseudo-substance prepared by deliberately lowering the precipitant concentration so that crystallization would not occur, as a control experiment. The result was that a catalytic electric current with an electric current density of 0.18 mA/cm² was observed with the electrode having enzyme crystals immobilized thereon (waveform 1). By contrast, a catalytic electric current with an electric current density of 0.07 mA/cm² was observed with the enzyme crystal prepared by deliberately lowering the precipitant concentration so that crystallization would not occur as a control experiment (waveform 2). These results demonstrate that the enzyme crystallization of CotA laccase, which is useful as a cathode-side catalyst for a biological fuel cell, provided an enhanced catalytic electric current. Because oxygen is the substrate in reactions involving laccase, the reaction rate was found to reach a peak at the limit of dissolved oxygen concentration in the reaction solution. The electric current density of 0.18 mA/cm² obtained in the present experiment, too, is believed to be a response current value corresponding to the dissolved oxygen. For this reason, the expectation for the level of electric current enhancement imparted by enzyme crystallization is that employing atmospheric oxygen in the reaction will yield an even greater effect.

Example 20

Performance Assessment of a Biological Fuel Cell Using the Electrode Having Enzyme Crystals Immobilized Thereon In the present example, the electrode having enzyme crystals immobilized thereon of the present invention was actually used to construct a biological fuel cell and the performance thereof was assessed.

Rather than the enzyme crystallization reaction set forth in example 15 being carried out in a crystallization reaction container, the enzyme crystallization reaction was carried out in a carbon material employed in the cathode of the biological fuel cell. That is, an electrode having enzyme crystals immobilized thereon was prepared by carrying out the crystallization reaction of the enzyme atop the electroconductive base material. The carbon material used herein is carbon paper (hereinafter abbreviated as "CP") that was coated with KETJENBLACK™ (hereinafter abbreviated as "KB") highly electroconductive carbon particles.

The specific procedure is shown below.

Step 1: Coating KB onto CP

The CP was coated with an appropriate amount of the KB highly electroconductive carbon microparticles.

Step 2: Crystallization of the CotA Laccase Inside the Electrode

As is set forth in example 15, the purified enzyme acquired through steps 1 to 4 in example 10 was dialyzed against a buffer solution of the crystallization reaction mother liquor (100 mM sodium citrate buffer solution, pH: 5.5). The enzyme crystallization reaction solution (100 mM citric acid buffer solution, pH: 5.5; 15% glycerin; 18% 2-propanol; and 20% polyethylene glycol (PEG)) and enzyme solution (15 mg/mL) were then blended and a crystallization reaction was carried out in the CP/KP electrode prepared in step 1, by following the procedure set forth in example 15. This electrode served as the cathode for the construction of a biological fuel cell (example).

Step 3: Preparation of Biological Fuel Cell

In the present example, two types of biological fuel cell batteries were assembled. The biological fuel cell in FIG. 1 was assembled by layering the cathode, fuel gel, and anode in the stated order onto a mold frame made of acrylic and screwing down all four sides. The cathode and the anode were both set to be 14 mm×14 mm. The mold frames made of acrylic sheet 1 mm thick and of an acrylic sheet 2 mm thick, where a 1 cm×1 cm square hole was opened in the middle section of an acrylic sheet, were used as the outer frame. Screw holes were made at the four sides of the square hole. The fuel gel was held in and fitted to the mold frame made of acrylic in which the square hole had been opened at the middle section of the acrylic sheet. The thickness of the acrylic sheets was set to 2 mm, 5 mm, or 10 mm, as appropriate, according to the thickness of the fitted fuel gel. A titanium mesh (Alfa Aesar 40921, cut to 10 mm wide×40 mm long) was used as a collector plate and a silicone sheet (As One or the like) 0.5 mm thick was used as a spacer; a 14-mm square hole, the size of the electrode, was made in the middle section of the silicone sheet between the fuel gel and the cathode and anode, so that the electrode would be in contact with the fuel gel, and no square hole was made in the silicone sheet between the anode and the anode side of the outer frame. That is, the layering followed the sequence of: acrylic sheet (outer frame: square hole), titanium mesh, cathode, silicone sheet (square hole), silicone sheet where the fuel gel is held at the middle section, silicone sheet (square hole), anode, titanium mesh, silicone sheet, acrylic sheet (outer frame).

The anode and the fuel gel were prepared as follows.

1. Preparation of Enzyme Solution for the Anode

A glucose dehydrogenase solution was prepared as the enzyme solution for the anode. Glucose dehydrogenase from the NBRC 12552 strain of *Acinetobacter calcoaceticus* was prepared as follows as the glucose dehydrogenase. The BL21 (DE3) strain of *E. coli* was transformed with the enzyme expression plasmid pET-22b(+)-sGdh, and a colony was inoculated onto 300 mL of an LB/Amp culture medium (includes 50 μg/mL ampicillin) and cultured overnight at 37° C. Next, 20 L of the LB/Amp culture medium was fed into a jar fermenter and 200 mL of pre-culture solution was added thereto for about one hour of culturing at 37° C. (until O.D.=0.1); 0.01 mM IPTG was added to induce protein expression, and culturing was continued overnight with shaking at 28° C. The culture solution was centrifuged and the precipitate obtained by removing the supernatant was stored frozen at −80° C. 5 g of the frozen stored enzyme expression bacterial cells was suspended in 15 mL of phosphate buffered saline (PBS) buffer solution. An ultrasonic disruptor (15 seconds at 15 W; XL2000 made by MISONIX) was used to carry out ten rounds of disruption over ice. The disruption solution underwent 20 minutes of centrifuge separation at 4° C. and 5,000 rpm, and the fractionated supernatant was filtered with a cellulose acetate 0.45 μm filter (ADBANTEC). An open column was packed with 10 mL of resin for histidine tag purification (TALON®, made by Clontech), and an amount of equilibration buffer solution (300 mM NaCl, 1×PBS) five times the bed volume brought the open column to equilibrium. The pre-treated sample was applied to the column, which was rinsed with an amount of rinsing buffer solution (300 mM NaCl, 10 mM imidazole, 1×PBS) five times the bed volume; thereafter, elution was carried out with an amount of eluting buffer solution (300 mM NaCl, 150 mM imidazole, 1×PBS) three times the bed volume. The recovered eluate was concentrated using an ultrafiltration membrane (AMICON® Ultra-44, made by Millipore) and thereafter dialyzed to a final enzyme solution buffer (10 mM Tris-HCl pH 7.5, 0.1 mM $CaCl_2$). Prior to use in an electrode, the enzyme solution underwent five minutes of centrifuge separation at 15,000 rpm, and the fractionated supernatant was again concentrated so as to reach 20 mg/mL or higher.

2. Preparation of the Anode $CaCl_2$ and PQQ were added to the enzyme solution for the anode as prepared in step 1 above, in amounts of 1 mM and 1 μm, respectively, and incubation was performed at 4° C. Carbon felt (50 g/m² carbon matte) was cut to 1.4 cm×1.4 cm with a cutter. 0.22 mL of a solution obtained by adding sodium phosphate buffer (pH 7.0) and mPMS to the enzyme solution in amounts of 0.1 M and 5 mM, respectively, was added in a dropwise manner to the carbon felt and air-dried for use.

3. Preparation of the Fuel Gel

The prepared solution was dissolved in a microwave oven into 1 (w/v) % agarose, 60 mM D-glucose, and 0.1 M sodium phosphate buffer (pH 7.0) and poured into and hardened in the mold frame made of acrylic.

By way of comparison, a biological fuel cell used as an electrode catalyst in the cathode was constructed without crystallization of the enzyme solution prepared in step 2 of the crystallization enzyme in the steps described above (comparative example A). Also constructed was a biological fuel cell used as the electrode catalyst of the cathode, without crystallization of an enzyme solution prepared to have a bilirubin oxidase (Amano Enzyme; BO Amano 3, hereinafter abbreviated as "BOD") concentration of 20 mg/mL (comparative example B). Additionally constructed was a biological fuel cell using a cathode on which the enzyme crystal of CotA laccase was immobilized in the procedure in step 2, using CP not coated with KB, as the electroconductive base material for the cathode (comparative example C).

Step 4: Electrochemical Measurement of the Biological Fuel Cell

The voltage generated when a constant electric current was made to flow using an electron adding device was measured, and the power density was found on the basis of the electric current value.

Step 5: Measurement of the Amount of Enzyme on the Electrode

The amount of enzyme on the electrode was measured by an enzyme immunoassay (EIA), to correct the value of the power density. The detailed procedure of the EIA is shown below.
Purchased Reagents
PBS (Phosphate Buffered Saline; Sigma-Aldrich)
PBS-T (Phosphate Buffered Saline with Tween 20; Sigma-Aldrich)
Blocking agent (Block Ace powder, Dainippon Pharmaceutical)
Reaction buffer (44.5 mL PBS, 0.5 mL 1% (w/v) Triton X-100, and 5 mL Block Ace)
HRP-labeled anti-mouse IgG antibody (Anti-Mouse Ig, HRP-Linked Whole Ab; Amersham)
Coloring reagent (TMBOne Solution; Promega)
Measuring Reagents
Anti-serum solution (diluted 10,000-fold with reaction buffer)
Secondary antibody solution (diluted 4,000-fold with blocking agent)

Measurement Procedure
1. After measurement, the electrode was placed in a tube and allowed to stand for two hours in Block Ace
3. Rinsed three times with PBS-T
4. Allowed to stand for one hour in anti-serum solution
6. Rinsed three times with PBS-T
8. Allowed to stand for one hour in secondary antibody solution
9. Rinsed three times with PBS-T, and then rinsed two times with PBS
10. Allowed to stand for five minutes in the coloring reagent, and then the reaction was stopped with 2 mL of hydrochloric acid (1 N)
12. Measurement with spectrophotometer (measuring the differential value from absorbance at 450 nm to absorbance at 595 nm (background))

Figure 20:
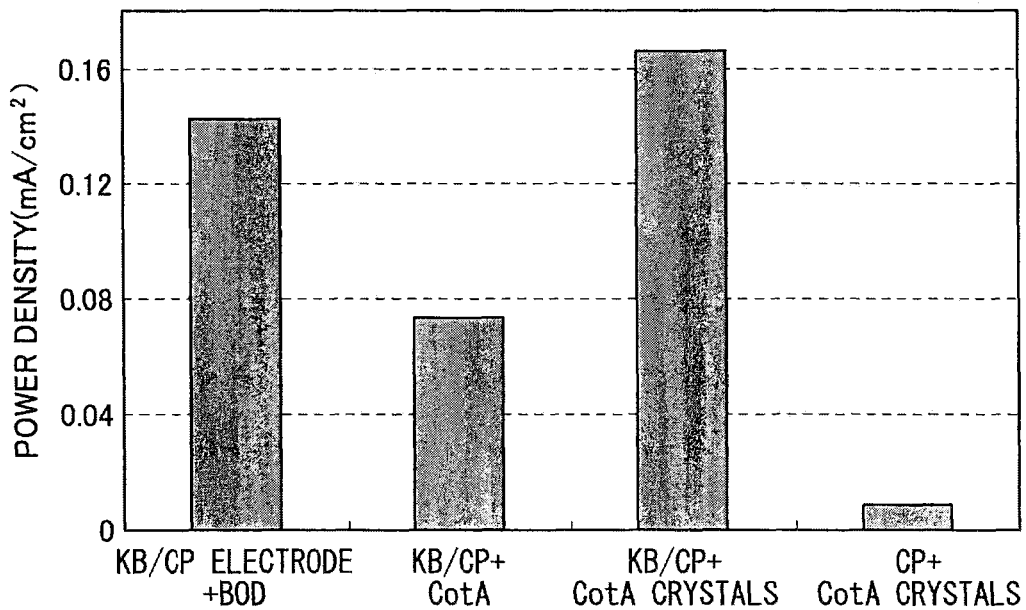
FIG. 20 is a graph illustrating the results from a twentieth embodiment, from when a performance assessment according to a biological fuel cell using an electrode having enzyme crystals immobilized thereon was examined.

The results are shown in FIG. 20. In FIG. 20, KB/CP electrode+BOD illustrates the results of comparative example B; KB/CP+CotA illustrates the results of comparative example A; KB/CP+CotA crystal illustrates the results of the present example, and CP+CotA illustrates the results of comparative example C. These results provide confirmation that crystallizing the enzyme to be used as the cathode-side catalyst provides enhanced output of the battery cell. It was also demonstrated that crystallizing and immobilizing the enzyme on the electroconductive base material also makes it possible to create an electrode of high practical value.

INDUSTRIAL APPLICABILITY

The present invention relates to an electrode having enzyme crystals immobilized thereon, a method for producing an electrode having enzyme crystals immobilized thereon, and a biological fuel cell and biosensor provided with an electrode having enzyme crystals immobilized thereon, and can be utilized in any field where an enzyme electrode is required, especially industrial fields such as medicine, food products, and the environment.

---

The invention claimed is:

1. A method for producing a biological fuel cell, the method comprising:
   (a) immobilizing an enzyme crystal onto an electroconductive base material, thereby forming an electrode comprising an enzyme crystal immobilized thereon;
   (b) forming the enzyme-immobilized electrode of (a) so that an anode and a cathode face each other; and
   (c) arranging an ion-conductive material so as to isolate the anode and cathode from each other, thereby producing the biological fuel cell,
   wherein the electroconductive base material is optionally connected to an external electrical circuit;
   wherein the enzyme crystal serves as an electrode catalyst;
   wherein the enzyme has an amino acid sequence of SEQ ID NO: 2, 4, 6, and 8; and wherein the enzyme is selected from the group consisting of pyrroloquinoline quinone-dependent glucose dehydrogenase from *Acinetobacter calcoaceticus* and CotA laccase from *Bacillus subtilis*.

2. The method of claim 1,
   wherein the anode is the electrode comprising the enzyme crystal immobilized thereon and
   the enzyme crystal is a crystal of an enzyme for catalyzing an oxidation reaction.

3. The method of claim 1,
   wherein the cathode is the electrode comprising the enzyme crystal immobilized thereon and
   the enzyme crystal is a crystal of an enzyme for catalyzing a reduction reaction.

4. The method of claim 1, wherein the enzyme is said pyrroloquinoline quinone-dependent glucose dehydrogenase from *Acinetobacter calcoaceticus* of SEQ ID NO: 2 or 4.

5. The method of claim 1, wherein the enzyme is said CotA laccase from *Bacillus subtilis* of SEQ ID NO: 6 or 8.

6. A method for producing a biological fuel cell, the method comprising:
   (a) crystallizing an enzyme from an enzyme solution on an electroconductive base material; and
   (b) immobilizing the enzyme crystal on the electroconductive base material, thereby forming an electrode comprising an enzyme crystal immobilized thereon;
   (c) forming the enzyme-immobilized electrode of (b) so that an anode and a cathode face each others; and
   (d) arranging an ion-conductive material so as to isolate the anode and cathode from each other, thereby producing the biological fuel cell,
   wherein the electroconductive base material is optionally connected to an external electrical circuit;
   wherein the enzyme crystal serves as an electrode catalyst;
   wherein the enzyme has an amino acid sequence of SEQ ID NO: 2, 4, 6, and 8; and wherein the enzyme is selected from the group consisting of pyrroloquinoline quinone-dependent glucose dehydrogenase from *Acinetobacter calcoaceticus* and CotA laccase from *Bacillus subtilis*.

7. The method of claim 6,
   wherein the anode is the electrode comprising the enzyme crystal immobilized thereon and
   the enzyme crystal is a crystal of an enzyme for catalyzing an oxidation reaction.

8. The method of claim 6,
   wherein the cathode is the electrode comprising the enzyme crystal immobilized thereon and
   the enzyme crystal is a crystal of an enzyme for catalyzing a reduction reaction.

9. The method of claim 6, wherein the enzyme is said pyrroloquinoline quinone-dependent glucose dehydrogenase from *Acinetobacter calcoaceticus* of SEQ ID NO: 2 or 4.

10. The method of claim 6, wherein the enzyme is said CotA laccase from *Bacillus subtilis* of SEQ ID NO: 6 or 8.

* * * * *

SEQUENCE LISTING

```
<160> NUMBER OF SEQ ID NOS: 8

<210> SEQ ID NO 1
<211> LENGTH: 1612
<212> TYPE: DNA
<213> ORGANISM: Acinetobacter calcoaceticus
<220> FEATURE:
<221> NAME/KEY: CDS
<222> LOCATION: (152)..(1585)

<400> SEQUENCE: 1
agctactttt atgcaacaga gcctttcaga aatttagatt ttaatagatt cgttattcat      60
cataatacaa atcatataga gaactcgtac aaacccttta ttagaggttt aaaaattctc     120
ggaaaatttt gacaatttat aaggtggaca c atg aat aaa cat tta ttg gct       172
                                   Met Asn Lys His Leu Leu Ala
                                    1               5 aaa att gct tta tta agc gct gtt cag cta gtt aca ctc tca gca ttt       220
Lys Ile Ala Leu Leu Ser Ala Val Gln Leu Val Thr Leu Ser Ala Phe
        10                  15                  20 gct gat gtt cct cta act cca tct caa ttt gct aaa gcg aaa tca gag       268
Ala Asp Val Pro Leu Thr Pro Ser Gln Phe Ala Lys Ala Lys Ser Glu
    25                  30                  35 aac ttt gac aag aaa gtt att cta tct aat cta aat aag ccg cat gct       316
Asn Phe Asp Lys Lys Val Ile Leu Ser Asn Leu Asn Lys Pro His Ala
40                  45                  50                  55
```

```
ttg tta tgg gga cca gat aat caa att tgg tta act gag cga gca aca       364
Leu Leu Trp Gly Pro Asp Asn Gln Ile Trp Leu Thr Glu Arg Ala Thr
            60                  65                  70 ggt aag att cta aga gtt aat cca gag tcg ggt agt gta aaa aca gtt       412
Gly Lys Ile Leu Arg Val Asn Pro Glu Ser Gly Ser Val Lys Thr Val
        75                  80                  85 ttt cag gta cca gag att gtc aat gat gct gat ggg cag aat ggt tta       460
Phe Gln Val Pro Glu Ile Val Asn Asp Ala Asp Gly Gln Asn Gly Leu
        90                  95                 100 tta ggt ttt gcc ttc cat cct gat ttt aaa aat aat cct tat atc tat       508
Leu Gly Phe Ala Phe His Pro Asp Phe Lys Asn Asn Pro Tyr Ile Tyr
        105                 110                 115 att tca ggt aca ttt aaa aat ccg aaa tct aca gat aaa gaa tta ccg       556
Ile Ser Gly Thr Phe Lys Asn Pro Lys Ser Thr Asp Lys Glu Leu Pro
120             125                 130                 135 aac caa acg att att cgt cgt tat acc tat aat aaa tca aca gat acg       604
Asn Gln Thr Ile Ile Arg Arg Tyr Thr Tyr Asn Lys Ser Thr Asp Thr
                140                 145                 150 ctc gag aag cca gtc gat tta tta gca gga tta cct tca tca aaa gac       652
Leu Glu Lys Pro Val Asp Leu Leu Ala Gly Leu Pro Ser Ser Lys Asp
                155                 160                 165 cat cag tca ggt cgt ctt gtc att ggg cca gat caa aag att tat tat       700
His Gln Ser Gly Arg Leu Val Ile Gly Pro Asp Gln Lys Ile Tyr Tyr
                170                 175                 180 acg att ggt gac caa ggg cgt aac cag ctt gct tat ttg ttc ttg cca       748
Thr Ile Gly Asp Gln Gly Arg Asn Gln Leu Ala Tyr Leu Phe Leu Pro
        185                 190                 195 aat caa gca caa cat acg cca act caa caa gaa ctg aat ggt aaa gac       796
Asn Gln Ala Gln His Thr Pro Thr Gln Gln Glu Leu Asn Gly Lys Asp
200             205                 210                 215 tat cac acc tat atg ggt aaa gta cta cgc tta aat ctt gat gga agt       844
Tyr His Thr Tyr Met Gly Lys Val Leu Arg Leu Asn Leu Asp Gly Ser
                220                 225                 230 att cca aag gat aat cca agt ttt aac ggg gtg gtt agc cat att tat       892
Ile Pro Lys Asp Asn Pro Ser Phe Asn Gly Val Val Ser His Ile Tyr
            235                 240                 245 aca ctt gga cat cgt aat ccg cag ggc tta gca ttc act cca aat ggt       940
Thr Leu Gly His Arg Asn Pro Gln Gly Leu Ala Phe Thr Pro Asn Gly
        250                 255                 260 aaa tta ttg cag tct gaa caa ggc cca aac tct gac gat gaa att aac       988
Lys Leu Leu Gln Ser Glu Gln Gly Pro Asn Ser Asp Asp Glu Ile Asn
        265                 270                 275 ctc att gtc aaa ggt ggc aat tat ggt tgg ccg aat gta gca ggt tat      1036
Leu Ile Val Lys Gly Gly Asn Tyr Gly Trp Pro Asn Val Ala Gly Tyr
280                 285                 290                 295 aaa gat gat agt ggc tat gct tat gca aat tat tca gca gca gcc aat      1084
Lys Asp Asp Ser Gly Tyr Ala Tyr Ala Asn Tyr Ser Ala Ala Ala Asn
                300                 305                 310 aag tca att aag gat tta gct caa aat gga gta aaa gta gcc gca ggg      1132
Lys Ser Ile Lys Asp Leu Ala Gln Asn Gly Val Lys Val Ala Ala Gly
            315                 320                 325 gtc cct gtg acg aaa gaa tct gaa tgg act ggt aaa aac ttt gtc cca      1180
Val Pro Val Thr Lys Glu Ser Glu Trp Thr Gly Lys Asn Phe Val Pro
        330                 335                 340 cca tta aaa act tta tat acc gtt caa gat acc tac aac tat aac gat      1228
Pro Leu Lys Thr Leu Tyr Thr Val Gln Asp Thr Tyr Asn Tyr Asn Asp
        345                 350                 355 cca act tgt gga gag atg acc tac att tgc tgg cca aca gtt gca ccg      1276
Pro Thr Cys Gly Glu Met Thr Tyr Ile Cys Trp Pro Thr Val Ala Pro
```

```
                360             365             370             375
tca tct gcc tat gtc tat aag ggc ggt aaa aaa gca att act ggt tgg    1324
Ser Ser Ala Tyr Val Tyr Lys Gly Gly Lys Lys Ala Ile Thr Gly Trp
            380             385             390 gaa aat aca tta ttg gtt cca tct tta aaa cgt ggt gtc att ttc cgt    1372
Glu Asn Thr Leu Leu Val Pro Ser Leu Lys Arg Gly Val Ile Phe Arg
        395             400             405 att aag tta gat cca act tat agc act act tat gat gac gct gta ccg    1420
Ile Lys Leu Asp Pro Thr Tyr Ser Thr Thr Tyr Asp Asp Ala Val Pro
    410             415             420 atg ttt aag agc aac aac cgt tat cgt gat gtg att gca agt cca gat    1468
Met Phe Lys Ser Asn Asn Arg Tyr Arg Asp Val Ile Ala Ser Pro Asp
425             430             435 ggg aat gtc tta tat gta tta act gat act gcc gga aat gtc caa aaa    1516
Gly Asn Val Leu Tyr Val Leu Thr Asp Thr Ala Gly Asn Val Gln Lys
440             445             450             455 gat gat ggc tca gta aca aat aca tta gaa aac cca gga tct ctc att    1564
Asp Asp Gly Ser Val Thr Asn Thr Leu Glu Asn Pro Gly Ser Leu Ile
            460             465             470 aag ttc acc tat aag gct aag taatacagtc gcattaaaaa accgatc          1612
Lys Phe Thr Tyr Lys Ala Lys
        475

<210> SEQ ID NO 2
<211> LENGTH: 478
<212> TYPE: PRT
<213> ORGANISM: Acinetobacter calcoaceticus

<400> SEQUENCE: 2

Met Asn Lys His Leu Leu Ala Lys Ile Ala Leu Leu Ser Ala Val Gln
1               5                   10                  15

Leu Val Thr Leu Ser Ala Phe Ala Asp Val Pro Leu Thr Pro Ser Gln
            20                  25                  30

Phe Ala Lys Ala Lys Ser Glu Asn Phe Asp Lys Lys Val Ile Leu Ser
        35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Asp Phe
            100                 105                 110

Lys Asn Asn Pro Tyr Ile Tyr Ile Ser Gly Thr Phe Lys Asn Pro Lys
        115                 120                 125

Ser Thr Asp Lys Glu Leu Pro Asn Gln Thr Ile Ile Arg Arg Tyr Thr
    130                 135                 140

Tyr Asn Lys Ser Thr Asp Thr Leu Glu Lys Pro Val Asp Leu Leu Ala
145                 150                 155                 160

Gly Leu Pro Ser Ser Lys Asp His Gln Ser Gly Arg Leu Val Ile Gly
                165                 170                 175

Pro Asp Gln Lys Ile Tyr Tyr Thr Ile Gly Asp Gln Gly Arg Asn Gln
            180                 185                 190

Leu Ala Tyr Leu Phe Leu Pro Asn Gln Ala Gln His Thr Pro Thr Gln
        195                 200                 205

Gln Glu Leu Asn Gly Lys Asp Tyr His Thr Tyr Met Gly Lys Val Leu
    210                 215                 220
```

```
Arg Leu Asn Leu Asp Gly Ser Ile Pro Lys Asp Asn Pro Ser Phe Asn
225                 230                 235                 240

Gly Val Val Ser His Ile Tyr Thr Leu Gly His Arg Asn Pro Gln Gly
            245                 250                 255

Leu Ala Phe Thr Pro Asn Gly Lys Leu Leu Gln Ser Glu Gln Gly Pro
        260                 265                 270

Asn Ser Asp Asp Glu Ile Asn Leu Ile Val Lys Gly Gly Asn Tyr Gly
    275                 280                 285

Trp Pro Asn Val Ala Gly Tyr Lys Asp Ser Gly Tyr Ala Tyr Ala
290                 295                 300

Asn Tyr Ser Ala Ala Asn Lys Ser Ile Lys Asp Leu Ala Gln Asn
305                 310                 315                 320

Gly Val Lys Val Ala Gly Val Pro Val Thr Lys Glu Ser Glu Trp
                325                 330                 335

Thr Gly Lys Asn Phe Val Pro Pro Leu Lys Thr Leu Tyr Thr Val Gln
            340                 345                 350

Asp Thr Tyr Asn Tyr Asn Asp Pro Thr Cys Gly Glu Met Thr Tyr Ile
        355                 360                 365

Cys Trp Pro Thr Val Ala Pro Ser Ser Tyr Val Tyr Lys Gly Gly
    370                 375                 380

Lys Lys Ala Ile Thr Gly Trp Glu Asn Thr Leu Leu Val Pro Ser Leu
385                 390                 395                 400

Lys Arg Gly Val Ile Phe Arg Ile Lys Leu Asp Pro Thr Tyr Ser Thr
                405                 410                 415

Thr Tyr Asp Asp Ala Val Pro Met Phe Lys Ser Asn Asn Arg Tyr Arg
            420                 425                 430

Asp Val Ile Ala Ser Pro Asp Gly Asn Val Leu Tyr Val Leu Thr Asp
        435                 440                 445

Thr Ala Gly Asn Val Gln Lys Asp Asp Gly Ser Val Thr Asn Thr Leu
    450                 455                 460

Glu Asn Pro Gly Ser Leu Ile Lys Phe Thr Tyr Lys Ala Lys
465                 470                 475

<210> SEQ ID NO 3
<211> LENGTH: 1458
<212> TYPE: DNA
<213> ORGANISM: Acinetobacter calcoaceticus
<220> FEATURE:
<221> NAME/KEY: CDS
<222> LOCATION: (1)..(1458)

<400> SEQUENCE: 3 atg aat aaa cat tta ttg gct aaa att gcg tta tta agc gct gtt cag        48
Met Asn Lys His Leu Leu Ala Lys Ile Ala Leu Leu Ser Ala Val Gln
1               5                   10                  15 cta gtt acg ctc tca gca ttt gct gat gtt cct ctt aca cca tct caa        96
Leu Val Thr Leu Ser Ala Phe Ala Asp Val Pro Leu Thr Pro Ser Gln
            20                  25                  30 ttt gct aaa gcg aaa tcg gaa aac ttt gac aag aaa gtt att cta tct       144
Phe Ala Lys Ala Lys Ser Glu Asn Phe Asp Lys Lys Val Ile Leu Ser
        35                  40                  45 aat tta aat aag cca cat gct ttg ttg tgg ggg cct gat aat caa att       192
Asn Leu Asn Lys Pro His Ala Leu Leu Trp Gly Pro Asp Asn Gln Ile
    50                  55                  60 tgg tta acg gag cgg gca aca ggg aag att cta aga gtg aat cca gag       240
Trp Leu Thr Glu Arg Ala Thr Gly Lys Ile Leu Arg Val Asn Pro Glu
65                  70                  75                  80
```

| | |
|---|---|
| tcg ggc agt gta aaa aca gtt ttt cag gtt cct gag att gta aat gat<br>Ser Gly Ser Val Lys Thr Val Phe Gln Val Pro Glu Ile Val Asn Asp<br>            85                  90                  95 | 288 |
| gct gat gga caa aac ggt tta ttg ggt ttt gcc ttt cat cct gac ttt<br>Ala Asp Gly Gln Asn Gly Leu Leu Gly Phe Ala Phe His Pro Asp Phe<br>              100               105              110 | 336 |
| aaa aat aat cct tat atc tat att tca ggt act ttt aaa aat ccg aaa<br>Lys Asn Asn Pro Tyr Ile Tyr Ile Ser Gly Thr Phe Lys Asn Pro Lys<br>            115               120              125 | 384 |
| tct aca gat aaa gaa tta ccg aat caa act att att cgt cga tat acc<br>Ser Thr Asp Lys Glu Leu Pro Asn Gln Thr Ile Ile Arg Arg Tyr Thr<br>130                 135              140 | 432 |
| tat aac aaa tcg aca gat act ctt gag aaa cca gta gat tta tta gca<br>Tyr Asn Lys Ser Thr Asp Thr Leu Glu Lys Pro Val Asp Leu Leu Ala<br>145               150              155              160 | 480 |
| gga tta cct tca tcg aaa gac cat cag tcg ggt cgc ctt gtc att ggt<br>Gly Leu Pro Ser Ser Lys Asp His Gln Ser Gly Arg Leu Val Ile Gly<br>                 165              170              175 | 528 |
| cca gac caa aag att tac tat acg att ggt gat cag ggg cgt aac cag<br>Pro Asp Gln Lys Ile Tyr Tyr Thr Ile Gly Asp Gln Gly Arg Asn Gln<br>            180               185              190 | 576 |
| ctg gct tat tta ttc tta cca aat caa gca cag cat acg ccg act caa<br>Leu Ala Tyr Leu Phe Leu Pro Asn Gln Ala Gln His Thr Pro Thr Gln<br>               195              200              205 | 624 |
| cag gaa ctg aat ggc aaa gac tat cat acc tat atg ggt aaa gta tta<br>Gln Glu Leu Asn Gly Lys Asp Tyr His Thr Tyr Met Gly Lys Val Leu<br>210                 215              220 | 672 |
| cgc tta aat ctg gat gga agt att cca aaa gat aat cca agc ttt aac<br>Arg Leu Asn Leu Asp Gly Ser Ile Pro Lys Asp Asn Pro Ser Phe Asn<br>225               230              235              240 | 720 |
| ggt gta gtg agc cat att tat acg ctc ggt cat cgt aat cca cag ggc<br>Gly Val Val Ser His Ile Tyr Thr Leu Gly His Arg Asn Pro Gln Gly<br>               245              250              255 | 768 |
| ttg gca ttt act cca aat ggt aaa ctg ttg caa tct gaa cag ggt cca<br>Leu Ala Phe Thr Pro Asn Gly Lys Leu Leu Gln Ser Glu Gln Gly Pro<br>            260               265              270 | 816 |
| aac tct gac gat gaa att aac ctc att gtc aaa ggt ggt aac tat ggc<br>Asn Ser Asp Asp Glu Ile Asn Leu Ile Val Lys Gly Gly Asn Tyr Gly<br>            275               280              285 | 864 |
| tgg cca aat gta gcg ggt tat aaa gat gat agt ggt tat gcc tat gca<br>Trp Pro Asn Val Ala Gly Tyr Lys Asp Asp Ser Gly Tyr Ala Tyr Ala<br>         290                 295              300 | 912 |
| aat tat tcg gca gca gcc aat aaa tcg att aaa gat tta gcg caa aat<br>Asn Tyr Ser Ala Ala Ala Asn Lys Ser Ile Lys Asp Leu Ala Gln Asn<br>305               310              315              320 | 960 |
| ggt gtg aaa gtg gca gct ggc gtt cca gtg act aaa gag tct gaa tgg<br>Gly Val Lys Val Ala Ala Gly Val Pro Val Thr Lys Glu Ser Glu Trp<br>               325              330              335 | 1008 |
| act ggt aaa aac ttt gta ccg ccg tta aaa act tta tat acc gtc caa<br>Thr Gly Lys Asn Phe Val Pro Pro Leu Lys Thr Leu Tyr Thr Val Gln<br>            340               345              350 | 1056 |
| gat acc tat aac tat aat gac cca acc tgt ggg gaa atg acc tac att<br>Asp Thr Tyr Asn Tyr Asn Asp Pro Thr Cys Gly Glu Met Thr Tyr Ile<br>               355              360              365 | 1104 |
| tgc tgg cca acg gtt gcg ccg tca tct gct tat gtc tat aag gga ggc<br>Cys Trp Pro Thr Val Ala Pro Ser Ser Ala Tyr Val Tyr Lys Gly Gly<br>         370                 375              380 | 1152 |
| aaa aaa gca att acc ggt tgg gaa aat acc tta ttg gtt cca tct tta<br>Lys Lys Ala Ile Thr Gly Trp Glu Asn Thr Leu Leu Val Pro Ser Leu | 1200 |

```
aag cgc ggt gtt att ttc cgt att aag cta gat cca act tac agt acc    1248
Lys Arg Gly Val Ile Phe Arg Ile Lys Leu Asp Pro Thr Tyr Ser Thr
            405                 410                 415 act tat gat gat gct gtg ccg atg ttt aag agc aac aat cgt tat cgt    1296
Thr Tyr Asp Asp Ala Val Pro Met Phe Lys Ser Asn Asn Arg Tyr Arg
            420                 425                 430 gac gtg att gca agt cca gat gga aat gtt tta tat gta ttg act gat    1344
Asp Val Ile Ala Ser Pro Asp Gly Asn Val Leu Tyr Val Leu Thr Asp
            435                 440                 445 act gcc gga aat gtc caa aaa gat gat ggt tct gta acg aat aca tta    1392
Thr Ala Gly Asn Val Gln Lys Asp Asp Gly Ser Val Thr Asn Thr Leu
    450                 455                 460 gaa aac cca gga tct ctg att aaa ttt aca tat aaa gct aag gcg cac    1440
Glu Asn Pro Gly Ser Leu Ile Lys Phe Thr Tyr Lys Ala Lys Ala His
465                 470                 475                 480 cac cac cac cac cac taa                                            1458
His His His His His
            485

<210> SEQ ID NO 4
<211> LENGTH: 485
<212> TYPE: PRT
<213> ORGANISM: Acinetobacter calcoaceticus

<400> SEQUENCE: 4

Met Asn Lys His Leu Leu Ala Lys Ile Ala Leu Leu Ser Ala Val Gln
1               5                   10                  15

Leu Val Thr Leu Ser Ala Phe Ala Asp Val Pro Leu Thr Pro Ser Gln
            20                  25                  30

Phe Ala Lys Ala Lys Ser Glu Asn Phe Asp Lys Lys Val Ile Leu Ser
        35                  40                  45

Asn Leu Asn Lys Pro His Ala Leu Leu Trp Gly Pro Asp Asn Gln Ile
    50                  55                  60

Trp Leu Thr Glu Arg Ala Thr Gly Lys Ile Leu Arg Val Asn Pro Glu
65                  70                  75                  80

Ser Gly Ser Val Lys Thr Val Phe Gln Val Pro Glu Ile Val Asn Asp
                85                  90                  95

Ala Asp Gly Gln Asn Gly Leu Leu Gly Phe Ala Phe His Pro Asp Phe
            100                 105                 110

Lys Asn Asn Pro Tyr Ile Tyr Ile Ser Gly Thr Phe Lys Asn Pro Lys
        115                 120                 125

Ser Thr Asp Lys Glu Leu Pro Asn Gln Thr Ile Ile Arg Arg Tyr Thr
    130                 135                 140

Tyr Asn Lys Ser Thr Asp Thr Leu Glu Lys Pro Val Asp Leu Leu Ala
145                 150                 155                 160

Gly Leu Pro Ser Ser Lys Asp His Gln Ser Gly Arg Leu Val Ile Gly
                165                 170                 175

Pro Asp Gln Lys Ile Tyr Tyr Thr Ile Gly Asp Gln Gly Arg Asn Gln
            180                 185                 190

Leu Ala Tyr Leu Phe Leu Pro Asn Gln Ala Gln His Thr Pro Thr Gln
        195                 200                 205

Gln Glu Leu Asn Gly Lys Asp Tyr His Thr Tyr Met Gly Lys Val Leu
    210                 215                 220

Arg Leu Asn Leu Asp Gly Ser Ile Pro Lys Asp Asn Pro Ser Phe Asn
225                 230                 235                 240
```

-continued

```
Gly Val Val Ser His Ile Tyr Thr Leu Gly His Arg Asn Pro Gln Gly
                245                 250                 255

Leu Ala Phe Thr Pro Asn Gly Lys Leu Leu Gln Ser Glu Gln Gly Pro
            260                 265                 270

Asn Ser Asp Asp Glu Ile Asn Leu Ile Val Lys Gly Gly Asn Tyr Gly
        275                 280                 285

Trp Pro Asn Val Ala Gly Tyr Lys Asp Asp Ser Gly Tyr Ala Tyr Ala
    290                 295                 300

Asn Tyr Ser Ala Ala Asn Lys Ser Ile Lys Asp Leu Ala Gln Asn
305                 310                 315                 320

Gly Val Lys Val Ala Ala Gly Val Pro Val Thr Lys Glu Ser Glu Trp
                325                 330                 335

Thr Gly Lys Asn Phe Val Pro Pro Leu Lys Thr Leu Tyr Thr Val Gln
            340                 345                 350

Asp Thr Tyr Asn Tyr Asn Asp Pro Thr Cys Gly Glu Met Thr Tyr Ile
        355                 360                 365

Cys Trp Pro Thr Val Ala Pro Ser Ser Ala Tyr Val Tyr Lys Gly Gly
    370                 375                 380

Lys Lys Ala Ile Thr Gly Trp Glu Asn Thr Leu Leu Val Pro Ser Leu
385                 390                 395                 400

Lys Arg Gly Val Ile Phe Arg Ile Lys Leu Asp Pro Thr Tyr Ser Thr
                405                 410                 415

Thr Tyr Asp Asp Ala Val Pro Met Phe Lys Ser Asn Asn Arg Tyr Arg
            420                 425                 430

Asp Val Ile Ala Ser Pro Asp Gly Asn Val Leu Tyr Val Leu Thr Asp
        435                 440                 445

Thr Ala Gly Asn Val Gln Lys Asp Asp Gly Ser Val Thr Asn Thr Leu
    450                 455                 460

Glu Asn Pro Gly Ser Leu Ile Lys Phe Thr Tyr Lys Ala Lys Ala His
465                 470                 475                 480

His His His His
            485

<210> SEQ ID NO 5
<211> LENGTH: 1548
<212> TYPE: DNA
<213> ORGANISM: Bacillus subtilis
<220> FEATURE:
<221> NAME/KEY: CDS
<222> LOCATION: (1)..(1548)

<400> SEQUENCE: 5 atg aaa atg aca ctt gaa aaa ttt gtg gat gct ctc cca atc cca gat      48
Met Lys Met Thr Leu Glu Lys Phe Val Asp Ala Leu Pro Ile Pro Asp
1               5                   10                  15 aca cta aag cca gta cag caa tca aaa gaa aaa aca tac tac gaa gtc      96
Thr Leu Lys Pro Val Gln Gln Ser Lys Glu Lys Thr Tyr Tyr Glu Val
            20                  25                  30 acc atg gag gaa tgc act cat cag ctc cat cgc gat ctc cct cca acc     144
Thr Met Glu Glu Cys Thr His Gln Leu His Arg Asp Leu Pro Pro Thr
        35                  40                  45 cgc ctg tgg ggc tac aac ggc tta ttt ccg gga ccg acc att gag gtt     192
Arg Leu Trp Gly Tyr Asn Gly Leu Phe Pro Gly Pro Thr Ile Glu Val
    50                  55                  60 aaa aga aat gaa aac gta tat gta aaa tgg atg aat aac ctt cct tcc     240
Lys Arg Asn Glu Asn Val Tyr Val Lys Trp Met Asn Asn Leu Pro Ser
65                  70                  75                  80
```

```
acg cat ttc ctt ccg att gat cac acc att cat cac agt gac agc cag    288
Thr His Phe Leu Pro Ile Asp His Thr Ile His His Ser Asp Ser Gln
             85                  90                  95 cat gaa gag ccc gag gta aag act gtt gtt cat tta cac ggc ggc gtc    336
His Glu Glu Pro Glu Val Lys Thr Val Val His Leu His Gly Gly Val
        100                 105                 110 acg cca gat gat agt gac ggg tat ccg gag gct tgg ttt tcc aaa gac    384
Thr Pro Asp Asp Ser Asp Gly Tyr Pro Glu Ala Trp Phe Ser Lys Asp
            115                 120                 125 ttt gaa caa aca gga cct tat ttc aaa aga gag gtt tat cat tat cca    432
Phe Glu Gln Thr Gly Pro Tyr Phe Lys Arg Glu Val Tyr His Tyr Pro
        130                 135                 140 aac cag cag cgc ggg gct ata ttg tgg tat cac gat cac gcc atg gcg    480
Asn Gln Gln Arg Gly Ala Ile Leu Trp Tyr His Asp His Ala Met Ala
145                 150                 155                 160 ctc acc agg cta aat gtc tat gcc gga ctt gtc ggt gca tat atc att    528
Leu Thr Arg Leu Asn Val Tyr Ala Gly Leu Val Gly Ala Tyr Ile Ile
                165                 170                 175 cat gac cca aag gaa aaa cgc tta aaa ctg cct tca gac gaa tac gat    576
His Asp Pro Lys Glu Lys Arg Leu Lys Leu Pro Ser Asp Glu Tyr Asp
            180                 185                 190 gtg ccg ctt ctt atc aca gac cgc acg atc aat gag gat ggt tct ttg    624
Val Pro Leu Leu Ile Thr Asp Arg Thr Ile Asn Glu Asp Gly Ser Leu
        195                 200                 205 ttt tat ccg agc gca ccg gaa aac cct tct ccg tca ctg cct aat cct    672
Phe Tyr Pro Ser Ala Pro Glu Asn Pro Ser Pro Ser Leu Pro Asn Pro
210                 215                 220 tca atc gtt ccg gct ttt tgc gga gaa acc ata ctc gtc aac ggg aag    720
Ser Ile Val Pro Ala Phe Cys Gly Glu Thr Ile Leu Val Asn Gly Lys
225                 230                 235                 240 gta tgg cca tac ttg gaa gtc gag cca agg aaa tac cga ttc cgt gtc    768
Val Trp Pro Tyr Leu Glu Val Glu Pro Arg Lys Tyr Arg Phe Arg Val
                245                 250                 255 atc aac gcc tcc aat aca aga acc tat aac ctg tca ctc gat aat ggc    816
Ile Asn Ala Ser Asn Thr Arg Thr Tyr Asn Leu Ser Leu Asp Asn Gly
            260                 265                 270 gga gat ttt att cag att ggt tca gat gga ggg ctc ctg ccg cga tct    864
Gly Asp Phe Ile Gln Ile Gly Ser Asp Gly Gly Leu Leu Pro Arg Ser
        275                 280                 285 gtt aaa ctg aat tct ttc agc ctt gcg cct gct gaa cgt tac gat atc    912
Val Lys Leu Asn Ser Phe Ser Leu Ala Pro Ala Glu Arg Tyr Asp Ile
290                 295                 300 atc att gac ttc aca gca tat gaa gga gaa tcg atc att ttg gca aac    960
Ile Ile Asp Phe Thr Ala Tyr Glu Gly Glu Ser Ile Ile Leu Ala Asn
305                 310                 315                 320 agc gcg ggc tgc ggc ggt gac gtc aat cct gaa aca gat gcg aat atc   1008
Ser Ala Gly Cys Gly Gly Asp Val Asn Pro Glu Thr Asp Ala Asn Ile
                325                 330                 335 atg caa ttc aga gtc aca aaa cca ttg gca caa aaa gac gaa agc aga   1056
Met Gln Phe Arg Val Thr Lys Pro Leu Ala Gln Lys Asp Glu Ser Arg
            340                 345                 350 aag ccg aag tac ctc gcc tca tac cct tcg gta cag cat gaa aga ata   1104
Lys Pro Lys Tyr Leu Ala Ser Tyr Pro Ser Val Gln His Glu Arg Ile
        355                 360                 365 caa aac atc aga acg tta aaa ctg gca ggc acc cag gac gaa tac ggc   1152
Gln Asn Ile Arg Thr Leu Lys Leu Ala Gly Thr Gln Asp Glu Tyr Gly
370                 375                 380 aga ccc gtc ctt ctg ctt aat aac aaa cgc tgg cac gat ccc gtc aca   1200
Arg Pro Val Leu Leu Leu Asn Asn Lys Arg Trp His Asp Pro Val Thr
385                 390                 395                 400
```

```
gaa aca cca aaa gtc ggc aca act gaa ata tgg tcc att atc aac ccg   1248
Glu Thr Pro Lys Val Gly Thr Thr Glu Ile Trp Ser Ile Ile Asn Pro
            405                 410                 415 aca cgc gga aca cat ccg atc cac ctg cat cta gtc tcc ttc cgt gta   1296
Thr Arg Gly Thr His Pro Ile His Leu His Leu Val Ser Phe Arg Val
        420                 425                 430 tta gac cgg cgg ccg ttt gat atc gcc cgt tat caa gaa agc ggg gaa   1344
Leu Asp Arg Arg Pro Phe Asp Ile Ala Arg Tyr Gln Glu Ser Gly Glu
    435                 440                 445 ttg tcc tat acc ggt ccg gct gtc ccg ccg ccg agt gaa aag ggc       1392
Leu Ser Tyr Thr Gly Pro Ala Val Pro Pro Pro Ser Glu Lys Gly
450                 455                 460 tgg aaa gac acc att caa gcg cat gca ggt gaa gtc ctg aga atc gcg   1440
Trp Lys Asp Thr Ile Gln Ala His Ala Gly Glu Val Leu Arg Ile Ala
465                 470                 475                 480 gcg aca ttc ggt ccg tac agc gga cga tac gta tgg cat tgc cat att   1488
Ala Thr Phe Gly Pro Tyr Ser Gly Arg Tyr Val Trp His Cys His Ile
                485                 490                 495 cta gag cat gaa gac tat gac atg atg aga ccg atg gat ata act gat   1536
Leu Glu His Glu Asp Tyr Asp Met Met Arg Pro Met Asp Ile Thr Asp
            500                 505                 510 ccc cat aaa taa                                                   1548
Pro His Lys
515

<210> SEQ ID NO 6
<211> LENGTH: 515
<212> TYPE: PRT
<213> ORGANISM: Bacillus subtilis

<400> SEQUENCE: 6

Met Lys Met Thr Leu Glu Lys Phe Val Asp Ala Leu Pro Ile Pro Asp
1               5                   10                  15

Thr Leu Lys Pro Val Gln Gln Ser Lys Glu Lys Thr Tyr Tyr Glu Val
            20                  25                  30

Thr Met Glu Glu Cys Thr His Gln Leu His Arg Asp Leu Pro Pro Thr
        35                  40                  45

Arg Leu Trp Gly Tyr Asn Gly Leu Phe Pro Gly Pro Thr Ile Glu Val
    50                  55                  60

Lys Arg Asn Glu Asn Val Tyr Val Lys Trp Met Asn Asn Leu Pro Ser
65                  70                  75                  80

Thr His Phe Leu Pro Ile Asp His Thr Ile His His Ser Asp Ser Gln
                85                  90                  95

His Glu Glu Pro Glu Val Lys Thr Val Val His Leu His Gly Gly Val
            100                 105                 110

Thr Pro Asp Asp Ser Asp Gly Tyr Pro Glu Ala Trp Phe Ser Lys Asp
        115                 120                 125

Phe Glu Gln Thr Gly Pro Tyr Phe Lys Arg Glu Val Tyr His Tyr Pro
    130                 135                 140

Asn Gln Gln Arg Gly Ala Ile Leu Trp Tyr His Asp His Ala Met Ala
145                 150                 155                 160

Leu Thr Arg Leu Asn Val Tyr Ala Gly Leu Val Gly Ala Tyr Ile Ile
                165                 170                 175

His Asp Pro Lys Glu Lys Arg Leu Lys Leu Pro Ser Asp Glu Tyr Asp
            180                 185                 190

Val Pro Leu Leu Ile Thr Asp Arg Thr Ile Asn Glu Asp Gly Ser Leu
        195                 200                 205
```

```
Phe Tyr Pro Ser Ala Pro Glu Asn Pro Ser Pro Ser Leu Pro Asn Pro
    210                 215                 220

Ser Ile Val Pro Ala Phe Cys Gly Glu Thr Ile Leu Val Asn Gly Lys
225                 230                 235                 240

Val Trp Pro Tyr Leu Glu Val Glu Pro Arg Lys Tyr Arg Phe Arg Val
                245                 250                 255

Ile Asn Ala Ser Asn Thr Arg Thr Tyr Asn Leu Ser Leu Asp Asn Gly
            260                 265                 270

Gly Asp Phe Ile Gln Ile Gly Ser Asp Gly Gly Leu Leu Pro Arg Ser
        275                 280                 285

Val Lys Leu Asn Ser Phe Ser Leu Ala Pro Ala Glu Arg Tyr Asp Ile
    290                 295                 300

Ile Ile Asp Phe Thr Ala Tyr Glu Gly Glu Ser Ile Ile Leu Ala Asn
305                 310                 315                 320

Ser Ala Gly Cys Gly Gly Asp Val Asn Pro Glu Thr Asp Ala Asn Ile
                325                 330                 335

Met Gln Phe Arg Val Thr Lys Pro Leu Ala Gln Lys Asp Glu Ser Arg
            340                 345                 350

Lys Pro Lys Tyr Leu Ala Ser Tyr Pro Ser Val Gln His Glu Arg Ile
        355                 360                 365

Gln Asn Ile Arg Thr Leu Lys Leu Ala Gly Thr Gln Asp Glu Tyr Gly
    370                 375                 380

Arg Pro Val Leu Leu Asn Asn Lys Arg Trp His Asp Pro Val Thr
385                 390                 395                 400

Glu Thr Pro Lys Val Gly Thr Thr Glu Ile Trp Ser Ile Ile Asn Pro
                405                 410                 415

Thr Arg Gly Thr His Pro Ile His Leu His Leu Val Ser Phe Arg Val
            420                 425                 430

Leu Asp Arg Arg Pro Phe Asp Ile Ala Arg Tyr Gln Glu Ser Gly Glu
        435                 440                 445

Leu Ser Tyr Thr Gly Pro Ala Val Pro Pro Pro Ser Glu Lys Gly
    450                 455                 460

Trp Lys Asp Thr Ile Gln Ala His Ala Gly Glu Val Leu Arg Ile Ala
465                 470                 475                 480

Ala Thr Phe Gly Pro Tyr Ser Gly Arg Tyr Val Trp His Cys His Ile
                485                 490                 495

Leu Glu His Glu Asp Tyr Asp Met Met Arg Pro Met Asp Ile Thr Asp
            500                 505                 510

Pro His Lys
        515

<210> SEQ ID NO 7
<211> LENGTH: 1587
<212> TYPE: DNA
<213> ORGANISM: Bacillus subtilis
<220> FEATURE:
<221> NAME/KEY: CDS
<222> LOCATION: (1)..(1587)

<400> SEQUENCE: 7 atg aaa atg aca ctt gaa aaa ttt gtg gat gct ctc cca atc cca gat      48
Met Lys Met Thr Leu Glu Lys Phe Val Asp Ala Leu Pro Ile Pro Asp
1               5                   10                  15 aca cta aag cca gta cag caa tca aaa gaa aaa aca tac tac gaa gtc      96
Thr Leu Lys Pro Val Gln Gln Ser Lys Glu Lys Thr Tyr Tyr Glu Val
                20                  25                  30
```

```
acc atg gag gaa tgc act cat cag ctc cat cgc gat ctc cct cca acc    144
Thr Met Glu Glu Cys Thr His Gln Leu His Arg Asp Leu Pro Pro Thr
    35                  40                  45 cgc ctg tgg ggc tac aac ggc tta ttt ccg gga ccg acc att gag gtt    192
Arg Leu Trp Gly Tyr Asn Gly Leu Phe Pro Gly Pro Thr Ile Glu Val
50                  55                  60 aaa aga aat gaa aac gta tat gta aaa tgg atg aat aac ctt cct tcc    240
Lys Arg Asn Glu Asn Val Tyr Val Lys Trp Met Asn Asn Leu Pro Ser
65                  70                  75                  80 acg cat ttc ctt ccg att gat cac acc att cat cac agt gac agc cag    288
Thr His Phe Leu Pro Ile Asp His Thr Ile His His Ser Asp Ser Gln
                85                  90                  95 cat gaa gag ccc gag gta aag act gtt gtt cat tta cac ggc ggc gtc    336
His Glu Glu Pro Glu Val Lys Thr Val Val His Leu His Gly Gly Val
            100                 105                 110 acg cca gat gat agt gac ggg tat ccg gag gct tgg ttt tcc aaa gac    384
Thr Pro Asp Asp Ser Asp Gly Tyr Pro Glu Ala Trp Phe Ser Lys Asp
        115                 120                 125 ttt gaa caa aca gga cct tat ttc aaa aga gag gtt tat cat tat cca    432
Phe Glu Gln Thr Gly Pro Tyr Phe Lys Arg Glu Val Tyr His Tyr Pro
    130                 135                 140 aac cag cag cgc ggg gct ata ttg tgg tat cac gat cac gcc atg gcg    480
Asn Gln Gln Arg Gly Ala Ile Leu Trp Tyr His Asp His Ala Met Ala
145                 150                 155                 160 ctc acc agg cta aat gtc tat gcc gga ctt gtc ggt gca tat atc att    528
Leu Thr Arg Leu Asn Val Tyr Ala Gly Leu Val Gly Ala Tyr Ile Ile
                165                 170                 175 cat gac cca aag gaa aaa cgc tta aaa ctg cct tca gac gaa tac gat    576
His Asp Pro Lys Glu Lys Arg Leu Lys Leu Pro Ser Asp Glu Tyr Asp
            180                 185                 190 gtg ccg ctt ctt atc aca gac cgc acg atc aat gag gat ggt tct ttg    624
Val Pro Leu Leu Ile Thr Asp Arg Thr Ile Asn Glu Asp Gly Ser Leu
        195                 200                 205 ttt tat ccg agc gca ccg gaa aac cct tct ccg tca ctg cct aat cct    672
Phe Tyr Pro Ser Ala Pro Glu Asn Pro Ser Pro Ser Leu Pro Asn Pro
    210                 215                 220 tca atc gtt ccg gct ttt tgc gga gaa acc ata ctc gtc aac ggg aag    720
Ser Ile Val Pro Ala Phe Cys Gly Glu Thr Ile Leu Val Asn Gly Lys
225                 230                 235                 240 gta tgg cca tac ttg gaa gtc gag cca agg aaa tac cga ttc cgt gtc    768
Val Trp Pro Tyr Leu Glu Val Glu Pro Arg Lys Tyr Arg Phe Arg Val
                245                 250                 255 atc aac gcc tcc aat aca aga acc tat aac ctg tca ctc gat aat ggc    816
Ile Asn Ala Ser Asn Thr Arg Thr Tyr Asn Leu Ser Leu Asp Asn Gly
            260                 265                 270 gga gat ttt att cag att ggt tca gat gga ggg ctc ctg ccg cga tct    864
Gly Asp Phe Ile Gln Ile Gly Ser Asp Gly Gly Leu Leu Pro Arg Ser
        275                 280                 285 gtt aaa ctg aat tct ttc agc ctt gcg cct gct gaa cgt tac gat atc    912
Val Lys Leu Asn Ser Phe Ser Leu Ala Pro Ala Glu Arg Tyr Asp Ile
    290                 295                 300 atc att gac ttc aca gca tat gaa gga gaa tcg atc att ttg gca aac    960
Ile Ile Asp Phe Thr Ala Tyr Glu Gly Glu Ser Ile Ile Leu Ala Asn
305                 310                 315                 320 agc gcg ggc tgc ggc ggt gac gtc aat cct gaa aca gat gcg aat atc   1008
Ser Ala Gly Cys Gly Gly Asp Val Asn Pro Glu Thr Asp Ala Asn Ile
                325                 330                 335 atg caa ttc aga gtc aca aaa cca ttg gca caa aaa gac gaa agc aga   1056
Met Gln Phe Arg Val Thr Lys Pro Leu Ala Gln Lys Asp Glu Ser Arg
```

```
aag ccg aag tac ctc gcc tca tac cct tcg gta cag cat gaa aga ata      1104
Lys Pro Lys Tyr Leu Ala Ser Tyr Pro Ser Val Gln His Glu Arg Ile
        355                 360                 365 caa aac atc aga acg tta aaa ctg gca ggc acc cag gac gaa tac ggc      1152
Gln Asn Ile Arg Thr Leu Lys Leu Ala Gly Thr Gln Asp Glu Tyr Gly
370                 375                 380 aga ccc gtc ctt ctg ctt aat aac aaa cgc tgg cac gat ccc gtc aca      1200
Arg Pro Val Leu Leu Leu Asn Asn Lys Arg Trp His Asp Pro Val Thr
385                 390                 395                 400 gaa aca cca aaa gtc ggc aca act gaa ata tgg tcc att atc aac ccg      1248
Glu Thr Pro Lys Val Gly Thr Thr Glu Ile Trp Ser Ile Ile Asn Pro
                405                 410                 415 aca cgc gga aca cat ccg atc cac ctg cat cta gtc tcc ttc cgt gta      1296
Thr Arg Gly Thr His Pro Ile His Leu His Leu Val Ser Phe Arg Val
            420                 425                 430 tta gac cgg cgg ccg ttt gat atc gcc cgt tat caa gaa agc ggg gaa      1344
Leu Asp Arg Arg Pro Phe Asp Ile Ala Arg Tyr Gln Glu Ser Gly Glu
        435                 440                 445 ttg tcc tat acc ggt ccg gct gtc ccg ccg ccg cca agt gaa aag ggc      1392
Leu Ser Tyr Thr Gly Pro Ala Val Pro Pro Pro Pro Ser Glu Lys Gly
450                 455                 460 tgg aaa gac acc att caa gcg cat gca ggt gaa gtc ctg aga atc gcg      1440
Trp Lys Asp Thr Ile Gln Ala His Ala Gly Glu Val Leu Arg Ile Ala
465                 470                 475                 480 gcg aca ttc ggt ccg tac agc gga cga tac gta tgg cat tgc cat att      1488
Ala Thr Phe Gly Pro Tyr Ser Gly Arg Tyr Val Trp His Cys His Ile
                485                 490                 495 cta gag cat gaa gac tat gac atg atg aga ccg atg gat ata act gat      1536
Leu Glu His Glu Asp Tyr Asp Met Met Arg Pro Met Asp Ile Thr Asp
            500                 505                 510 ccc cat aaa aag ctt gcg gcc gca ctc gag cac cac cac cac cac cac      1584
Pro His Lys Lys Leu Ala Ala Ala Leu Glu His His His His His His
        515                 520                 525 tga                                                                  1587

<210> SEQ ID NO 8
<211> LENGTH: 528
<212> TYPE: PRT
<213> ORGANISM: Bacillus subtilis

<400> SEQUENCE: 8

Met Lys Met Thr Leu Glu Lys Phe Val Asp Ala Leu Pro Ile Pro Asp
1               5                   10                  15

Thr Leu Lys Pro Val Gln Gln Ser Lys Glu Lys Thr Tyr Tyr Glu Val
            20                  25                  30

Thr Met Glu Glu Cys Thr His Gln Leu His Arg Asp Leu Pro Pro Thr
        35                  40                  45

Arg Leu Trp Gly Tyr Asn Gly Leu Phe Pro Gly Pro Thr Ile Glu Val
    50                  55                  60

Lys Arg Asn Glu Asn Val Tyr Val Lys Trp Met Asn Asn Leu Pro Ser
65                  70                  75                  80

Thr His Phe Leu Pro Ile Asp His Thr Ile His His Ser Asp Ser Gln
                85                  90                  95

His Glu Glu Pro Glu Val Lys Thr Val Val His Leu His Gly Gly Val
            100                 105                 110

Thr Pro Asp Asp Ser Asp Gly Tyr Pro Glu Ala Trp Phe Ser Lys Asp
        115                 120                 125
```

```
Phe Glu Gln Thr Gly Pro Tyr Phe Lys Arg Glu Val Tyr His Tyr Pro
            130                 135                 140

Asn Gln Gln Arg Gly Ala Ile Leu Trp Tyr His Asp His Ala Met Ala
145                 150                 155                 160

Leu Thr Arg Leu Asn Val Tyr Ala Gly Leu Val Gly Ala Tyr Ile Ile
                165                 170                 175

His Asp Pro Lys Glu Lys Arg Leu Lys Leu Pro Ser Asp Glu Tyr Asp
            180                 185                 190

Val Pro Leu Leu Ile Thr Asp Arg Thr Ile Asn Glu Asp Gly Ser Leu
        195                 200                 205

Phe Tyr Pro Ser Ala Pro Glu Asn Pro Ser Pro Ser Leu Pro Asn Pro
    210                 215                 220

Ser Ile Val Pro Ala Phe Cys Gly Glu Thr Ile Leu Val Asn Gly Lys
225                 230                 235                 240

Val Trp Pro Tyr Leu Glu Val Glu Pro Arg Lys Tyr Arg Phe Arg Val
                245                 250                 255

Ile Asn Ala Ser Asn Thr Arg Thr Tyr Asn Leu Ser Leu Asp Asn Gly
            260                 265                 270

Gly Asp Phe Ile Gln Ile Gly Ser Asp Gly Gly Leu Leu Pro Arg Ser
        275                 280                 285

Val Lys Leu Asn Ser Phe Ser Leu Ala Pro Ala Glu Arg Tyr Asp Ile
    290                 295                 300

Ile Ile Asp Phe Thr Ala Tyr Glu Gly Glu Ser Ile Ile Leu Ala Asn
305                 310                 315                 320

Ser Ala Gly Cys Gly Gly Asp Val Asn Pro Glu Thr Asp Ala Asn Ile
                325                 330                 335

Met Gln Phe Arg Val Thr Lys Pro Leu Ala Gln Lys Asp Glu Ser Arg
            340                 345                 350

Lys Pro Lys Tyr Leu Ala Ser Tyr Pro Ser Val Gln His Glu Arg Ile
        355                 360                 365

Gln Asn Ile Arg Thr Leu Lys Leu Ala Gly Thr Gln Asp Glu Tyr Gly
    370                 375                 380

Arg Pro Val Leu Leu Leu Asn Asn Lys Arg Trp His Asp Pro Val Thr
385                 390                 395                 400

Glu Thr Pro Lys Val Gly Thr Thr Glu Ile Trp Ser Ile Ile Asn Pro
                405                 410                 415

Thr Arg Gly Thr His Pro Ile His Leu His Leu Val Ser Phe Arg Val
            420                 425                 430

Leu Asp Arg Arg Pro Phe Asp Ile Ala Arg Tyr Gln Glu Ser Gly Glu
        435                 440                 445

Leu Ser Tyr Thr Gly Pro Ala Val Pro Pro Pro Ser Glu Lys Gly
    450                 455                 460

Trp Lys Asp Thr Ile Gln Ala His Ala Gly Glu Val Leu Arg Ile Ala
465                 470                 475                 480

Ala Thr Phe Gly Pro Tyr Ser Gly Arg Tyr Val Trp His Cys His Ile
                485                 490                 495

Leu Glu His Glu Asp Tyr Asp Met Met Arg Pro Met Asp Ile Thr Asp
            500                 505                 510

Pro His Lys Lys Leu Ala Ala Ala Leu Glu His His His His
        515                 520                 525
```